US008580990B2

(12) United States Patent
Bertrand et al.

(10) Patent No.: US 8,580,990 B2
(45) Date of Patent: Nov. 12, 2013

(54) GOLD CATALYZED HYDROAMINATION OF ALKYNES AND ALLENES

(75) Inventors: Guy Bertrand, Riverside, CA (US);
Vincent Lavallo, Riverside, CA (US);
Guido D. Frey, Riverside, CA (US);
Bruno Donnadieu, Riverside, CA (US);
Michele Soleilhavoup, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 123 days.

(21) Appl. No.: 12/991,588

(22) PCT Filed: May 8, 2009

(86) PCT No.: PCT/US2009/043369
§ 371 (c)(1),
(2), (4) Date: Feb. 14, 2011

(87) PCT Pub. No.: WO2009/137810
PCT Pub. Date: Nov. 12, 2009

(65) Prior Publication Data
US 2011/0166349 A1     Jul. 7, 2011

Related U.S. Application Data

(60) Provisional application No. 61/051,826, filed on May 9, 2008.

(51) Int. Cl.
*C07C 209/60*     (2006.01)
*C07F 1/12*        (2006.01)

(52) U.S. Cl.
USPC ............................. 556/110; 564/470; 564/485

(58) Field of Classification Search
USPC .......................................... 564/470; 556/110
See application file for complete search history.

(56) References Cited

U.S. PATENT DOCUMENTS 6,576,796 B1    6/2003   Funke et al.

FOREIGN PATENT DOCUMENTS

DE        199 24 051 A1    11/2000
WO       WO 01/64620 A1    9/2001

OTHER PUBLICATIONS

Nilsson, et al. Inorg. Chem. 2006, 45, 6912-6921.*
International Search Report mailed on Jan. 8, 2010, for International Application No. PCT/US2009/043369 filed May 8, 2009, 3 pages.
Lavallo, V. et al., "Allene formation by gold catalyzed cross-coupling of masked carbenes and vinylidenes," *PNAS*, Aug. 21, 2007, vol. 104, No. 34, pp. 13569-13573.
Mizushima, E. et al., "Au(I)-Catalyzed Highly Efficient Intermolecular Hydroamination of Alkynes," *Organic Letters*, 2003, vol. 5, No. 18, pp. 3349-3352.
Vicente, J. et al., "Recent Advances in the Chemistry of Gold(I) Complexes with C-, N- and S-Donor Ligands Part I: Alkynyl. Amino, Imino and Nitrido Derivatives," *Gold Bulletin*, 1998, vol. 31, No. 3, pp. 83-87.

* cited by examiner

*Primary Examiner* — Shawquia Young
(74) *Attorney, Agent, or Firm* — Kilpatrick Townsend & Stockton LLP

(57) ABSTRACT

Methods are provided for the catalytic hydroamination of compounds having an alkyne or allene functional group, in which the compound is contacted with ammonia or an amine in the presence of a catalytic amount of a gold complex under conditions sufficient for hydroamination to occur.

17 Claims, 13 Drawing Sheets

FIGURE 5

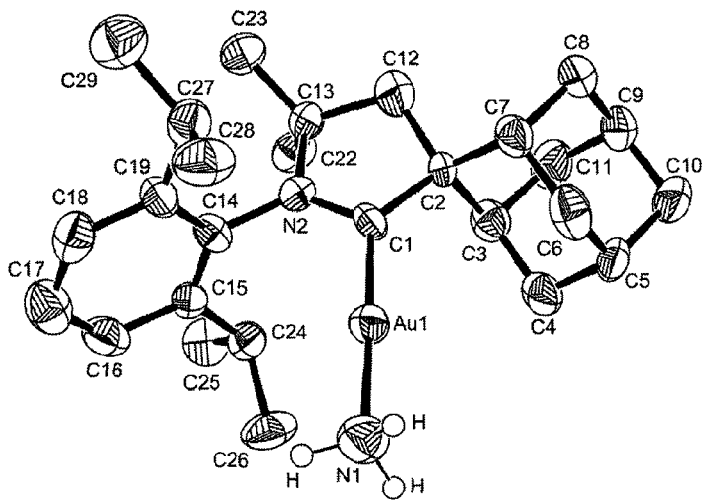

| | |
|---|---|
| Empirical formula | [C$_{27}$H$_{41}$AuN$_2$][B(C$_6$F$_5$)$_4$], CH$_2$Cl$_2$ |
| Formula weight | 1390.01 |
| Temperature | 180(2) K |
| Wavelength | 0.71073 Å |
| Crystal system | Orthorhombic |
| Space group | Pbca |
| Unit cell dimensions | a = 20.470(14) Å  α= 90° |
| | b = 18.048(13) Å  β= 90° |
| | c = 28.94(2) Å  γ = 90° |
| Volume | 10692(13) Å$^3$ |
| Z | 8 |
| Density (calculated) | 1.727 Mg/m$^3$ |
| Absorption coefficient | 3.010 mm$^{-1}$ |
| F(000) | 5472 |
| Crystal size | 0.32 x 0.09 x 0.07 mm$^3$ |
| Theta range for data collection | 1.66 to 22.46° |
| Index ranges | -22<=h<=21, -19<=k<=19, -30<=l<=31 |
| Reflections collected | 44237 |
| Independent reflections | 6954 [R(int) = 0.1383] |
| Completeness to theta = 22.46° | 99.9 % |
| Absorption correction | Sadabs |
| Max. and min. transmission | 0.8169 and 0.4459 |
| Refinement method | Full-matrix least-squares on F$^2$ |
| Data / restraints / parameters | 6954 / 114 / 756 |
| Goodness-of-fit on F$^2$ | 1.029 |
| Final R indices [I>2sigma(I)] | R1 = 0.0496, wR2 = 0.1018 |
| R indices (all data) | R1 = 0.0929, wR2 = 0.1203 |
| Extinction coefficient | 0.00009(3) |
| Largest diff. peak and hole | 0.832 and -0.692 e.Å$^{-3}$ |

FIGURE 6

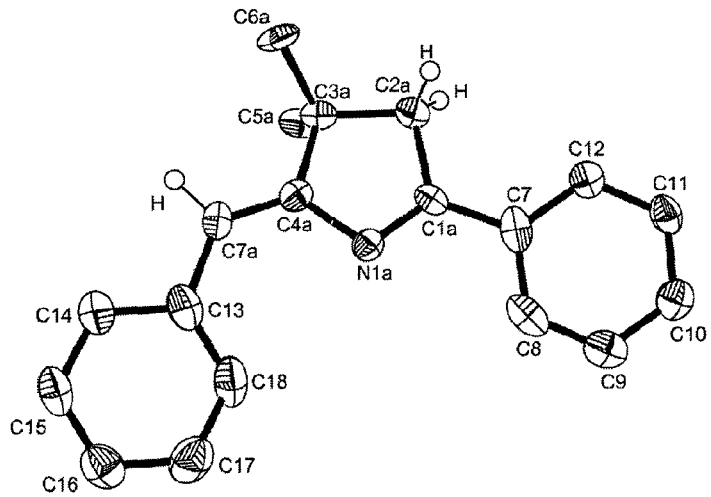

| | |
|---|---|
| Empirical formula | $C_{19}H_{19}N$ |
| Formula weight | 261.35 |
| Temperature | 100(2) K |
| Wavelength | 0.71073 Å |
| Crystal system | Monoclinic |
| Space group | P2(1)/n |
| Unit cell dimensions | a = 5.9369(19) Å    α= 90° |
| | b = 8.234(3) Å    β= 90.836(5)° |
| | c = 29.758(9) Å    γ = 90° |
| Volume | 1454.5(8) Å$^3$ |
| Z | 4 |
| Density (calculated) | 1.193 Mg/m$^3$ |
| Absorption coefficient | 0.069 mm$^{-1}$ |
| F(000) | 560 |
| Crystal size | 0.28 x 0.20 x 0.17 mm$^3$ |
| Theta range for data collection | 2.57 to 28.35° |
| Index ranges | -7<=h<=7, -9<=k<=9, -39<=l<=17 |
| Reflections collected | 6240 |
| Independent reflections | 3182 [R(int) = 0.0384] |
| Completeness to theta = 28.35° | 87.7 % |
| Absorption correction | Sadabs |
| Max. and min. transmission | 0.9884 and 0.9810 |
| Refinement method | Full-matrix least-squares on F$^2$ |
| Data / restraints / parameters | 3182 / 2 / 260 |
| Goodness-of-fit on F$^2$ | 1.065 |
| Final R indices [I>2sigma(I)] | R1 = 0.0554, wR2 = 0.1185 |
| R indices (all data) | R1 = 0.0827, wR2 = 0.1338 |
| Extinction coefficient | 0.0056(17) |
| Largest diff. peak and hole | 0.259 and -0.241 e.Å$^{-3}$ |

FIGURE 7.

| | | | | | | |
|---|---|---|---|---|---|---|
| MesNH$_2$ | $^t$BuNH$_2$ | Ph$_2$NH | PhMeNH | (tetrahydroisoquinoline) | | Et$_2$NH |
| 1 | 2 | 3 | 4 | 5 | | 6 |

| | | |
|---|---|---|
| Ph—≡—H | Ph—≡—Ph | Ph—≡— |
| a | b | c |
| Et—≡—Et | $^t$Bu—≡—H | Cy—≡—H |
| d | e | f |

| Entry | Amine | Alkyne | T (°C) | t (h) | product | yield[b] |
|---|---|---|---|---|---|---|
| 1 | 1 | a | 40 | 16 | Mes–N=C(Ph)(Me) | 81 |
| 2 | 1 | b | 90 | 12 | Mes–N=C(Ph)(CH$_2$Ph) | 86 |
| 3 | 1 | c | 120 | 16 | Mes~N=C(Me)(CH$_2$Ph) 85% E/Z: 5 / Mes–N=C(Ph)(Et) 15% | 93 |
| 4 | 1 | d | 140 | 12 | Mes~N=C($^n$Pr)(Et) E/Z: 1 | 84 |
| 5 | 1 | e | 100 | 10 | Mes–N=C($^t$Bu)(Me) 75% / Mes–N=CH(CH$_2$$^t$Bu) 25% | 94 |
| 6 | 1 | f | 90 | 24 | Mes–N=C(Cy)(Me) | 82 |
| 7 | 2 | d | 140 | 12 | $^t$Bu~N=C($^n$Pr)(Et) E/Z: 1.2 | 81 |

[a] A (5 mol%), amine (0.5 mmol), alkyne (0.5 mmol), C$_6$D$_6$ (0.4 mL). [b] Yields are determined by $^1$H NMR using benzylmethyl ether as an internal standard.

FIGURE 8.

| Entry | Amine | Alkyne | T (°C) | t (h) | product | yield[b] |
|---|---|---|---|---|---|---|
| 1 | 3 | a | 80 | 7 | Ph₂N–C(Ph)=CH₂ | 95 |
| 2 | 3 | c | 120 | 16 | Ph₂N–C(=CHPh)– (E/Z: 1.2) | 48 |
| 3 | 4 | a | 70 | 8 | PhMeN–C(Ph)=CH₂ | 70 |
| 4 | 4 | b | 120 | 16 | PhMeN–C(Ph)=CHPh | 98 |
| 5 | 4 | c | 120 | 16 | PhMeN–C(=CHPh)– 80% (E/Z: 1.6); PhMeN–C(Ph)=CH– 20% | 98 |
| 6 | 4 | d | 120 | 16 | PhMeN–C(Et)=CHEt 21%; PhMeN–C(nPr)=CH– 79% | 86 |
| 7 | 5 | a | 60 | 12 | C₅N–C(Ph)=CH₂ | 46 |
| 8 | 5 | b | 90 | 24 | C₅N–C(Ph)=CHPh | 96 |
| 9 | 5 | c | 120 | 16 | C₅N–C(=CHPh)– 48%; C₅N–C(Ph)=CH– 52% | 67 |
| 10 | 5 | d | 110 | 20 | C₅N–C(Et)=CHEt 42%; C₅N–C(nPr)=CH– 58% | 85 |
| 11 | 6 | a | 100 | 12 | Et₂N–C(Ph)=CH₂ | 23 |
| 12 | 6 | b | 90 | 20 | Et₂N–C(Ph)=CHPh | 98 |
| 13 | 6 | c | 120 | 20 | Et₂N–C(=CHPh)– 57%; Et₂N–C(Ph)=CH– 43% | 89 |
| 14 | 6 | d | 110 | 16 | Et₂N–C(Et)=CHEt 43%; Et₂N–C(nPr)=CH– 57% | 94 |

[a] A (5 mol%), amine (0.5 mmol), alkyne (0.5 mmol), $C_6D_6$ (0.4 mL). [b] Yields are determined by $^1$H NMR using benzylmethyl ether as an internal standard. See Figure 7 for amines 3-6 and alkynes a, b, c and d.

| amine | yield 8a (%) |
|---|---|
| $^iPr_2NH$ | 26 |
| PhMeNH | <5 |
| MesMeNH | 22 |
| Me(PhCH$_2$)NH | 59 |
| (PhCH$_2$)$_2$NH  7 | 61 |
| 5 | 89 |

See Figure 7 for amine 5.

| R | 8 (%) | 9 (%) | yield (%) |
|---|---|---|---|
| $^tBu$ | 100 | 0 | 89 |
| Me$_3$Si | 100 | 0 | 47 |
| $^nBu$ | 0 | 100 | 68 |
| $^cHex$ | 14 | 86 | 79 |

See Figure 7 for amine 5.

| Entry | Amine | R¹ | R² | R⁴ | 10 (%) | 11 (%) | yield[a] |
|---|---|---|---|---|---|---|---|
| 1 | 7 | Et | Et | tBu | 100 | 0 | 83 |
| 2 | 5 | Et | Et | nBu | 100 | 0 | 95 |
| 3 | 5 | Et | Et | cHex | 100 | 0 | 82 |
| 4 | 5 | Et | Et | Ph | 100 | 0 | 73 |
| 5 | 7 | Ph | Me | tBu | 57 | 43 | 61 |
| 6 | 7 | Ph | Me | nBu | 65 | 35 | 64 |
| 7 | 7 | Ph | Me | cHex | 60 | 40 | 59 |

[a] Yields are determined, based on the amine, by ¹H NMR using benzylmethyl ether as an internal standard. See Figure 7 for amines 5 and 7.

FIGURE 12.

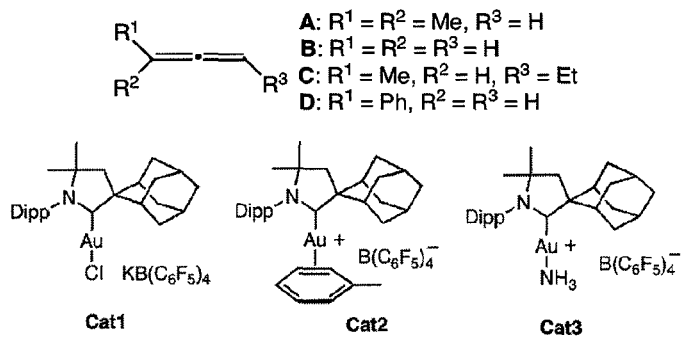

A: R¹ = R² = Me, R³ = H
B: R¹ = R² = R³ = H
C: R¹ = Me, R² = H, R³ = Et
D: R¹ = Ph, R² = R³ = H

| Entry | Amine | Allene | T [°C] | Time[h] | Product | Yield[b] |
|---|---|---|---|---|---|---|
| 1 | PhNH₂ | A | 70 | 12 | (60% branched / 40% linear N-Ph) | 95[c] |
| 2 | MesNH₂ | A | 100 | 5 | prenyl-NHMes | 74 |
| 3 | tBuNH₂ | A | 150 | 30 | prenyl-NHtBu | 54 |
| 4 | PhMeNH | A | 70 | 12 | prenyl-N(Me)Ph | 98 |
| 5 | p-Cl-C₆H₄MeNH | A | 70 | 12 | prenyl-N(Me)(p-Cl-Ph) | 97 |
| 6 | p-MeO-C₆H₄MeNH | A | 70 | 12 | prenyl-N(Me)(p-MeO-Ph) | 97 |
| 7 | tetrahydroquinoline | A | 70 | 9 | N-prenyl tetrahydroquinoline | 99 |
| 8 | indoline | A | 70 | 3 | N-prenyl indoline | 99 |
| 9 | indoline | B | 70 | 3 | N-allyl indoline | 87[d] |
| 10 | PhMeNH | C | 80 | 10 | (35% / 65% regioisomers) | 98[e] |

[a] Cat1 (5 mol%), amine (0.5 mmol), allene (0.5 mmol), C₆D₆ (0.4 mL). [b] Yields are determined by ¹H NMR using benzylmethyl ether as an internal standard. [c] Yield based on allene. [d] Excess allene was used. [e] Slight excess amine was used, yield based on allene.

FIGURE 13.

| Entry | Amine | Allene | T [°C] | Time[h] | Product | Yield[b] |
|---|---|---|---|---|---|---|
| 1 | morpholine | A | 100 | 12 | (CH₃)₂C=CH-CH₂-N(morpholine) | 92 |
| 2 | morpholine | B | 100 | 12 | CH₂=CH-CH₂-N(morpholine) | 89[c] |
| 3 | morpholine | C | 120 | 6 | Et-CH=CH-CH(morpholine) 70% / CH₃-CH=CH-CH(Et)(morpholine) 30% | 89[d] |
| 4 | morpholine | D | 130 | 24 | Ph-CH=CH-CH₂-N(morpholine) | 66[e] |
| 5 | (PhCH₂)₂NH | A | 80 | 12 | (CH₃)₂C=CH-CH₂-N(CH₂Ph)₂ | 99 |
| 6 | (PhCH₂)₂NH | B | 70 | 12 | CH₂=CH-CH₂-N(CH₂Ph)₂ | 94[c] |
| 7 | tetrahydroisoquinoline (NH) | A | 90 | 12 | (CH₃)₂C=CH-CH₂-N(tetrahydroisoquinoline) | 98 |
| 8 | tetrahydroisoquinoline (NH) | B | 90 | 8 | CH₂=CH-CH₂-N(tetrahydroisoquinoline) | 93[c] |
| 9 | Et₂NH | A | 130 | 36 | (CH₃)₂C=CH-CH₂-NEt₂ | 98 |
| 10 | Et₂NH | B | 150 | 24 | CH₂=CH-CH₂-NEt₂ | 82[c] |
| 11 | Et₂NH | D | 165 | 24 | Ph-CH=CH-CH₂-NEt₂ | 61[e] |

[a] Cat1 (5 mol%), amine (0.5 mmol), allene (0.5 mmol), C₆D₆ (0.4 mL). [b] Yields are determined by ¹H NMR using benzylmethyl ether as an internal standard. [c] Excess allene was used, yield based on amine. [d] Slight excess amine was used, yield based on allene. [e] Two equivalents of allene was used, yield based on amine. See Figure 12 for Allenes A, B, C and D, as well as catalyst Cat1.

<sup>a</sup> Reagents and conditions: i) ArNH₂, molecular sieves, toluene, 100 °C, 16 h, 94%; ii) LDA, Et₂O, -78 °C to rt, 3 h, then 3-chloro-2-methyl-1-propene, -78 °C to rt, 2 h, 90%; iii) HCl (2.1 eqs), toluene, 110 °C, 16 h, 74%; iv) LDA, Et₂O, -78 °C to rt, 2 h, 95%; v) AuCl(SMe₂), THF, rt, 12h, 87%.

FIGURE 15.
| Alkyne | L | T (°C) | t (h) | Products | | Yield[b] (%) |
|---|---|---|---|---|---|---|
| 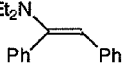 PhCCPh 8a | 1a | 90 | 20 | | | 98 |
| | 1d | 90 | 20 | | | 92 |
| EtCCEt 8b | 1a | 110 | 16 | 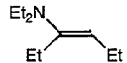 43% | 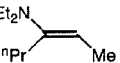 57% | 94 |
| | 1d | 110 | 20 | 39% | 61% | 93 |
| PhCCMe 8c | 1a | 120 | 20 | 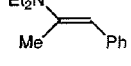 57% | 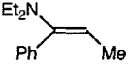 43% | 89 |
| | 1d | 120 | 20 | 52% | 48% | 92 |
[a] (L)AuCl complex (5 mol%), KB(C$_6$F$_5$)$_4$ (5 mol%), Et$_2$NH (0.5 mmol), alkyne (0.5 mmol), C$_6$D$_6$ (0.4 mL). [b] Yields are determined by $^1$H NMR using benzylmethyl ether as an internal standard. See Figure 14 for ligands L 1a and 1d.

FIGURE 16.

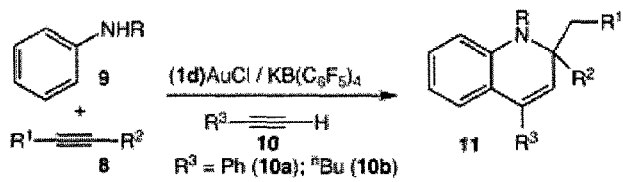

| Amine | Internal alkyne | Terminal alkyne | Products | | Yield[b] % |
|---|---|---|---|---|---|
| PhNHMe 9a | 8b | 10a | (Me,N Et, nPr, R³) | R³ = Ph, 11a | 70 |
| | | 10b | | R³ = nBu, 11b | 77 |
| 9a | 8c | 10a | (Me,N Me, Bz, R³) | R³ = Ph, 11c | 83 |
| | | 10b | | R³ = nBu, 11d | 71 |
| pClPhNHMe 9b | 8b | 10b | (Cl, Me,N R¹, R², nBu) | R¹ = Et, R² = nPr, 11e | 68 |
| | 8c | 10b | | R¹ = Me, R² = Bz, 11f | 79[c] |
| pMeOPhNHMe 9c | 8b | 10b | (MeO, Me,N R¹, R², nBu) | R¹ = Et, R² = nPr, 11g | 77 |
| | 8c | 10b | | R¹ = Me, R² = Bz, 11h | 61[c] |
| 9d (tetrahydroquinoline) | 8b | 10a | (R³, Et, nPr, fused) | R³ = Ph, 11i | 76 |
| | | 10b | | R³ = nBu, 11j | 65[c] |
| 9d | 8c | 10a | (R³, Me, Bz, fused) | R³ = Ph, 11k | 53[c] |
| | | 10b | | R³ = nBu, 11l | 56[c] |
| 9e (indoline) | 8b | 10a | (R³, Et, nPr, fused) | R³ = Ph, 11m | 66[d] |
| | | 10b | | R³ = nBu, 11n | 73[d] |

[a] 2d complex (see Figure 14) (5 mol%), KB($C_6F_5$)$_4$ (5 mol%), aryl amine 9 (0.5 mmol), internal alkyne 8 (0.55 mmol), $C_6D_6$ (0.4 mL). Reaction mixture heated at 120 °C till amine was completely consumed. Terminal alkyne 10 (0.5 mmol), 100 °C, 24 h. [b] Yields are based on arylamine 9, and determined by $^1$H NMR using benzylmethyl ether as an internal standard. [c] Hydroamination step at 100 °C. [d] Hydroamination step at 88 °C.

GOLD CATALYZED HYDROAMINATION OF ALKYNES AND ALLENES

CROSS-REFERENCES TO RELATED APPLICATIONS

This application claims priority to U.S. Provisional Application No. 61/051,826, filed May 9, 2008, incorporated in its entirety herein.

STATEMENT AS TO RIGHTS TO INVENTIONS MADE UNDER FEDERALLY SPONSORED RESEARCH AND DEVELOPMENT

This invention was made with Government support under Grant No. GM 068825, awarded by the National Institutes of Health. The Government has certain rights in this invention.

BACKGROUND OF THE INVENTION

Nitrogen-carbon bonds are ubiquitous in products ranging from chemical feedstock to pharmaceuticals. Since ammonia is among the largest volume and least expensive bulk chemicals, one of the greatest challenges of synthetic chemistry is to find atom efficient processes capable of combining $NH_3$ with simple organic molecules to create nitrogen-carbon bonds. Transition metal complexes can readily render a variety of N—H bonds, including those of primary and secondary amines, reactive enough to undergo functionalization. However, apart from a few exceptions, ((E. G. Bryan, B. F. G. Johnson, K. Lewis, *J. Chem. Soc., Dalton Trans.* 1977, 1328-1330; G. L. Hillhouse, J. E. Bercaw, *J. Am. Chem. Soc.* 1984, 106, 5472-5478; A. L. Casalnuovo, J. C. Calabrese, D. Milstein, *Inorg. Chem.* 1987, 26, 971-973; M. M. B. Holl, P. T. Wolczanski, G. D. Van Duyne, *J. Am. Chem. Soc.* 1990, 112, 7989-7994; J. Zhao, A. S. Goldman, J. F. Hartwig, *Science* 2005, 307, 1080-1082; Y. Nakajima, H. Kameo, H. Suzuki, *Angew. Chem.* 2006, 118, 964-966; *Angew. Chem. Int. Ed.* 2006, 45, 950-952. A non-metallic system has recently been reported to cleave $NH_3$ under mild experimental conditions: G. D. Frey, V. Lavallo, B. Donnadieu, W. W. Schoeller, G. Bertrand, *Science* 2007, 316, 439-441; A. L. Kenward, W. E. Piers, *Angew. Chem.* 2008, 120, 38-42; *Angew. Chem. Int. Ed.* 2008, 47, 38-41; and J. M. Lynam, *Angew. Chem.* 2008, 120, 831-833; *Angew. Chem. Int. Ed.* 2008, 47, 843-845)) metals usually react with ammonia to afford supposedly inert Lewis acid-base complexes, as first recognized in the late 19th century by Werner (A. Werner, *Z. Anorg. Chem.* 1893, 3, 267). Consequently, the catalytic functionalization of $NH_3$ has remained elusive until the recent discovery by Hartwig (Q. Shen, J. F. Hartwig, *J. Am. Chem. Soc.* 2006, 128, 10028-10029) and Buchwald (D. S. Surry, S. L. Buchwald, *J. Am. Chem. Soc.* 2007, 129, 10354-10355) of the palladium catalyzed coupling of aryl halides with ammonia in the presence of a stoichiometric amount of base. An even more appealing process would be the addition of $NH_3$ to carbon-carbon multiple bonds, a process that ideally occurs with 100% atom economy (R. Severin, S. Doye, *Chem. Soc. Rev.* 2007, 36, 1407-1420; S. Matsunaga, *J. Synth. Org. Chem. Japan* 2006, 64, 778-779; K. C. Hultzsch, *Adv. Synth. Catal.* 2005, 347, 367-391; M. Beller, J. Seayad, A. Tillack, H. Jiao, *Angew. Chem.* 2004, 116, 3448-3479; *Angew. Chem. Int. Ed.* 2004, 43, 3368-3398; F. Alonso, I. P. Beletskaya, M. Yus, *Chem. Rev.* 2004, 104, 3079-3159; P. W. Roesky, T. E. Müller, *Angew. Chem.* 2003, 115, 2812-2814; *Angew. Chem. Int. Ed.* 2003, 42, 2708-2710; F. Pohlki, S. Doye, *Chem. Soc. Rev.* 2003, 32, 104-114; T. E. Mailer, M. Beller, *Chem. Rev.* 1998, 98, 675-703).

Although, various catalysts have been used to effect the so-called hydroamination reaction, which include alkali metals, ((C. G. Hartung, C. Breindl, A. Tillack, M. Beller, *Tetrahedron* 2000, 56, 5157-5162; P. Horrillo-Martinez, K. C. Hultzsch, A. Gil, V. Branchadell, *Eur. J. Org. Chem.* 2007, 3311-3325; S. Datta, M. T. Gamer, P. W. Roesky, *Organometallics* 2008, 27, 1207-1213); early transition metals (P. W. Roesky, *Z. Anorg. Allg. Chem.* 2006, 632, 1918-1926; A. L. Odom, *Dalton Trans.* 2005, 225-233; N. Hazari, P. Mountford, *Acc. Chem. Res.* 2005, 38, 839-849; I. Bytschkov, S. Doye, *Eur. J. Org. Chem.* 2003, 935-946; E. Smolensky, M. Kapon, M. S. Eisen, *Organometallics* 2007, 26, 4510-4527; M. Dochnahl, K. Löhnwitz, J.-W. Pissarek, M. Biyikal, S. R. Schulz, S. Schön, N. Meyer, P. W. Roesky, S. Blechert, *Chem. Eur. J.* 2007, 13, 6654-6666); late transition metals (J. Zhang, C.-G. Yang, C. He, *J. Am. Chem. Soc.* 2006, 128, 1798-1799; K. Komeyama, T. Morimoto, K. Takaki, *Angew. Chem.* 2006, 118, 3004-3007; *Angew. Chem. Int. Ed.* 2006, 45, 2938-2941; F. E. Michael, B. M. Cochran, *J. Am. Chem. Soc.* 2006, 128, 4246-4247; A. M. John, N. Sakai, A. Ridder, J. F. Hartwig, *J. Am. Chem. Soc.* 2006, 128, 9306-9307; A. Takemiya, J. F. Hartwig, *J. Am. Chem. Soc.* 2006, 128, 6042-6043; A. R. Chianese, S. J. Lee, M. R. Gagné, *Angew. Chem.* 2007, 119, 4118-4136; *Angew. Chem. Int. Ed.* 2007, 46, 4042-4059; G. Kovács, G. Ujaque, A. Lledós, *J. Am. Chem. Soc.* 2008, 130, 853-864); d-block elements (N. Meyer, K. Lohnwitz, A. Zulys, P. W. Roesky, M. Dochnahl, S. Blechert, *Organometallics* 2006, 25, 3730-3734; X. Y. Liu, C. H. Li, C. M. Che, *Org. Lett.* 2006, 8, 2707-2710; A. Zulys, M. Dochnahl, D. Hohmann, K. Lohnwitz, J. S. Hellmann, P. W. Roesky, S. Blechert, *Angew. Chem.* 2005, 117, 7972-7976; *Angew. Chem. Int. Ed.* 2005, 44, 7794-7798) and f-block elements, (D. V. Gribkov, K. C. Hultzsch, F. Hampel, *J. Am. Chem. Soc.* 2006, 128, 3748-3759; D. Riegert, J. Collin, A. Meddour, E. Schulz, A. Trifonov, *J. Org. Chem.* 2006, 71, 2514-2517; E. Arnea, M. S. Eisen, *Coord. Chem. Rev.* 2006, 250, 855-859; S. Hong, T. J. Marks, *Acc. Chem. Res.* 2004, 37, 673-686; T. Andrea, M. S. Eisen, *Chem. Soc. Rev.* 2008, 37, 550-567; I. Aillaud, J. Collin, J. Hannedouche, E. Schulz, *Dalton Trans.* 2007, 5105-5118; M. Rastätter, A. Zulys, P. W. Roesky, *Chem. Eur. J.* 2007, 13, 3606-3616) none are effective for the hydroamination of alkynes and allenes when $NH_3$ is used as the amine partner.

Despite recent advances, there still remains a need for an atom-efficient process capable of combining abundant $NH_3$ and amines with simple organic molecules to create nitrogen-carbon bonds as well as allenes. The present invention fulfills this and other needs.

BRIEF DESCRIPTION OF THE INVENTION

The present invention provides methods for the catalytic hydroamination of compounds having an alkyne or allene functional group, in which the compound is contacted with ammonia in the presence of a catalytic amount of a gold complex under conditions sufficient for hydroamination to occur. In some embodiments initial hydroamination is followed by intramolecular cyclization to form nitrogen heterocycles.

Another aspect of the present invention provides gold complexes having the general structure:

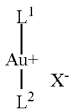

wherein each of $L^1$ and $L^2$ is independently a L ligand.

BRIEF DESCRIPTION OF THE DRAWINGS

FIG. 5 provides an ORTEP representation of complex E and crystal data and structure refinement for complex E.

FIG. 6 provides an ORTEP representation of compound 6f and crystal data and structure refinement for 6f.

FIG. 7 provides a table of hydroamination of alkynes a-f with primary amines 1 and 2 using catalyst A.

FIG. 8 provides a table of hydroamination of alkynes a-f with primary amines 3-6 using catalyst A.

FIG. 12 provides a table for the hydroamination of allenes with primary amines and secondary (alkyl)(aryl)amines.

FIG. 13 provides a table for the hydroamination of allenes with secondary alkylamines.

FIG. 14a provides the structure of ligand 1a. FIG. 14b provides the structure of ligand 1d and catalyst 2d.

FIG. 15 provides a table for the hydroamination of internal alkynes with diethylamine using a gold catalyst having ligand 1a or 1d.

FIG. 16 provides a scheme for the preparation of dihydroisoquinolines by hydroamination of alkynes with an aniline functional group, and a table showing the three-component reactions to prepare the dihydroisoquinolines.

DETAILED DESCRIPTION OF THE INVENTION

I. General

Figure 1:
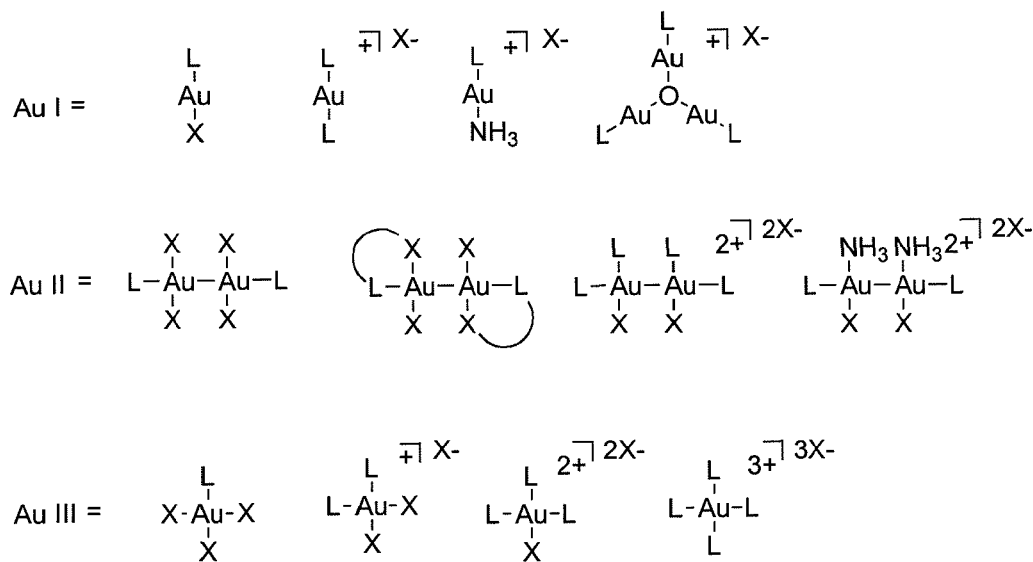
FIG. 1 provides an illustration of the suitable types of gold complexes, X and L are ligands. X and L could be linked to one or two other X or L ligands to form a bidentate or tridentate ligand.

The present invention describes gold-catalyzed addition of ammonia and amines to a variety of unactivated alkynes and allenes, which allows for the formation of a diverse array of linear and cyclic nitrogen containing derivatives. These reactions are useful in a variety of chemical processes due to the ease and economical method of ammonia and amine insertion. These reactions present new synthetic routes to complex chemicals, and have the further advantage of reducing the total number of steps in an amination process, thereby increasing yields and decreasing costs.

II. Abbreviations and Definitions

Abbreviations used herein have their common and accepted meanings to one of skill in the art. Examples of the abbreviations are tBu, tertiary butyl; Me, methyl; THF, tetrahydrofuran; cod, cyclooctadiene; Dipp, 2,6-diisopropylphenyl; and Mes, mesityl. L ligands are any two to four electron donors, which can be neutral or featuring a positive or negative charge in a remote location; X ligands can be covalently bonded to gold or anionic species.

In the present description the term "alkyl", alone or in combination, refers to a straight-chain or branched-chain alkyl group having the indicated number of carbon atoms. For example, $C_{1-10}$ alkyl refers to an alkyl group having from one to ten carbon atoms with the remaining valences occupied by hydrogen atoms. Preferred alkyl groups are those with 1 to 8 carbon atoms, more preferably a straight or branched-chain alkyl group with 1 to 6 carbon atoms and particularly preferred are straight or branched-chain alkyl groups with 1 to 4 carbon atoms. Examples of straight-chain and branched $C_{1-10}$ alkyl groups are methyl, ethyl, propyl, isopropyl, butyl, isobutyl, tert-butyl, the isomeric pentyls, the isomeric hexyls, the isomeric heptyls and the like.

The term "cycloalkyl", alone or in combination, refers to a cyclic alkyl group having 3 to 8 carbon atoms as ring vertices. Preferred cycloalkyl groups are those having 3 to 6 carbon atoms. Examples of $C_{3-8}$ cycloalkyl are cyclopropyl, methylcyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl.

The term "alkoxy", alone or in combination, signifies a group of the formula alkyl-O— in which the teiin "alkyl" has the previously given definition. Examples of alkoxy group include methoxy, ethoxy, n-propoxy, isopropoxy, n-butoxy, isobutoxy, sec-butoxy and tert-butoxy. Preferred alkoxy groups are methoxy and ethoxy.

The term "alkenyl", alone or in combination refers to a straight-chain, cyclic or branched hydrocarbon residue comprising at least one olefinic bond and the indicated number of carbon atoms. Preferred alkenyl groups have up to 8, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl, isobutenyl, 1-cyclohexenyl, 1-cyclopentenyl.

The term "alkynyl", alone or in combination refers to a straight-chain or branched hydrocarbon residue having a carbon carbon triple bond and the indicated number of carbon atoms. Preferred alkynyl groups have up to 8, preferably up to 6, particularly preferred up to 4 carbon atoms. Examples of alkynyl groups are ethynyl, 1-propynyl, 1-butynyl and 2-butynyl.

The terms "alkenyloxy" and "alkynyloxy" refer to groups having the formula —O—$R^i$ in which $R^i$ is an alkenyl or alkynyl group, respectively.

The terms "alkylthio," "alkylsulfonyl," "alkylsulfinyl" and "arylsulfonyl" refer to groups having the formula —S—$R^i$— $S(O)_2$—$R^i$, —S(O)—$R^i$ and —S(O)$_2R^j$, respectively, in which $R^i$ is an alkyl group as previously defined and $R^3$ is an aryl group as previously defined.

The term "alkoxycarbonyl" refers to a group having the foil —C(O)O—$R^i$, wherein $R^i$ is an alkyl group as defined above and wherein the total number of carbon atoms refers to the combined alkyl and carbonyl moieties.

The term "aryl" means, unless otherwise stated, a polyunsaturated, typically aromatic, hydrocarbon group which can be a single ring or multiple rings (up to three rings) which are fused together or linked covalently, and which optionally carries one or more substituents, for example, such as halogen, trifluoromethyl, amino, alkyl, alkoxy, alkylcarbonyl, cyano, carbamoyl, alkoxycarbamoyl, methylendioxy, carboxy, alkoxycarbonyl, aminocarbonyl, alkylaminocarbonyl, dialkylaminocarbonyl, hydroxy, nitro and the like. Non-limiting examples of unsubstituted aryl groups include phenyl, naphthyl and biphenyl. Examples of substituted aryl groups include, but are not limited to phenyl, chlorophenyl, trifluoromethylphenyl, chlorofluorophenyl, and aminophenyl.

The term "arylalkyl", alone or in combination, refers to an alkyl group as previously defined in which one hydrogen atom has been replaced by an aryl group as previously defined. Preferred are benzyl and phenylethyl.

The term "heteroalkyl," by itself or in combination with another term, means, unless otherwise stated, a stable straight or branched chain, or combinations thereof, consisting of the stated number of carbon atoms and from one to three heteroatoms selected from the group consisting of O, N, Si, P and S, and wherein the nitrogen, phosphorus and sulfur atoms may optionally be oxidized and the nitrogen heteroatom may optionally be quaternized.

The term "heterocycloalkyl" refers to a cyclic hydrocarbon radical or a combination of a cyclic hydrocarbon radical with a straight or branched chain alkyl group, consisting of the stated number of carbon atoms and from one to three heteroatoms as ring members selected from the group consisting of O, N, Si, P and S, and wherein the nitrogen, phosphorus and sulfur atoms may optionally be oxidized and the nitrogen heteroatom may optionally be quaternized.

The term "heteroaryl", alone or in combination, signifies aromatic 5- to 10-membered heterocycle which contains one or more, preferably one or two hetero atoms selected from nitrogen, oxygen, phosphorus, and sulfur, wherein nitrogen or oxygen are preferred. If desired, it can be substituted on one or more carbon atoms substituents such as halogen, alkyl, alkoxy, cyano, haloalkyl, preferably trifluoromethyl, and heterocyclyl, preferably morpholinyl or pyrrolidinyl, and the like. Examples of heteroaryls include, but are not limited to, pyridinyl or furanyl, methylcarbonylphenyl, methoxyphenyl, methylendioxyphenyl, 1-naphthyl and 2-naphthyl.

The term "aryloxy" and "heteroaryloxy", alone or in combination, signifies a group of the formula aryl-O— and heteroaryl-O—, respectively, in which the terms "aryl" and "heteroaryl" have the significance as provided above, such as phenyloxy, and pyridyloxy, and the like.

The term "arylamino" signifies a group of the formula aryl-NH— or (aryl)$_2$-N—. The term "heteroarylamino" signifies a group of the formula heteroaryl-NH— or (heteroaryl)$_2$-N—, respectively. For "arylamino" and "heteroarylamino" the terms "aryl" and "heteroaryl" have the significance as provided above, such as phenyl, pyridyl, and the like.

The term "amino" signifies a primary, secondary or tertiary amino group that is attached to the remainder of the molecule through the nitrogen atom, with the secondary amino group carrying an alkyl or cycloalkyl substituent and the tertiary amino group carrying two similar or different alkyl or cycloalkyl substituents or the two nitrogen substituents together forming a ring, such as, for example, —NH$_2$, methylamino, ethylamino, dimethylamino, diethylamino, methylethylamino, pyrrolidin-1-yl or piperidino etc., preferably amino, dimethylamino and diethylamino and particularly primary amino.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is meant to include trifluoromethyl, 2,2,2-trifluoroethyl, 4-chlorobutyl, 3-bromopropyl, and the like.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

III. Hydroamination of Allenes and Alkynes with Ammonia

In one aspect, the present invention provides a method for hydroamination, comprising contacting a compound having an alkyne or allene functional group with ammonia in the presence of a catalytic amount of a gold complex under conditions sufficient for hydroamination to occur.

The compounds which are suitable as substrates in the present invention are varied, but have either an alkyne or allene functional group. In some embodiments, dialkynes are present. Depending on the positions of the alkynes (when two are present), internal cyclization can be accomplished to produce a five- to ten-membered nitrogen heterocycle (e.g., pyrrolidine, pyridines, dihydropyridine, pyrrole, and the like). In one group of embodiments, the alkyne compound is a $C_{3-12}$ alkyne. A variety of alkynes are used; for example in one embodiment, a dialkyne, (3,3-dimethylpenta-1,4-diyne-1,5-diyl)dibenzene, is used; while in another embodiment, a much simpler alkyne, 3-hexyne, is used. The alkynes can be terminal alkynes or internal alkynes. Terminal alkynes have a hydrogen at one end of the alkyne. Internal alkynes are those alkynes having a substituent other than hydrogen at both ends of the alkyne.

In another embodiment, hydroamination of allenes with ammonia is carried out in the presence of a gold catalyst. In one group of embodiments, the allene compound is a $C_{3-12}$ allene. This reaction also is carried out with a wide range of allenes; for example in one embodiment, 1,1,3,3-tetraphenyl-propa-1,2-diene, a $C_{27}$ hydrocarbon, is used as the allene; while in another embodiment, the smallest possible allene, 1,2-propadiene, is used.

A variety of gold catalysts are useful in the methods of the present invention. In one embodiment, a Au catalyst with gold in any oxidation state is used. In another embodiment gold nanoparticles/clusters are used as catalysts. In yet another embodiment, a mixture, containing one or more Au compounds and salts of other metals, is used as the catalyst. In yet another embodiment, the gold catalyst is generated in situ. In another embodiment, the gold catalyst is a complex of the form shown in FIG. 1. In some embodiments, L or X ligands are attached, by a linker, to one or two L or X ligands, thereby forming a bidentate or tridentate ligand. X, in some instances, is a charge-balancing anion of a cationic complex. In another preferred embodiment, Au(I) or Au(III) complexes are chosen as catalysts.

Typically suitable L ligands are any two or four electron donating neutral ligands. Sometimes the L ligands also possess a charge at a remote location. In some embodiments each L ligand is independently selected from carbenes, bent-allenes, phosphines, sulfonated phosphines, phosphites, phosphinites, phosphonites, arsines, stibines, ethers, ammonia, amines, amides, sulfoxides, carbonyls, nitrosyls, pyridines or thioethers. Suitable L ligands include those disclosed in U.S. Pat. No. 5,312,940 (Grubbs et al.) and U.S. Pat. No. 5,342,909 (Grubbs et al.).

Numerous ligands can be chosen for the gold complexes to accomplish hydroamination of allenes and alkynes with ammonia. In one embodiment, a carbene ligand is present in the gold complex. And in another embodiment, the gold complex contains a phosphine ligand. In another embodiment a bent-allene is present. Suitable carbene ligands include those described in U.S. Patent Publication No. 2007/0004917 (Bertrand et al.), U.S. Pat. No. 6,492,525 (Bertrand et al.), U.S. Patent Publication No. 2003/0055262 (Grubbs et al.), U.S. Patent Publication No. 2002/0058812 (Grubbs et al.) and U.S. Patent Publication No. 2007/0282148 (Grubbs et al.) and U.S. Non-Provisional application Ser. No. 12/101,100 (Bertrand et al.); suitable carbenes typically inculde N-heterocycle carbenes. Suitable bent allenes include those described in U.S. Provisional Patent Application No. 61/020, 309 (Bertrand et al.). Suitable gold catalysts are also described in V. Lavallo, G. D. Frey, S. Kousar, B. Donnadieu, G. Bertrand, *Proc. Nat. Acad. Sci. USA* 104, 13569 (2007) and also in P. de Fremont, N. M. Scott, E. D. Stevens, S. P. Nolan, *Organometallics* 24, 2411 (2005). Exemplary gold complexes are provided in the examples below.

The reaction mixture typically contains 0.0001 moles-1 mole of the catalyst for every mole (0.01 mole %-100 mole %) of the reacting alkyne or allene. Preferably, 0.0001 moles-0.3 moles of the catalyst is used for every mole (0.01 mole %-30 mole %) of the reacting alkyne or allene. More preferable reaction mixtures have 0.0001 moles-0.15 moles of the catalyst for every mole (0.01 mole %-15 mole %) of the reacting alkyne or allene. In one embodiment, 0.001 moles of the catalyst is used for every mole (0.1 mole %) of the reacting alkyne; while in another embodiment, 0.10 moles (10 mole %) of the catalyst is used for every mole of the reacting alkyne.

Generally, the hydroamination reaction disclosed in the invention can be performed under a wide range of conditions; the solvents, temperature ranges and the amount of catalysts recited herein should not be considered limiting. In general, it is desirable for the reactions to be run using mild conditions which will not adversely affect the reactants, products or the catalysts.

Hydroamination of alkynes and allenes with ammonia can proceed in a wide range of temperatures, for example, from about 0° C. to about 300° C. In one embodiment, hydroamination proceeds at a temperature from about 20° C. to about 280° C. In another embodiment, hydroamination with ammonia is carried out at about 110° C., although, in certain other embodiments, hydroamination with ammonia is carried out by heating at 200° C. In another embodiment, hydroamination with ammonia is at least 50%, 60%, 70%, 80%, 90% or 100% complete after heating at a temperature from about 0° C. to about 300° C. for between about 1 to about 48 hours. In another embodiment, hydroamination with ammonia is at least 50%, 60%, 70%, 80%, 90% or 100% complete after heating at a temperature from about 20° C. to about 280° C. for between about 1 to about 48 hours. In some other embodiments, the reaction is carried out between 20° C. and 110° C. In some embodiments the reaction is also be carried out between 110° C. and 200° C. Whereas in some embodiments, the reaction is carried out between 200° C. and 280° C. Time for sufficient completion of the reaction varies depending on the other reaction conditions. In one embodiment, hydroamination with ammonia is at least 50%, 60%, 70%, 80%, 90% or 100% complete between 1 to 6 hours. In another embodiment, hydroamination with ammonia is at least 50%, 60%, 70%, 80%, 90% or 100% complete between 6 to 24 hours. In yet another embodiment, hydroamination with ammonia is at least 50%, 60%, 70%, 80%, 90% or 100% complete between 1 and 3 days.

Additionally, reactions of the inventive method are generally carried out in a liquid reaction medium. For those reactions conducted in solvent, an inert solvent is preferred, particularly one in which the reaction ingredients are substantially soluble. Typically, the hydroamination reaction is carried out in the presence of at least one solvent, and possibly, in a combination of two or more solvents. Suitable solvents include ethers such as benzyl methyl ether, diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, xylene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents. In certain embodiments, the solvent includes, but is not limited to, acetonitrile, toluene, dimethoxyether, tetrahydrofuran, dioxane, 1,2-dimethoxyethane, bis(2-methoxyethyl)ether, dimethylsulfoxide, dimethylformamide, xylenes, chloroform, dichloromethane, dichloroethane, carbontetrachloride, hexanes, heptane, octane, diethyl ether and combinations thereof. In other embodiments, the solvent includes acetonitrile or toluene. Solventless conditions can also be used.

The reaction processes of the present invention can be conducted in continuous, semi-continuous or batch fashion and may involve a liquid recycle operation as desired. The processes of this invention are preferably conducted in batch fashion. Likewise, the manner or order of addition of the reaction ingredients and solvent are also not generally critical to the success of the reaction, and may be accomplished in any conventional fashion.

The reaction can be conducted in a single reaction zone or in a plurality of reaction zones, in series or in parallel or it may be conducted batch wise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batch wise or continuously into the reaction zone during the course of the reaction can be conveniently utilized in the processes especially to maintain the desired molar ratio of the starting materials. The reaction steps may be effected by the incremental addition of one of the starting materials to the other. When complete conversion is not desired or not obtainable, the starting materials can be separated from the product and then recycled back into the reaction zone.

The processes may be conducted in either thick glass, glass lined, stainless steel or similar type reaction equipment (vessel). In one embodiment the reaction is carried out in a sealed NMR tube. The reaction zone may be fitted with one or more internal and/or external heat exchanger(s) in order to control undue temperature fluctuations, or to prevent any possible "runaway" reaction temperatures.

IV. Gold Complexes

In another aspect, the present invention provides a selection of gold complexes that can be used in the methods above. In one preferred embodiment, the gold complex has the structure:

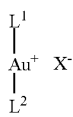

wherein each of L¹ and L² is independently a L ligand.

In another preferred embodiment, the gold complex has an NH₃ ligand, and additionally possesses at least one L ligand. In a more preferred embodiment, the gold complex has the structure:

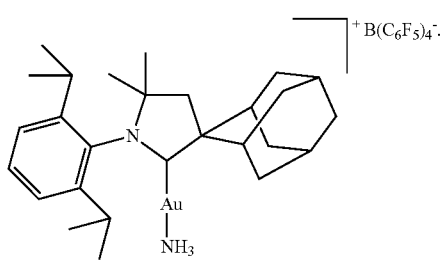

Figure 2:
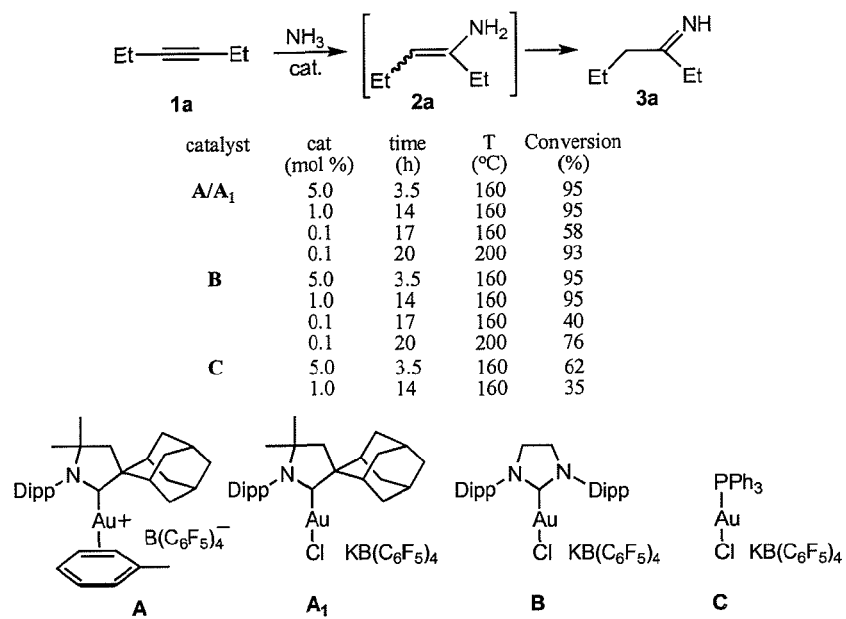
FIG. 2 provides a scheme illustrating the catalytic hydroamination of 3-hexyne with ammonia.

A. Characteristics of Au Catalysts and Compounds Prepared by the Process of Hydroamination of Alkenes and Allenes:

Highly reactive cationic cyclic(alkyl)(amino)carbene (CAAC) gold complex A (described in V. Lavallo, G. D. Frey, S. Kousar, B. Donnadieu, G. Bertrand, *Proc. Nat. Acad. Sci. USA* 104, 13569 (2007)) is used as a catalyst. Excess ammonia is condensed into a sealable NMR tube loaded with 5 mol % A, 3-hexyne and deuterated benzene. Upon heating to 160° C. for 3.5 h, a clean addition of NH₃ was observed, which afforded the primary imine 3a, the expected tautomer of enamine 2a (A, A₁, B, C, 1a, 2a and 3a are shown in FIG. 2). 95% yield was obtained. This experiment was repeated using other conditions; a yield of 95% was also obtained when 1.0 mol % A was used at 160° C. for 14 h. When the amount of catalyst was reduced to 0.1 mol % and the reaction carried out for 17 h at 160° C., 58% of the yield was obtained; the yield, however, improved to 93% when the temperature was raised to 200° C. and the reaction carried out for 20 h.

Identical catalytic results were obtained when hydroamination of 3-hexyne with ammonia is carried in the presence of an equimolar mixture of (CAAC)AuCl/KB(C₆F₅)₄ (A₁). The results are shown in FIG. 2.

In another experiment to evaluate the effect of the CAAC ligand (V. Lavallo, Y. Canac, C. Praesang, B. Donnadieu, G. Bertrand, *Angew. Chem. Int. Ed.* 44, 5705 (2005)), (NHC) AuCl/KB(C₆F₅)₄ B (P. de Fremont, N. M. Scott, E. D. Stevens, S. P. Nolan, *Organometallics* 24, 2411 (2005)) and (Ph₃P)AuCl/KB(C₆F₅)₄ C were used as catalysts under the same experimental conditions. With the NHC supported catalyst B comparable results were observed, although with a low catalyst loading (0.1 mol %) the CAAC based catalyst A/A₁ appeared more efficient. Interestingly, even C with a triphenylphosphine ligand catalyzed, at least to some extent, the hydroamination reaction.

When related silver complex (CAAC)AgCl/KB(C₆F₅)₄, and [NH₄][B(C₆F₅)₄] were used independently as catalysts no reactions were observed, showing the importance of gold, and ruling out a Brønsted acid mediated reaction. A few examples of acid-catalyzed hydroaminations (excluding NH₃) have been reported in D. C. Rosenfeld, S. Shekhar, A. Takemiya, M. Utsunomiya, J. F. Hartwig, *Org. Lett.* 8, 4179 (2006) and L. L. Anderson, J. Arnold, R. G. Bergman, *J. Am. Chem. Soc.* 127, 14542 (2005).

Since AuCl, AuCl/KB(C₆F₅)₄, and even (CAAC)AuCl do not induce the hydroamination, it is clear that in order for the gold center to catalyze the addition of NH₃, it must be coordinated by an L ligand and rendered cationic by Cl abstraction.

In order to gain insight into the catalytic process, other experiments were performed. Addition of one equivalent of 3-hexyne 1a or excess NH₃ to complex A instantaneously gave rise to the η²-bound alkyne complex D, or Werner complex E (an ORTEP representation is shown in FIG. 5), respectively. Upon exposure of a benzene solution of D to excess NH₃, 3-hexyne was immediately displaced from the gold center, and the Werner complex E was again isolated in quantitative yield. This result suggests that the NH₃ does not add to the alkyne via an outer sphere mechanism. Importantly, when a benzene solution of complex E was treated at room temperature for 24 hours with a large excess of 3-hexyne, the imine complex F was quantitatively obtained, even when the reaction vessel is open to a glovebox atmosphere. This experiment implies that NH₃ does not dissociate from the metal by a simple ligand exchange with the alkyne. Lastly, addition of excess NH₃ to F liberated the imine 3a and regenerated complex E. The Werner complex E is the resting state of the catalyst, and it exhibits identical catalytic activity as A/A1.

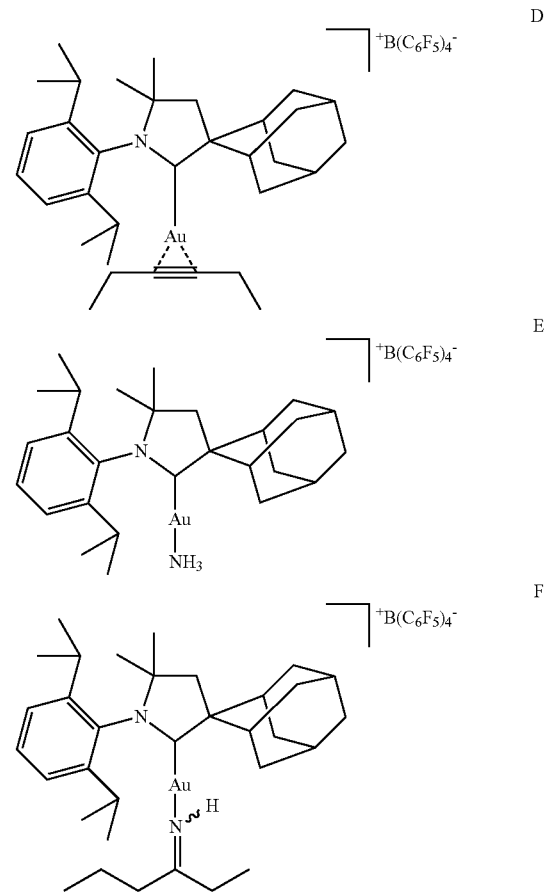

Figure 3:
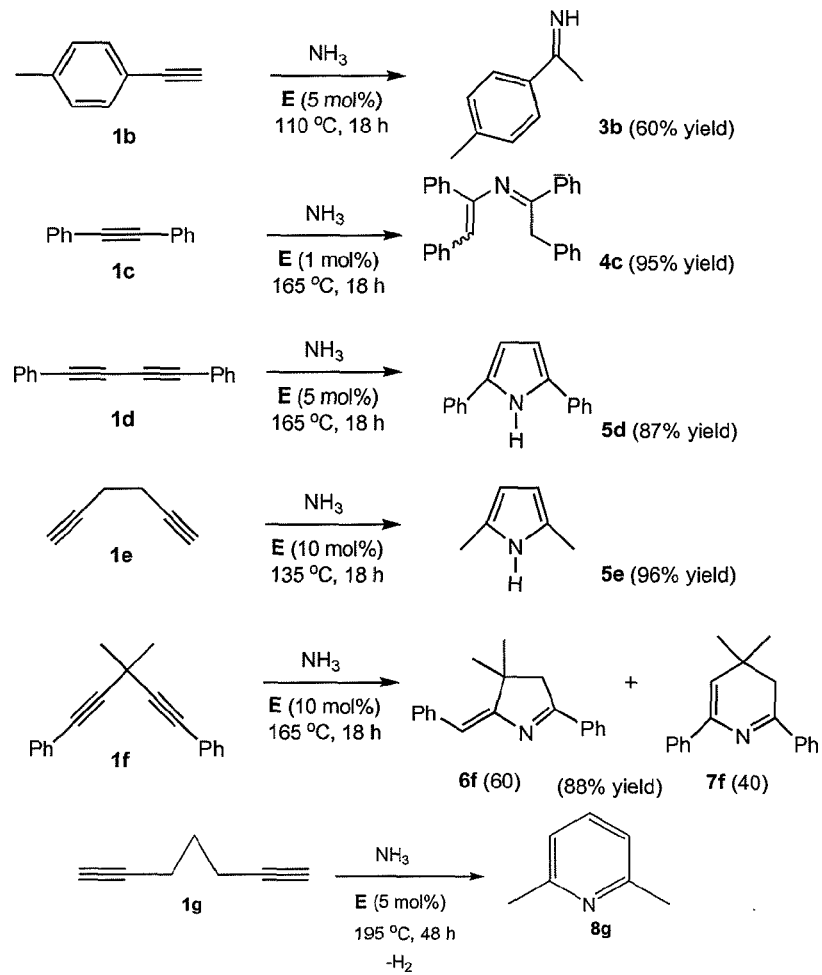
FIG. 3 provides examples of catalytic amination of various alkynes with ammonia, including dialkynes in which heterocyclic rings are formed.

FIG. 3 shows a terminal alkyne 1b and a diaryl alkyne 1c that were reacted with NH₃ in the presence of a catalytic amount of the Werner complex E. With 1b the reaction takes place even at 110° C., exclusively affording the Markovnikov imine 3b in 60% yield. When diphenyl acetylene 1c was used, 2-aza-1,3-diene 4c was cleanly formed (95% yield). This product probably results from the addition of ammonia to diphenyl acetylene affording an enamine, which reacts further with a second molecule of alkyne. The difference in the outcome of the reaction with 1c, compared to 1a,b, can be rationalized by the presence of acidic benzylic protons in the imine tautomer, which disfavors the latter versus its enamine tautomer.

Widely occurring in natural products, nitrogen heterocycles are an important class of compounds that often display potent biological activity. Considering the above mentioned results, we attempted the direct synthesis of heterocycles from diynes and $NH_3$. When the 1,4-diphenylbuta-1,3-diyne 1d and hexa-1,5-diyne 1e were used, the corresponding 2,5-disubstituted pyrroles 5d and 5e were produced in 87 and 96% yield, respectively. Both products result from the tandem Markovnikov addition of $NH_3$ and ring-closing hydroamination. Starting from the 1,4-diyne 1f, a 60/40 mixture of five- and six-membered heterocycles 6f and 7f was obtained in 88% yield. The six-membered ring 7f arises from two consecutive Markovnikov hydroamination reactions, whereas the formation of 6f involves an anti-Markovnikov $NH_3$-addition or ring closing step. When a 1,6-diyne 1g is used, a Markovnikov $NH_3$-addition occurs, 8g (2,6-dimethyl-pyridine) is obtained.

Figure 4:
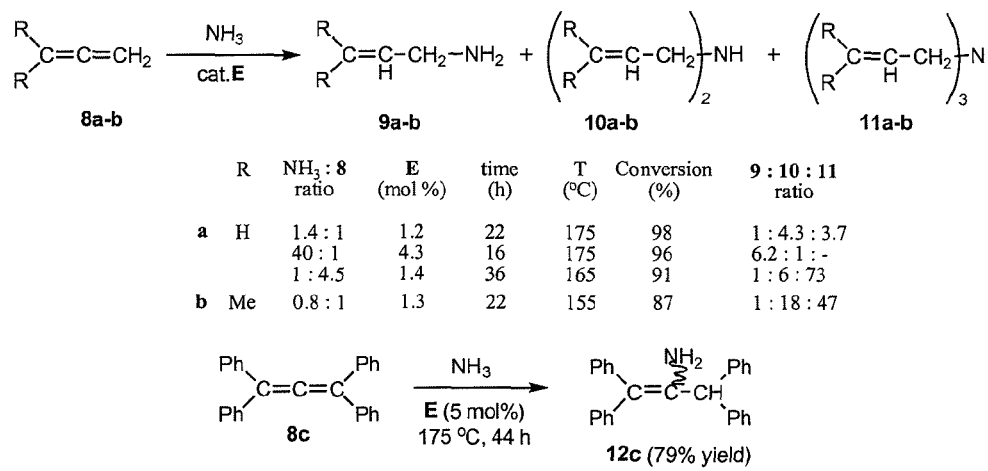
FIG. 4 provides a scheme illustrating the hydroamination of various allenes with ammonia.

To expand the scope of the hydroamination reaction using $NH_3$, allenes were next tested as substrates. These are shown in FIG. 4. Using 1,2-propadiene 8a a mixture of mono- (9a), di- (10a), and triallylamine (11a) was obtained in excellent yield. Allyl amines are among the most versatile intermediates in synthesis and are of industrial importance. For instance, the parent compound 9a, which is produced commercially from ammonia and allyl chloride, is used in antifungal preparations and polymers. As can be seen in FIG. 4, varying the $NH_3$/allene ratio can significantly control the selectivity of this reaction, and of particular interest the parent allyl amine 9a and the triallylamine 11a can be obtained with 86 and 91% selectivity, respectively (not optimized). The addition of $NH_3$ to 1,2-dienes is not restricted to the parent allene 8a. The dialkyl substituted derivative 8b is also converted to the corresponding allyl amines 9b-11b, with exclusive addition of the $NH_2$ group at the less hindered terminus; however the mono/di/tri selectivity of this reaction needs some improvement. Interestingly, even the tetrasubstituted allene 8c undergoes hydroamination with ammonia.

The results outlined above demonstrate that ligated gold(I) and gold(III) complexes readily mediate the addition of $NH_3$ to non activated alkynes and allenes. This reaction gives rise to reactive nitrogen derivatives such as imines, enamines and allyl amines, and is therefore an ideal initial step for the preparation of simple bulk chemicals, as well as rather complex molecules as illustrated by the preparation of heterocycles 5-7. Moreover, since gold complexes, even supported by simple ligands, mediate the addition of $NH_3$ to carbon-carbon multiple bonds, it is obvious to a person skilled in the art that a large portfolio of hydroamination catalysts with different properties can be developed. The disclosed invention also paves way for the use of Werner type complexes for a variety of catalytic processes, which includes the direct catalytic addition of ammonia to even more challenging substrates such as simple alkenes.

V. Hydroamination of Allenes and Alkynes with Amines

In another aspect, the present invention provides a method for catalytic hydroamination, comprising contacting a compound having an alkyne or allene functional group with an amine in the presence of a catalytic amount of a gold complex under conditions sufficient for hydroamination to occur, thereby preparing a hydroamination product.

The amine can be any suitable amine. For example, the amine can be a primary amine. Alternatively, the amine can be a secondary amine. In some aspects, the amine has the following formula:

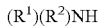

In the formula above, radicals $R^1$ and $R^2$ are each independently selected from the group consisting of hydrogen, $C_{1-6}$ alkyl, cycloalkyl, heterocycloalkyl, aryl and heteroaryl, wherein the cycloalkyl, heterocycloalkyl, aryl and heteroaryl groups are each optionally substituted with 1-4 $R^3$ groups. Alternatively, radicals $R^1$ and $R^2$ are combined with the atom to which they are attached to form a $C_{3-8}$ heterocycloalkyl or a $C_{5-10}$ heteroaryl. Moreover, each radical $R^3$ is independently selected from the group consisting of $C_{1-6}$ alkyl, halogen, $C_{1-6}$ haloalkyl, and $C_{1-6}$ alkoxy. In addition, at least one of radicals $R^1$ and $R^2$ is other than hydrogen Alkynes useful in the method of preparing allenes are described above, along with the catalyst and reaction conditions.

VI. Preparation of Allenes Via Hydroamination

In another aspect, the present invention provides a method of preparing an allene via catalytic hydroamination, comprising contacting a compound having an alkyne functional group with an amine in the presence of a catalytic amount of a gold complex under conditions sufficient for hydroamination to occur, thereby preparing a hydroamination product. The method also comprises the hydroamination product with a second compound having an alkyne functional group, under conditions sufficient to form an allene.

Alkynes useful in the method of preparing allenes are described above, along with the catalyst and reaction conditions.

VII. Preparation of Dihydroisoquinolines via Hydroamination

In another aspect, the present invention provides a method of preparing dihydroisoquinolines via catalytic hydroamination, comprising contacting a compound having an internal alkyne functional group with an aniline functional group in the presence of a catalytic amount of a gold complex under conditions sufficient for hydroamination to occur, thereby preparing a hydroamination product. The method further comprises contacting the hydroamination product with a second compound having an alkyne functional group, under conditions sufficient to form a dihydroisoquinoline.

Alkynes useful in the method of preparing allenes are described above, along with the catalyst and reaction conditions.

VIII. Examples

All experiments were carried out under dry argon using standard Schlenk or dry box techniques. Solvents were dried by standard methods and distilled under argon. $^1H$ (300 MHz, 600 MHz) and $^{13}C$-NMR (75 MHz, 150 MHz) spectra were recorded on a Bruker (Billerica, Mass.) Avance 300 or 600 spectrometer at a temperature of 25° C. and referenced to the residual $^1H$, and $^{13}C$ signals of the solvents. NMR multiplicities are abbreviated as follows: s=singlet, d=doublet, t=triplet, sept.=septet, m=multiplet, br=broad signal. Coupling constants J are given in Hz. Mass spectra were performed at the UC Riverside Mass Spectrometry Laboratory. Melting points were measured with a Bachi melting point apparatus system.

Example 1

Synthesis of Gold Complexes

Synthesis of Complex D

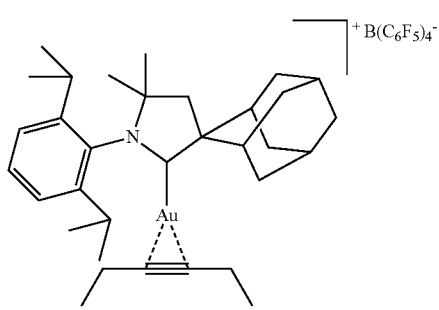

D

One equiv. of 3-hexyne was added to a toluene solution (3 mL) of complex A (1.00 g, 0.743 mmol). The mixture was stirred for 1 min. and hexane (50 mL) was added. The upper portion of the biphasic mixture was removed via canula and the oily residue was dried under high vacuum to afford 0.983 g of complex D as a colorless solid (99% yield). mp: 183-184° C.; $^1$H NMR (300 MHz, $C_6D_6$) δ=0.93 (6H, t, $^3J$=7.5 Hz, $CH_2CH_3$), 1.24 (6H, d, $^3J$=6.7 Hz, $CH(CH_3)_2$), 1.26 (6H, d, $^3J$=6.7 Hz, $CH(CH_3)_2$), 1.37 (6H, s, $C(CH_3)_2$), 1.73-1.98 (12H, m), 2.12 (4H, q, $^3J$=7.5 Hz, $CH_2CH_3$), 2.38 (2H, s, $CH_2$), 2.69 (2H, sept., $^3J$=6.7 Hz, $CH(CH_3)_2$), 3.33 (2H, d, $^2J$=12.7 Hz, $CH_2$), 7.26 (2H, d, J=7.7 Hz), 7.41 (1H, t, J=7.7 Hz); $^{13}$C NMR (75 MHz, $C_6D_6$) δ=13.7 ($CH_2CH_3$), 15.4 ($CH_2CH_3$), 23.2, 26.5, 27.3, 28.4, 28.9, 29.5, 34.2 ($CH_2$), 36.5 ($CH_2$), 37.3, 38.8 ($CH_2$), 48.5 ($CH_2$), 65.2 ($C_q$), 79.9 ($NC_q$), 87.5 (CC), 126.2 ($CH_m$), 131.3 ($CH_p$), 135.9 (m, $B(C_6F_5)_4$), 135.8 ($C_i$), 137.5 (m, $B(C_6F_5)_4$), 139.1 (m, $B(C_6F_5)_4$), 141.0 (m, $B(C_6F_5)_4$), 145.3 ($C_o$), 148.0 (m, $B(C_6F_5)_4$), 151.1 (m, $B(C_6F_5)_4$), 243.9 ($C_{carbene}$); HRMS (ESI) ($CH_3CN$): 615.3011 [(M-$C_6H_{10}$+$CH_3CN$)$^+$, 615.3008 ($C_{29}H_{42}AuN_2$)].

Synthesis of Complex E

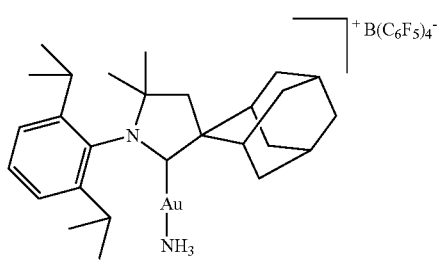

E

To a solution of complex A (1.0 g, 0.743 mmol) in toluene (3 mL) at −50° C., excess $NH_3$ (approximately 1 mL) was condensed. The mixture was stirred for 1 min. and subsequently removed from the cold bath. After elimination of excess $NH_3$, hexane (50 mL) was added. The upper portion of the biphasic mixture removed via canula and the oily residue was dried under high vacuum to afford 0.934 g of complex E as a colorless solid (99% yield). mp: 112-114° C.; $^1$H NMR (300 MHz, $C_6D_6$) δ=1.19 (6H, d, $^3J$=6.7 Hz, $CH(CH_3)_2$), 1.22 (6H, d, $^3J$=6.7 Hz, $CH(CH_3)_2$), 1.30 (6H, s, $C(CH_3)_2$), 1.70-1.97 (12H, m), 2.31 (2H, s, $CH_2$), 2.53 (3H, br s, $NH_3$), 2.60 (2H, sept., $^3J$=6.7 Hz, $CH(CH_3)_2$), 3.50 (2H, d, $^2J$=12.0 Hz, $CH_2$), 7.18 (2H, d, J=7.7 Hz), 7.35 (1H, t, J=7.7 Hz); $^{13}$C NMR (75 MHz, $C_6D_6$) δ=22.8, 26.8, 27.4, 28.5, 28.8, 29.4, 34.4 ($CH_2$), 35.9 ($CH_2$), 37.3, 39.1 ($CH_2$), 48.1 ($CH_2$), 64.2 ($C_q$), 78.7 ($NC_q$), 125.6 (CHO), 131.0 (CHO), 135.5 ($C_i$), 135.6 (m, $B(C_6F_5)_4$), 137.4 (m, $B(C_6F_5)_4$), 138.9 (m, $B(C_6F_5)_4$), 140.8 (m, $B(C_6F_5)_4$), 145.1 ($C_o$), 147.9 (m, $B(C_6F_5)_4$), 151.1 (m, $B(C_6F_5)_4$), 236.7 ($C_{carbene}$); HRMS (ESI) ($CH_3CN$): 615.3010 [(M-$NH_3$+$CH_3CN$)$^+$, 615.3008 ($C_{29}H_{42}AuN_2$)]; 601.2856 [(M-$NH_3$+HCN)$^+$, 601.2856 ($C_{23}H_{40}AuN_2$)].

Synthesis of Complex F

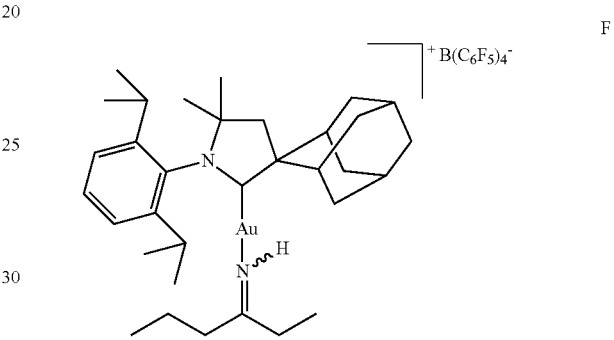

F

To a solution of the Werner complex E (500 mg, 0.394 mmol) in benzene (3 mL) 3-hexyne (6.47 g, 78.7 mmol) was added. The mixture was stirred for 24 h and hexane (100 mL) was added. The upper portion of the biphasic mixture was removed via canula and the oily residue was dried under high vacuum to afford 0.498 g of complex F as a colorless solid (55:45 mixture of cis/trans, 99% yield).

Complex F can also be prepared from A as followed. To a solution of complex A (0.100 g, 0.0743 mmol) in benzene (1 mL), imine 3a (7.4 mg, 0.074 mmol) was added. The mixture was stirred for 1 min. and hexane (20 mL) was added. The upper portion of the biphasic mixture was removed via canula and the oily residue was dried under high vacuum to afford 0.099 g of complex F as a colorless solid (55:45 mixture of cis/trans, 99% yield). $^1$H NMR (300 MHz, $CDCl_3$) δ=0.80 (3H, t, J=7.1 Hz, $CH_3$), 0.88 (3H, t, J=7.8 Hz, $CH_3$), 0.89 (3H, t, J=7.8 Hz, $CH_3$), 1.07 (3H, t, J=7.1 Hz, $CH_3$), 1.29 (6H, d, $^3J$=6.7 Hz, $CH(CH_3)_2$), 1.30 (6H, d, $^3J$=6.7 Hz, $CH(CH_3)_2$), 1.33 (12H, br d, $^3J$=7.1 Hz $C(CH_3)_2$), 1.41 (6H, s, $C(CH_3)_2$), 1.42 (6H, s, $C(CH_3)_2$), 1.45-1.55 (4H, br m, J=7.2 Hz, $CH_2$), 1.75-2.18 (24H, m), 2.29 (4H, tr, J=8.2 Hz, $HNC(CH_2CH_2CH_3)$), 2.40 (4H, q, J=7.1 Hz, $HNC(CH_2CH_3)$), 2.42 (4H, s, $CH_2$), 2.76 (4H, sept., $^3J$=6.7 Hz, $CH(CH_3)_2$), 3.50-3.75 (4H, br m), 7.30 (4H, d, J=7.7 Hz), 7.46 (2H, t, J=7.7 Hz), 8.30-8.40 (2H, br s, NH); $^{13}$C NMR (75 MHz, $CDCl_3$) δ=8.6 ($CH_2CH_3$), 11.1 ($CH_2CH_3$), 13.1 ($CH_2CH_3$), 13.8 ($CH_2CH_3$), 18.5 ($CH_2CH_3$), 20.2 ($CH_2CH_3$), 23.0, 23.1, 26.6, 26.7, 26.9, 27.9, 29.2, 29.4, 32.5 ($CH_2$), 33.8 ($CH_2$), 34.3 ($CH_2$), 35.7 ($CH_2$), 37.2, 38.8 ($CH_2$), 40.7 ($CH_2$), 42.4 ($CH_2$), 48.5 ($CH_2$), 64.3 ($C_q$), 64.4 ($C_q$), 78.6 ($NC_q$), 78.6 ($NC_q$), 125.5 (CHO, 130.5 ($CH_p$), 130.6 ($CH_p$), 134.9 (m, $B(C_6F_5)_4$), 135.8 (br, $C_i$), 136.8 (m, $B(C_6F_5)_4$), 138.0 (m, $B(C_6F_5)_4$), 140.0 (m, $B(C_6F_5)_4$), 145.0 ($C_o$), 145.1 ($C_o$), 146.6 (m, B(C$_6$F$_5$)$_4$), 150.1 (m, B(C$_6$F$_5$)$_4$), 199.6 (C=N), 200.2 (C=N), 238.1 (C$_{carbene}$), 238.6 (C$_{carbene}$).

Example 2

Synthesis of a Silver Complex

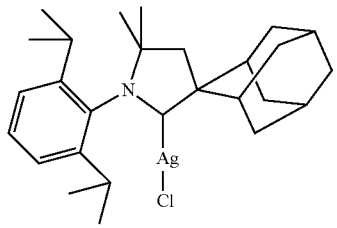

A Schlenk tube was loaded with adamantyl substituted cyclic alkyl amino carbene (500 mg, 1.32 mmol) and AgCl (190 mg, 1.32 mmol). THF (10 mL) was added and the mixture was stirred for 24 h in the absence of light. Subsequent filtration and concentration of the solution under high vacuum afforded 956 mg of the silver carbene complex (95%); mp: 288° C. (dec.); $^1$H NMR (300 MHz, CDCl$_3$) δ=1.30 (6H, d, $^3$J=6.7 Hz, CH(CH$_3$)$_2$), 1.32 (6H, d, $^3$J=6.7 Hz, CH(CH$_3$)$_2$), 1.36 (6H, s, C(CH$_3$)$_2$), 1.74-2.04 (12H, m), 2.19 (1H, s), 2.25 (1H, s), 2.60 (2H, sept., $^3$J=6.7 Hz, CH(CH$_3$)$_2$), 3.44 (2H, d, $^2$J=12.2 Hz, CH$_2$), 7.26 (2H, d, J=7.7 Hz), 7.41 (1H, t, J=7.7 Hz); $^{13}$C NMR (75 MHz, CDCl$_3$) δ=22.9, 27.2, 27.5, 27.7, 29.1, 29.7, 34.6 (CH$_2$), 35.5 (d, J$_{C-Ag}$=2.1 Hz, CH$_2$), 37.3, 38.8 (CH$_2$), 48.0 (d, J$_{C-Ag}$=6.0 Hz, CH$_2$), 64.6 (d, J$_{C-Ag}$=12.8 Hz, C$_q$), 79.5 (d, J$_{C-Ag}$=12.3 Hz, NC$_q$), 125.2 (CH$_m$), 130.0 (CH$_p$), 135.9 (d, J$_{C-Ag}$=2.6 Hz, C$_i$), 145.0 (C$_o$), 262.4 (dd, J$_{C-109Ag}$=246.5 Hz, J$_{C-107Ag}$=214.0 Hz, C$_{carbene}$); HRMS (ESI) (CH$_3$CN): 525.2401 [(M-Cl+CH$_3$CN)$^+$, 525.2399 (C$_{29}$H$_{42}$AgN$_2$)].

Example 3

Hydroamination of Allenes and Alkynes with Ammonia

General Catalytic Procedure: The catalyst (15 mg) and the appropriate amount of alkyne or allene (see main FIG. 2 for mol %) were loaded into a Wilmad QPV thick walled (1.4 mm) NMR tube. C$_6$D$_6$ (0.4 mL) and benzyl methyl ether (5 mg) as an internal standard were added to the mixture. For low catalyst loading (0.1 mol %) experiments, 3 mg of catalyst and 0.1 mL of C$_6$D$_6$ were used. The NMR tube was connected to a high vacuum manifold and excess NH$_3$ (typically 3-6 equivalents) was carefully condensed at −60° C. For experiments with 1,2-propadiene, the allene was first condensed with subsequent addition of NH$_3$. The tube was sealed and placed into an oil bath behind a blast shield, and heated at the specified temperature. ChemDraw® Ultra 10.0 was utilized to name most of the compounds presented in example 3.

Imine 3a

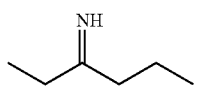

3a

Hexan-3-imine was obtained by reacting 3-hexyne with ammonia in the presence of a catalyst (catalysts A, A/A1, B and C were successfully used in different reactions at temperatures and for times shown in FIG. 2). $^1$H NMR (300 MHz, C$_6$D$_6$) δ=0.76 (3H, t, J=7.4 Hz, CH$_3$), 0.87 (3H, t, J=7.3 Hz, CH$_3$), 1.37 (2H, br qt, J=7.2 Hz, CH$_2$), 1.87 (4H, m, HNC(CH$_2$)$_2$); $^{13}$C NMR (75 MHz, C$_6$D$_6$) δ=9.5 (CH$_3$), 13.5 (CH$_3$), 19.0 (CH$_2$), 31.9 (CH$_2$), 41.2 (CH$_2$), 182.4 (C=NH); HRMS (ESI): 100.1119 [(MH)$^+$, 100.1121 (C$_6$H$_{14}$N)].

Imine 3b

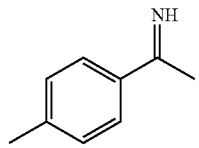

3b 1-p-tolylethanimine was prepared by reacting 1-ethynyl-4-methylbenzene and excess ammonia in the presence of 5 mol % of catalyst E (110° C., 18 h). The yield was 60%. $^1$H NMR (600 MHz, C$_6$D$_6$) δ=2.17 (3H, s, CH$_3$), 2.18 (3H, s, CH$_3$), 7.07 (2H, d, J=7.9 Hz, CH), 7.72 (2H, d, J=7.9 Hz, CH); $^{13}$C NMR (150 MHz, C$_6$D$_6$) δ=21.3 (CH$_3$), 25.7 (NCCH$_3$), 127.3 (CH$_{ortho}$), 129.5 (CH$_{meta}$), 136.9 (C$_{q,ipso}$), 140.8 (C$_{q,para}$CH$_3$), 173.7 (C=NH); HRMS (ESI): 134.0968 [(MH)$^+$, 134.0970 (C$_9$H$_{12}$N)].

Azadiene 4c

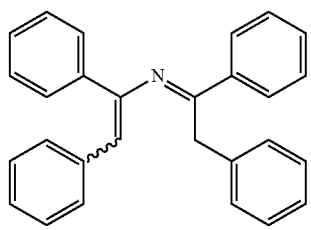

4c

N-(1,2-diphenylethylidene)-1,2-diphenylethanimine was obtained by reacting 1,2-diphenyl acetylene with ammonia in the presence of 1 mol % of catalyst E (165° C., 18 h). The yield was 95%. $^1$H NMR (300 MHz, CDCl$_3$) δ=3.80 (2H, s, CH$_2$), 5.74 (1H, s, CH), 7.02-7.36 (16H, m, CH), 7.53 (2H, d, J=7.5 Hz, CH), 7.63 (2H, dd, J=7.7 Hz, J=1.7 Hz, CH); $^{13}$C NMR (75 MHz, CDCl$_3$) δ=43.9 (CH$_2$), 101.5 (CH), 125.1 (CH), 126.0 (CH), 126.8 (CH), 127.4 (CH), 127.7 (CH), 128.4 (CH), 128.6 (CH), 128.7 (CH), 128.9 (CH), 129.1 (CH), 130.2 (CH), 130.7 (CH), 135.3 (C$_q$), 138.6 (C$_q$), 138.7 (C$_q$), 140.4 (C$_q$), 143.1 (C$_q$), 176.4 (N=C$_q$CH$_2$); HRMS (ESI): 374.1907 [(MH)$^+$, 374.1909 (C$_{28}$H$_{24}$N)], 284.1438 [(M-(CH$_2$Ph)+H)$^+$, 284.1439 (C$_{21}$H$_{18}$N)], 196.1123 [196.1126 (C$_{14}$H$_{14}$N)].

Heterocycle 6f

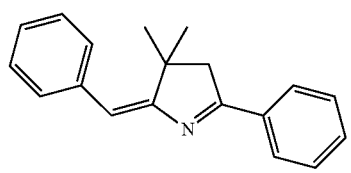

6f 2-benzylidene-3,3-dimethyl-5-phenyl-3,4-dihydro-2H-pyrrole was prepared by reacting (3,3-dimethylpenta-1,4-diyne-1,5-diyl)dibenzene with ammonia in the presence of 10 mol % of catalyst E (165° C., 18 h). Compound 6f was the major product of the reaction (60%) which had a yield of 88%. Single crystals suitable for an X-ray diffraction study were obtained by slow evaporation of a hexane solution. mp: 101-103° C. (n-hexane) an Ortep diagram is shown in FIG. 6; $^1$H NMR (300 MHz, CDCl$_3$) δ=1.37 (6H, s, CH$_3$), 2.99 (2H, s, CH$_2$), 5.98 (1H, s, CH), 7.24 (1H, t, J=7.4 Hz, CH), 7.41 (2H, t, J=7.7 Hz, CH), 7.49 (1H, d, J=1.3 Hz, CH), 7.51 (2H, d, J=2.3 Hz, CH), 8.05-8.10 (4H, m, CH); $^{13}$C NMR (75 MHz, CDCl$_3$) δ=29.6 (CH$_3$), 41.9 (C$_q$), 49.3 (CH$_2$), 115.6 (CH), 126.5 (CH), 128.4 (CH), 128.4 (CH), 129.6 (CH), 131.3 (CH), 134.8 (C$_q$), 137.6 (C$_q$), 165.9 (NC$_q$CH), 174.4 (N=C$_q$CH$_2$); HRMS (ESI): 262.1594 [(M+H)$^+$, 262.1596 (C$_{19}$H$_{20}$N)].

Heterocycle 7f

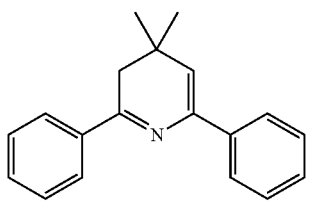

7f 4,4-dimethyl-2,6-diphenyl-3,4-dihydropyridine was obtained by reacting (3,3-dimethylpenta-1,4-diyne-1,5-diyl)dibenzene with ammonia in the presence of 10 mol % of catalyst E (165° C., 18 h). Compound 7f was the minor product of the reaction (40%) which had a yield of 88%. $^1$H NMR (300 MHz, CDCl$_3$) δ=1.15 (6H, s, CH$_3$), 2.64 (2H, s, CH$_2$), 5.88 (1H, s, CH), 7.34 (1H, t, J=7.3 Hz, CH), 7.43 (2H, t, J=7.5 Hz, CH), 7.49 (2H, d, J=2.2 Hz, CH), 7.51 (1H, br, CH), 7.94 (2H, d, J=7.5 Hz, CH), 8.10 (1H, d, J=2.2 Hz, CH), 8.12 (1H, br, CH); $^{13}$C NMR (150 MHz, CDCl$_3$) δ=27.6 (CH$_3$), 30.5 (C$_q$), 38.7 (CH$_2$), 121.3 (CH), 125.7 (CH), 127.3 (CH), 128.5 (CH), 128.6 (CH), 131.5 (CH), 138.9 (C$_q$), 139.6 (C$_q$), 143.2 (NC$_q$CH), 164.8 (N=C$_q$CH$_2$); HRMS (ESI): 262.1593 [(M+H)$^+$, 262.1596 (C$_{19}$H$_{20}$N)].

Diallyl Amine Derivative 10b

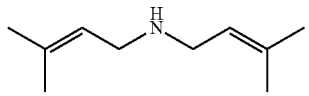

10b

Bis(3-methylbut-2-enyl)amine was prepared by reacting 3-methylbuta-1,2-diene with ammonia in the presence of 1.3 mol % of catalyst E (155° C., 22 h). The reaction produced a mixture of products which are listed in FIG. 4. $^1$H NMR (300 MHz, C$_6$D$_6$) δ=1.53 (3H, s, CH$_3$), 1.63 (3H, s, CH$_3$), 3.19 (2H, d, J=6.7 Hz, NCH$_2$), 5.35 (1H, tsept, J=6.7 Hz, J=1.4 Hz, CH); $^{13}$C NMR (75 MHz, C$_6$D$_6$) δ=18.2 (CH$_3$), 26.1 (CH$_3$), 47.7 (NCH$_2$), 125.2 (CH), 134.1 (C(CH$_3$)$_2$); HRMS (ESI): 154.1594 [(MR)$^+$, 154.1596 (C$_{10}$H$_{20}$N)].

Triallyl Amine Derivative 11b

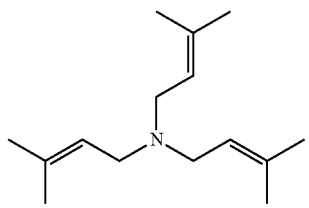

11b

Tris(3-methylbut-2-enyl)amine was prepared by reacting 3-methylbuta-1,2-diene with ammonia in the presence of 1.3 mol % of catalyst E (155° C., 22 h). The reaction produced a mixture of products which are listed in FIG. 4. $^1$H NMR (300 MHz, C$_6$D$_6$) δ=1.65 (3H, s, CH$_3$), 1.78 (3H, s, CH$_3$), 3.55 (2H, d, J=6.7 Hz, NCH$_2$), 5.46 (1H, tsept, J=6.7 Hz, J=1.4 Hz, CH); $^{13}$C NMR (75 MHz, C$_6$D$_6$) δ=18.4 (CH$_3$), 26.3 (CH$_3$), 52.2 (NCH$_2$), 124.1 (CH), 134.1 (C(CH$_3$)$_2$). This compound was isolated as its already known HCl salt. $^1$H NMR (300 MHz, CDCl$_3$) δ=1.65 (3H, s, CH$_3$), 1.79 (3H, s, CH$_3$), 3.55 (2H, m, NCH$_2$), 5.46 (1H, m, CH); $^{13}$C NMR (75 MHz, CDCl$_3$) δ=18.5 (CH$_3$), 26.2 (CH$_3$), 49.3 (NCH$_2$), 113.0 (CH), 143.0 (C(CH$_3$)$_2$); HRMS (EST): 222.2219 [(MH)$^+$, 222.2222 (C$_{15}$H$_{28}$N)].

Vinyl Amine 12c

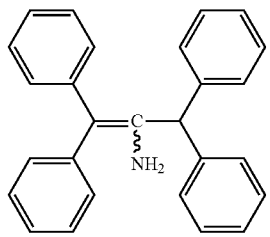

12c 1,1,3,3-tetraphenylprop-1-en-2-amine was obtained when 1,1,3,3-tetraphenylpropa-1,2-diene with ammonia in the presence of 5 mol % of catalyst E (175° C., 44 h). The reaction produced compound 12c in 79% yield. $^1$H NMR (600 MHz, CDCl$_3$) δ=3.43 (2H, s, NH$_2$), 5.30 (1H, s, CH), 7.11 (2H, d, J=6.9 Hz), 7.17 (2H, d, J=7.6 Hz), 7.24 (2H, d, J=7.3 Hz), 7.25-7.35 (12H, m), 7.42 (2H, d, J=7.9 Hz); $^{13}$C NMR (75 MHz, CDCl$_3$) δ=52.5 (CH), 115.2 (C$_q$CNH$_2$), 126.0 (CH), 126.2 (CH), 126.8 (CH), 127.7 (CH), 128.2 (CH), 128.6 (CH), 128.7 (CH), 128.9 (CH), 129.3 (CH), 129.5 (CH), 130.3 (CH), 130.6 (CH), 136.5 (CNH$_2$), 139.9 (C$_q$), 142.0 (C$_q$), 142.5 (C$_q$), 142.7 (C$_q$); HRMS (ESI): 362.1909 [(MH)$^+$, 362.1909 (C$_{27}$H$_{24}$N)].

Example 4

Crystallography

The Bruker X8-APEX X-ray diffraction instrument with Mo-radiation was used for data collection. All data frames were collected at low temperatures (T=100 or 180 K) using an ω, φ-scan mode (0.5o ω-scan width, hemisphere of reflections) and integrated using a Bruker SAINTPLUS software package. The intensity data were corrected for Lorentzian polarization. Absorption corrections were performed using the SADABS program. The SIR97 was used for direct methods of phase determination, and Bruker SHELXTL software package for structure refinement and difference Fourier maps. Atomic coordinates, isotropic and anisotropic displacement parameters of all the non-hydrogen atoms of two compounds were refined by means of a full matrix least-squares procedure on F2. All H-atoms were included in the refinement in calculated positions riding on the C atoms. Drawings of molecules were performed using Ortep 3 (Sxxii). Five member-ring of compound 6f was found to be statistically disordered on two positions and was anisotropically refined with the aid of some restraints applied on angles and interatomics bonds distances in order to get a chemically reasonable model.

Crystal and structure parameters of E (FIG. 5): size 0.32× 0.09×0.07 mm$^3$, orthorhombic, space group P bca, a=20.470 (14) Å, b=18.048(13) Å, c=28.94(2) Å, α=β=γ=90.0°, V=10.692(13) Å$^3$, $\rho_{calcd}$=1.727 g/cm$^3$, Mo-radiation (λ=0.71073 Å), T=180(2) K, reflections collected=44237, independent reflections=6954 ($R_{int}$=0.1383), absorption coefficient μ=3.010 mm$^{-1}$; max/min transmission=0.8169 and 0.4459, 114 parameters were refined and converged at R1=0.0496, wR2=0.1018, with intensity I>2σ(I), the final difference map was 0.832 and −0.692 e·Å$^{-3}$.

Crystal and structure parameters of 6f (FIG. 6): size 0.28× 0.20×0.17 mm$^3$, monoclinic, space group P 2(1)/n, a=5.9369 (19) Å, b=8.234(3) Å, c=29.758(9) Å, α=γ=90.0° β=90.837 (5), V=1454.5(8) Å$^3$, $\rho_{calcd}$=1.193 g/cm3, Mo-radiation (λ=0.71073 Å), T=100(2) K, reflections collected=6240, independent reflections=3182 ($R_{int}$=0.0384), absorption coefficient μ=0.069 mm$^{-1}$; max/min transmission=0.9884 and 0.9810, 260 parameters were refined and converged at R1=0.0554, wR2=0.1185, with intensity I>2σ(I), the final difference map was 0.259 and −0.241 e·Å$^{-3}$.

Example 5

Hydroamination of Alkynes with Amines

General. All reactions were performed under an atmosphere of argon and deuterated benzene was dried over Na/K alloy. Reagents were of analytical grade, obtained from commercial suppliers and used without further purification. Flash chromatography was performed using Merck 60-Å 230-400 mesh silica gel. $^1$H NMR, and $^{13}$C NMR spectra were obtained with a Bruker Advance 300 spectrometer or Bruker 400 spectrometer at 298 K. $^1$H and $^{13}$C chemical shifts (δ) are reported in parts per million (ppm) referenced to TMS, and were measured relative to the residual solvent peak. Electro Spray Ionisation (ESI) or Electronic Impact (EI) mass spectra were obtained at the UC Riverside Mass Spectrometry Laboratory.

Alkynes and amines are commercially available from Sigma-Aldrich and Acros Organics. CAAC(AuCl) complex A1 and complex A (S1) were prepared according to the literature. The spectroscopic data observed for products of Table of FIG. 7, entry 1 (S2), and Table of FIG. 8, entry 3 (S3), Table of FIG. 8, entry 11 (S4) are identical to those reported in the literature.

General procedure for the catalytic hydroamination of amines and alkynes: In a dried J-Young-Tube, CAAC(AuCl) complex A1 (15 mg, 0.025 mmol) and KB($C_6F_5$)$_4$ (16 mg, 0.025 mmol) were loaded under an argon atmosphere. $C_6D_6$ (0.4 mL) and benzyl methyl ether, as an internal standard, were added and after shaking the tube, the alkyne (0.5 mmol) and amine (0.5 mmol) were loaded. The tube was sealed, placed in an oil bath behind a blast shield, and heated at the specified temperature. NMR technique was used to check the reaction products and the conversion. The products were purified by removal of the solvent and extraction with hexane.

General procedure for the catalytic homocoupling of alkynes: In a dried J-Young-Tube, CAAC(AuCl) complex A1 (15 mg, 0.025 mmol) and KB($C_6F_5$)$_4$ (16 mg, 0.025 mmol) were loaded under an argon atmosphere. $C_6D_6$ (0.4 mL) and benzyl methyl ether, as an internal standard, were added and after shaking the tube, terminal alkyne (1.0 mmol) and amine (0.5 mmol) were loaded. The tube was sealed, placed in an oil bath behind a blast shield, and heated at 120° C. for 16 h. NMR technique was used to check the reaction products and the conversion. The products were purified by column chromatography.

General procedure for the catalytic cross-coupling of alkynes: In a dried J-Young-Tube, CAAC(AuCl) complex A1 (15 mg, 0.025 mmol) and KB($C_6F_5$)$_4$ (16 mg, 0.025 mmol) were loaded under an argon atmosphere. $C_6D_6$ (0.4 mL) and benzyl methyl ether, as an internal standard, were added and after shaking the tube, internal alkyne (0.55 mmol) and amine (0.5 mmol) were loaded. The tube was sealed, placed in an oil bath behind a blast shield, and heated at 120° C., and the reaction was monitored by NMR spectroscopy. After complete conversion of the reactants, a terminal alkyne (0.5 mmol) was added, and the reaction mixture heated at 130° C. for 16 h. The products were further purified by column chromatography.

Table of FIG. 7, entry 2

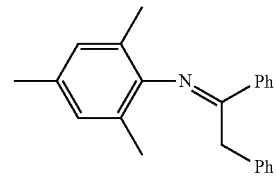 [SMILES: Cc1cc(C)c(/N=C(\Cc2ccccc2)c2ccccc2)c(C)c1]

$^1$H NMR (300 MHz, CDCl$_3$): δ=8.15 (dd, J=4.3 Hz, J=1.9 Hz, 2H, CH), 7.24 (dd, J=1.9 Hz, J=1.8 Hz, 2H, CH), 7.02-6.98 (m, 6H, CH), 6.95 (s, 2H, CH), 3.88 (s, 2H, CH$_2$), 2.33 (s, 3H, CH$_3$), 2.12 (s, 6H, CH$_3$); $^{13}$C NMR (75 MHz, CDCl$_3$): δ=166.7 (CN), 147.1 ($C^{Ar}$N), 139.4 ($C^q$), 137.2 ($C^q$), 132.2 (CH), 130.7 (CH), 129.5 (CH), 129.0 (CH), 128.9 (CH), 128.7 (CH), 128.0 (CCH$_3$), 126.8 (CCH$_3$), 126.1 (CH), 36.9 (CH$_2$), 21.2 (CH$_3$), 18.7 (CH$_3$); HRMS (ESI): m/z calcd for C$_{23}$H$_{24}$N, 314.1909 [(M+H)]$^+$; found: 314.1910.

Table of FIG. 7, entry 3

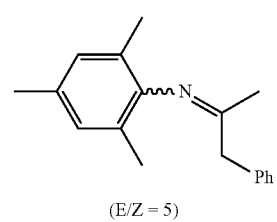 [SMILES: CC(Cc1ccccc1)=Nc1c(C)cc(C)cc1C]

(E/Z = 5)

$^1$H NMR (300 MHz, CDCl$_3$): δ=7.43-7.37 (m, 3H, CH), 7.34-7.32 (m, 2H, CH), 6.87 (s, 2H, CH), 3.84 (s, 2H, CH$_2$ (E)), 3.34 (s, 2H, CH$_2$(Z)), 2.30 (s, 3H, CH$_3$), 2.27 (s, 3H, CH$_3$), 2.02 (s, 6H, CH$_3$), 1.60 (s, 3H, CH$_3$); $^{13}$C NMR (75 MHz, CDCl$_3$): δ=170.6 (CN), 146.0 ($C^{Ar}$N), 131.9 ($C^q$), 129.4 (CH), 128.9 ($C^q$), 128.7 (CH), 128.6 (CH), 126.9 (CH), 125.8 (C$^q$), 48.6 (CH$_2$), 41.1 (CH$_2$), 20.8 (CH$_3$), 18.8 (CH$_3$), 18.0 (CH$_3$), 17.6 (CH$_3$); HRMS (ESI): m/z calcd for C$_{18}$H$_{22}$N, 252.1747 [(M+H)]$^+$; found: 252.1747.

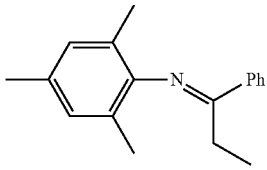 [SMILES: CC/C(=N\c1c(C)cc(C)cc1C)c1ccccc1]

$^1$H NMR (300 MHz, CDCl$_3$): δ=8.03-8.00 (m, 2H, CH), 7.51 (t, $^3$J=3.2 Hz, 3H, CH), 6.93 (s, 2H, CH), 2.54 (q, $^3$J=7.7 Hz, 2H, CH$_2$), 2.34 (s, 3H, CH$_3$), 2.09 (s, 6H, CH$_3$), 1.01 (t, $^3$J=7.7 Hz, 3H, CH$_3$); $^{13}$C NMR (75 MHz, CDCl$_3$): δ=170.6 (CN), 151.3 (C$^{Ar}$N), 137.4 (C$^q$), 130.2 (CH), 129.5 (CH), 128.5 (CH), 127.6 (CH), 126.6 (C$^q$), 125.5 (C$^q$), 23.8 (CH$_2$), 20.9 (CH$_3$), 18.2 (CH$_3$), 11.5 (CH$_3$); HRMS (ESI): m/z calcd for C$_{18}$H$_{22}$N, 252.1747 [(M+H)]$^+$; found: 252.1747.

Table of FIG. 7, entry 4

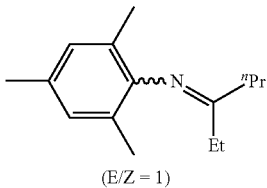

(E/Z = 1)

$^1$H NMR (300 MHz, C$_6$D$_6$): δ=6.93 (s, 2H, CH), 2.31 (m, 3H, CH$_3$), 2.11 (s, 6H, CH$_3$), 1.91-1.80 (m, 4H, CH$_2$), 1.34 (t, $^3$J=7.4 Hz, 2H, CH$_2$), 1.33 (t, $^3$J=7.5 Hz, 2H, CH$_2$), 1.11 (t, $^3$J=7.4 Hz, 3H, CH$_3$), 1.09 (t, $^3$J=7.3 Hz, 3H, CH$_3$), 0.78 (t, $^3$J=7.7 Hz, 3H, CH$_3$(E)), 0.67 (t, $^3$J=7.3 Hz, 3H, CH$_3$(Z)); $^{13}$C NMR (75 MHz, C$_6$D$_6$): δ=174.4 (CN), 147.5 (C$^a$), 147.4 (C$^q$), 131.5 (C$^q$), 129.6 (CH), 129.3 (CH), 125.8 (C$^q$), 125.7 (C$^q$), 39.6 (CH$_2$), 36.2 (CH$_2$), 31.3 (CH$_2$), 27.3 (CH$_2$), 21.2 (CH$_3$), 20.2 (CH$_2$), 20.1 (CH$_2$), 18.7 (CH$_3$), 18.6 (CH$_3$), 17.9 (CH$_3$), 15.0 (CH$_3$), 11.3 (CH$_3$), 10.9 (CH$_3$); HRMS (ESI): m/z calcd for C$_{15}$H$_{24}$N: 218.1909 [(M+H)]$^+$; found: 218.1908.

Table of FIG. 7, entry 5

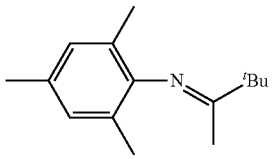 [SMILES: C/C(=N\c1c(C)cc(C)cc1C)C(C)(C)C]

$^1$H NMR (300 MHz, C$_6$D$_6$): δ=6.92 (s, 2H, CH), 2.32 (s, 3H, CH$_3$), 2.05 (s, 6H, CH$_3$), 1.48 (s, 3H, CH$_3$), 1.28 (s, 9H, CH$_3$); $^{13}$C NMR (75 MHz, C$_6$D$_6$): δ=176.3 (CN), 147.5 (C$^{Ar}$N), 131.4 (C$^q$), 129.3 (CH), 125.3 (C$^q$), 40.8 (C$^q$), 28.4 (C$^q$CH$_3$), 21.2 (CH$_3$), 18.1 (CH$_3$), 15.2 (CNCH$_3$); HRMS (ESI): m/z calcd for C$_{15}$H$_{24}$N, 218.1903 [(M+H)]$^+$; found 218.1906.

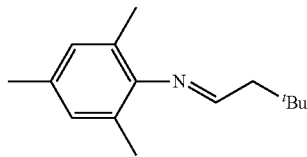 [SMILES: Cc1cc(C)c(/N=C/CC(C)(C)C)c(C)c1]

$^1$H NMR (300 MHz, C$_6$D$_6$): δ=7.55 (t, $^3$J=5.5 Hz, 1H, NCH), 6.92 (s, 2H, CH), 2.31 (s, 3H, CH$_3$), 2.02 (s, 6H, CH$_3$), 1.16 (s, 2H, CH$_2$), 1.01 (s, 9H, CH$_3$); $^{13}$C NMR (75 MHz, C$_6$D$_6$): δ=166.4 (HCN), 147.5 (C$^{Ar}$N), 129.6 (C$^q$), 129.4 (CH), 127.0 (C$^q$), 50.8 (CH$_2$), 31.2 (C$^q$), 30.1 (CH$_3$), 19.0 (CH$_3$), 17.9 (CH$_3$); HRMS (ESI): m/z calcd for C$_{15}$H$_{24}$N, 218.1903 [(M+H)]$^+$; found 218.1906.

Table of FIG. 7, entry 6

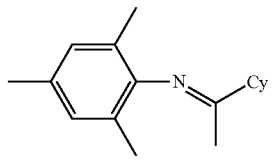

$^1$H NMR (300 MHz, C$_6$D$_6$): δ=6.93 (s, 2H, CH), 2.33 (s, 3H, CH$_3$), 2.08 (s, 6H, CH$_3$), 1.96-1.93 (m, 2H, CH$_2$), 1.85-1.83 (m, 2H, CH$_2$), 1.74 (br, 2H, CH$_2$), 1.65-1.54 (m, 2H, CH$_2$), 1.44 (s, 3H, CH$_3$), 1.34-1.28 (m, 2H, CH$_2$), 1.23-1.21 (m, 1H, CH); $^{13}$C NMR (75 MHz, C$_6$D$_6$): δ=174.1 (CN), 147.6 (C$^{Ar}$N), 131.4 (C$^q$), 129.3 (CH), 125.6 (C$^q$), 49.2 (CH), 31.1 (CH$_2$), 26.9 (CH$_2$), 26.4 (CH$_2$), 21.2 (CH$_3$), 18.3 (CH$_3$), 17.9 (CH$_3$); HRMS (ESI): m/z calcd for C$_{17}$H$_{26}$N, 244.2060 [(M+H)]$^+$; found 244.2060.

Table of FIG. 7, entry 7

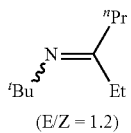

(E/Z = 1.2)

$^1$H NMR (300 MHz, C$_6$D$_6$): δ=2.24-2.08 (m, 8H, CH$_2$), 1.72 (q, $^3$J=7.3 Hz, 4H, CH$_2$), 1.41 (s, 9H, CH$_3$(Z)), 1.39 (s, 9H, CH$_3$(E)), 1.21 (t, $^3$J=7.4 Hz, 3H, CH$_3$), 1.02 (t, $^3$J=7.4 Hz, 3H, CH$_3$), 0.97 (t, $^3$J=7.4 Hz, 3H, CH$_3$), 0.88 (t, $^3$J=7.4 Hz, 3H, CH$_3$); $^{13}$C NMR (75 MHz, C$_6$D$_6$): δ=169.8 (CN), 169.7 (CN), 54.7 (C(CH$_3$)$_3$), 41.8 (CH$_2$), 37.2 (CH$_2$), 33.3 (CH$_2$), 31.8 (C(CH$_3$)$_3$), 31.7 (C(CH$_3$)$_3$), 28.0 (CH$_2$), 21.2 (CH$_2$), 20.8 (CH$_2$), 15.1 (CH$_3$), 14.5 (CH$_3$), 12.0 (CH$_3$), 11.8 (CH$_3$); HRMS (ESI): m/z calcd for C$_{10}$H$_{22}$N, 156.1752 [(M+H)]$^+$; found: 156.1746.

Table of FIG. 8, entry 1

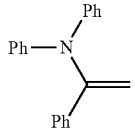

$^1$H NMR (300 MHz, C$_6$D$_6$): δ=7.64 (dd, J=1.6 Hz, J=1.0 Hz, 2H, CH), 7.20 (t, $^3$J=5.7 Hz, 3H, CH), 7.10 (t, $^3$J=7.7 Hz, 4H, CH), 6.95 (t, $^3$J=7.9 Hz, 2H, CH), 6.87 (t, $^3$J=7.3 Hz, 4H,

CH), 5.25 (s, 1H, CH$_2$), 5.01 (s, 1H, CH$_2$); $^{13}$C NMR (75 MHz, CDCl$_3$): δ=153.2 (CN), 148.2 (C$^q$N), 139.2 (C$^q$), 129.5 (CH), 129.3 (CH), 127.4 (CH), 124.3 (GE), 122.8 (CH), 118.1 (CH), 108.1 (CH$_2$); HRMS (ESI): m/z calcd for C$_{20}$H$_{18}$N, 272.1439 [(M+H)]$^+$; found: 272.1439.

Table of FIG. 8, entry 2

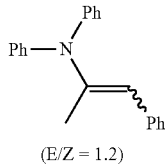

(E/Z = 1.2)

$^1$H NMR (300 MHz, C$_6$D$_6$): δ=7.46 (d, $^3$J=7.7 Hz, 2H), 7.27-7.16 (m, 11H), 7.14-7.04 (m, 9H), 7.00-6.95 (m, 4H), 6.93 (tt, $^3$J=7.2 Hz, $^4$J=1.0 Hz, 2H), 6.85 (tt, $^3$J=7.2 Hz, $^4$J=1.1 Hz, 2H), 6.47 (s, 1H, CCH), 6.19 (s, 1H, CCH), 2.10 (s, 3H, CH$_3$(Z)), 1.98 (s, 3H, CH$_3$(E)); $^{13}$C NMR (75 MHz, C$_6$D$_6$): δ=148.1 (C$^q$), 146.0 (C$^q$), 143.9 (C$^q$), 139.8 (C$^q$), 138.4 (C$^q$), 136.4 (C$^q$), 129.9 (CH), 129.8 (CH), 129.7 (CH), 128.8 (CH), 128.5 (CH), 128.4 (CH), 126.4 (CH), 125.0 (CH), 124.9 (2 CH), 123.2 (CH), 122.5 (CH), 122.1 (CH), 118.5 (CH), 22.6 (CH$_3$), 18.8 (CH$_3$); HRMS (ESI; THF): m/z calcd for C$_{21}$H$_{20}$N, 286.1590 [M+H]$^+$; found: 286.1588.

Table of FIG. 8, entry 4 (S5)

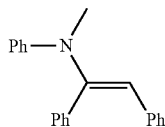

$^1$H NMR (300 MHz, CDCl$_3$): δ=7.61 (dd, J=1.7 Hz, J=1.4 Hz, 2H, CH), 7.54 (d, J=4.2 Hz, 2H, CH), 7.50-7.38 (m, 6H, CH), 7.34-7.30 (m, 3H, CH), 6.90 (t, $^3$J=5.7 Hz, 2H, CH), 6.84 (s, 1H, CH); 3.33 (s, 3H, CH$_3$); $^{13}$C NMR (75 MHz, CDCl$_3$): δ=147.2 (C$^{Ar}$N), 144.2 (CN), 139.5 (C$^q$), 136.4 (C$^q$), 129.1 (CH), 128.7 (CH), 128.6 (CH), 128.5 (CH), 128.2 (CH), 127.4 (CH), 126.9 (CH), 124.0 (CH), 117.7 (CH), 114.1 (CH), 39.1 (CH$_3$); HRMS (ESI): m/z calcd for C$_{21}$H$_{20}$N, 286.1590 [(M+H)]$^+$; found: 286.1590.

Table of FIG. 8, entry 5

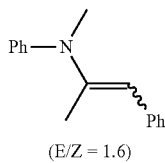

(E/Z = 1.6)

$^1$H NMR (300 MHz, C$_6$D$_6$): δ=7.36-7.26 (m, 5H, CH), 7.23-7.14 (m, 3H, CH), 6.86-6.81 (m, 2H, CH), 6.11 (s, 1H, CH(E)), 6.08 (s, 1H, CH(Z)), 2.99 (s, 3H, CH$_3$(Z)), 2.77 (s, 3H, CH$_3$(E)), 1.96 (s, 3H, CH$_3$(Z)), 1.81 (s, 3H, CH$_3$(E)); $^{13}$C NMR (75 MHz, C$_6$D$_6$): δ=147.5 (C$^{Ar}$N), 142.4 (CN), 136.9 (C$^q$), 129.9 (CH), 129.4 (CH), 129.0 (CH), 128.7 (CH), 128.5 (CH), 127.5 (CH), 125.2 (CH), 123.4 (CH), 123.0 (CH), 114.8 (CH), 112.9 (CH), 112.7 (CH), 41.2 (CH$_3$), 37.0 (CH$_3$), 19.8 (CH$_3$), 18.1 (CH$_3$); HRMS (ESI): m/z calcd for C$_{16}$H$_{18}$N, 224.1434 [(M+H)]$^+$; found: 224.1435.

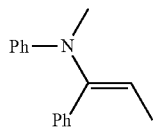

(S6)

$^1$H NMR (300 MHz, C$_6$D$_6$): δ=7.52 (d, $^3$J=7.3 Hz, 2H, CH), 7.09 (m, 3H, CH), 7.00 (d, J=7.7 Hz, 2H, CH), 6.91-6.89 (m, 3H, CH), 5.86 (q, $^3$J=6.8 Hz, 1H, CH), 2.89 (s, 3H, CH$_3$), 1.57 (d, $^3$J=6.9 Hz, 3H, CH$_3$); $^{13}$C NMR (75 MHz, C$_6$D$_6$): δ=149.4 (C$^{Ar}$N), 144.6 (CN), 139.6 (C$^q$), 129.6 (CH), 129.1 (CH), 126.7 (CH), 125.6 (CH), 121.8 (CH), 118.6 (CH), 117.5 (CH), 37.6 (CH$_3$), 14.2 (CH$_3$); HRMS (ESI): m/z calcd for C$_{16}$H$_{18}$N, 224.1434 [(M+H)]$^+$; found: 224.1435.

Table of FIG. 8, entry 6

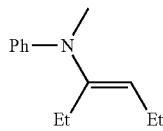

$^1$H NMR (300 MHz, CDCl$_3$): δ=7.21 (t, $^3$J=1.4 Hz, 1H, CH), 6.84-6.74 (m, 4H, CH), 5.32 (t, $^3$J=7.2 Hz, 1H, CH), 2.87 (s, 3H, CH$_3$), 2.45 (q, $^3$J=7.0 Hz, 1H, CH$_2$), 2.43 (q, $^3$J=7.0 Hz, 1H, CH$_2$), 1.98 (q, $^3$J=7.4 Hz, 2H, CH$_2$), 1.10 (t, $^3$J=7.6 Hz, 3H, CH$_2$), 1.04 (t, $^3$J=7.5 Hz, 3H, CH$_3$); $^{13}$C NMR (75 MHz, CDCl$_3$): δ=147.8 (C$^{Ar}$N), 145.3 (CN), 127.0 (CH), 117.4 (CH), 115.8 (CH), 112.5 (CCH$_2$), 37.8 (NCH$_3$), 26.1 (CH$_2$), 20.7 (CH$_2$), 12.9 (CH$_3$), 12.3 (CH$_3$); HRMS (ESI): m/z calcd for C$_{13}$H$_{20}$N, 190.1590 [(M+H)]$^+$; found: 190.1593.

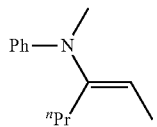

$^1$H NMR (300 MHz, CDCl$_3$): δ=7.26 (t, $^3$J=2.1 Hz, 1H, CH), 7.24 (t, $^3$J=1.4 Hz, 1H, CH), 6.73-6.64 (m, 3H, CH), 5.40 (qt, $^3$J=6.7 Hz, $^4$J=1.0 Hz, 1H, CH), 3.06 (s, 3H, CH$_3$), 2.20 (br qt, $^3$J=7.6 Hz, $^4$J=1.1 Hz, 2H, CH$_2$), 1.53 (d, $^3$J=6.7 Hz, 3H, CH$_3$), 1.48-1.38 (m, 2H, CH$_2$), 0.96-0.89 (m, 3H, CH$_3$); $^{13}$C NMR (75 MHz, CDCl$_3$): δ=147.7 (C$^{Ar}$N), 144.9 (CN), 129.1 (CH), 120.0 (CH), 116.1 (CH), 112.4 (CCH$_3$), 37.4 (NCH$_3$), 35.8 (CH$_2$), 20.9 (CH$_2$), 14.1 (CH$_3$), 8.0 (CH$_3$); HRMS (ESI): m/z calcd for C$_{13}$H$_{20}$N, 190.1590 [(M+H)]$^+$; found: 190.1593.

Table of FIG. 8, entry 7

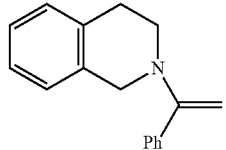 [SMILES: C=C(c1ccccc1)N1CCc2ccccc2C1]

$^1$H NMR (300 MHz, C$_6$D$_6$): δ=7.66 (m, 2H, CH), 7.27-6.86 (m, 7H, CH), 4.60 (s, 1H, CH$_2$), 4.41 (s, 1H, CH$_2$), 4.15 (s, 2H, CH$_2$), 3.02 (t, $^3$J=5.9 Hz, 2H, CH$_2$), 2.85 (t, $^3$J=5.9 Hz,

2H, CH$_2$); $^{13}$C NMR (75 MHz, C$_6$D$_6$): δ=157.1 (CN), 135.2 (C$^q$), 135.0 (C$^q$), 130.3 (CH), 128.9 (CH), 128.7 (CH), 128.4 (CH), 127.6 (C$^q$), 127.1 (CH), 126.8 (CH), 126.7 (CH), 91.7 (CH$_2$), 52.3 (CH$_2$), 47.8 (CH$_2$), 29.9 (CH$_2$); HRMS (BSI): m/z calcd for C$_{17}$H$_{18}$N, 236.1434 [(M+H)]$^+$; found: 236.1439.

Table of FIG. 8, entry 8

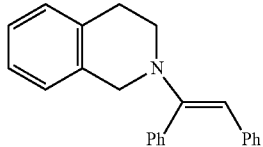 [SMILES: C(=C(/c1ccccc1)N1CCc2ccccc2C1)/c1ccccc1]

M.p.: 115-116° C.; $^1$H NMR (300 MHz, C$_6$D$_6$): δ=7.53-7.50 (m, 2H, CH), 7.18 (t, $^3$J=2.8 Hz, 3H, CH), 7.15-7.09 (m, 5H, CH), 7.03 (t, $^3$J=4.2 Hz, 2H, CH), 6.98 (t, $^3$J=4.2 Hz, 1H, CH), 6.90 (t, $^3$J=4.9 Hz, 1H, CH), 5.87 (s, 1H, CH), 4.23 (s, 2H, CH$_2$), 3.02 (t, $^3$J=5.7 Hz, 2H, CH$_2$), 2.65 (t, $^3$J=5.4 Hz, 2H, CH$_2$); $^{13}$C NMR (75 MHz, C$_6$D$_6$): δ=150.4 (CN), 139.3 (C$^q$), 137.7 (C$^q$), 134.5 (2C$^q$), 130.5 (CH), 128.9 (CH), 128.8 (CH), 128.3 (CH), 127.9 (CH), 126.6 (CH), 126.2 (CH), 126.0 (CH), 124.3 (CH), 106.1 (CH), 51.5 (CH$_2$), 46.4 (CH$_2$), 29.5 (CH$_2$); HRMS (ESI): m/z calcd for C$_{23}$H$_{22}$N, 312.1747 [(M+H)]$^+$; found: 312.1750.

Table of FIG. 8, entry 9

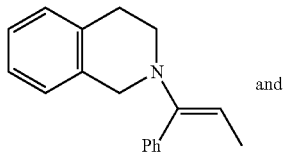

(A)

and

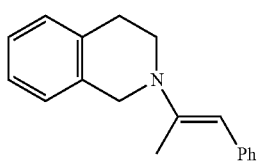

(B)

$^1$H NMR (300 MHz, CDCl$_3$): δ=7.50-7.10 (m, 18H), 5.77 (s, 1H, CH(B)), 4.93 (q, $^3$J=6.9 Hz, 1H, CH(A)), 4.41 (s, 2H, NCH$_2$(B)), 4.17 (s, 2H, NCH$_2$(A)), 3.50 (t, $^3$J=5.8 Hz, 2H, CH$_2$), 3.24 (t, $^3$J=5.8 Hz, 2H, CH$_2$), 3.09 (t, $^3$J=5.8 Hz, 2H, CH$_2$), 2.90 (t, $^3$J=5.8 Hz, 2H, CH$_2$), 2.24 (s, 3H, CCH$_3$(B)), 1.76 (d, $^3$J=6.9 Hz, 3H, CHCH$_3$(A)); $^{13}$C NMR (75 MHz, CDCl$_3$): δ=149.7 (NC), 145.6 (NC), 139.9 (C$^q$), 138.2 (C$^q$), 135.2 (C$^q$), 134.9 (C$^q$), 134.7 (C$^q$), 134.6 (C$^q$), 129.9 (CH), 129.5 (CH), 129.2 (CH), 128.9 (CH), 128.8 (CH), 128.2 (CH), 128.1 (CH), 127.6 (CH), 126.6 (CH), 126.3 (CH), 126.1 (2CH), 125.8 (CH), 124.6 (CH), 104.0 (CH), 100.0 (CH), 52.0 (CH$_2$), 50.8 (CH$_2$), 47.3 (CH$_2$), 45.5 (CH$_2$), 29.6 (CH$_2$), 29.3 (CH$_2$), 17.1 (CH$_3$), 14.2 (CH$_3$); HRMS (ESI): m/z calcd for C$_{18}$H$_{20}$N, 250.1590 [(M+$^{11}$)]$^+$; found: 250.1590.

Table of FIG. 8, entry 10

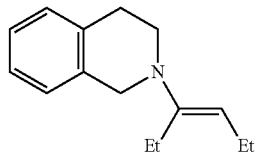 [SMILES: CC/C=C(\CC)N1CCc2ccccc2C1]

$^1$H NMR (300 MHz, C$_6$D$_6$): δ=7.15-7.11 (m, 2H, CH), 7.05 (t, $^3$J=3.2 Hz, 1H, CH), 6.98 (t, $^3$J=4.3 Hz, 1H, CH), 4.59 (t, $^3$J=7.1 Hz, 1H, CH), 4.05 (s, 2H, CH$_2$), 3.01 (t, $^3$J=5.8 Hz, 2H, CH$_2$), 2.75 (t, $^3$J=4.5 Hz, 2H, CH$_2$), 2.29 (q, J=6.8 Hz, 2H, CH$_2$), 1.66-1.56 (m, 2H, CH$_2$), 1.18-1.11 (m, 6H, CH$_3$); $^{13}$C NMR (75 MHz, C$_6$D$_6$): δ=149.6 (CN), 135.9 (C$^q$), 129.3 (C$^q$), 127.1 (CH), 126.5 (CH), 126.3 (CH), 106.9 (CH), 52.4 (CH$_2$), 46.8 (CH$_2$), 30.3 (CH$_2$), 21.6 (CH$_2$), 14.9 (CH$_2$), 14.4 (CH$_3$), 14.2 (CH$_3$).

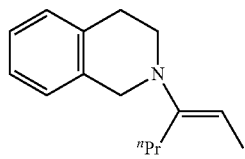

$^1$H NMR (300 MHz, C$_6$D$_6$): δ=7.15-7.11 (m, 2H, CH), 7.05 (m, 1H, CH), 6.98 (t, $^3$J=4.3 Hz, 1H, CH), 4.68 (q, $^3$J=6.7 Hz, 1H, CH), 4.04 (s, 2H, CH$_2$), 3.01 (t, $^3$J=5.8 Hz, 2H, CH$_2$), 2.75 (m, 2H, CH$_2$), 2.18 (t, $^3$J=7.4 Hz, 2H, CH$_2$), 1.79 (d, J=6.7 Hz, 3H, CH$_3$), 1.66-1.56 (m, 2H, CH$_2$), 1.01 (t, $^3$J=7.4 Hz, 3H, CH$_3$); $^{13}$C NMR (75 MHz, C$_6$D$_6$): δ=148.9 (CN), 135.2 (C$^q$), 129.3 (C$^q$), 127.1 (CH), 126.5 (CH), 126.3 (CH), 99.6 (CH), 52.5 (CH$_2$), 46.9 (CH$_2$), 30.6 (CH$_2$), 30.2 (CH$_2$), 22.2 (CH$_2$), 16.4 (CH$_3$), 13.5 (CH$_3$).

Table of FIG. 8, entry 12 (S7)

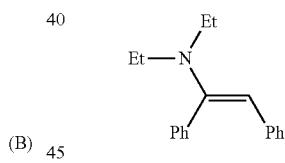

$^1$H NMR (300 MHz, CDCl$_3$): δ=7.62 (m, 1H, CH), 7.42-7.38 (m, 4H, CH), 7.05 (t, $^3$J=7.6 Hz, 2H, CH), 6.93 (t, $^3$J=7.3 Hz, 1H, CH), 6.76 (d, J=7.5 Hz, 2H, CH), 5.59 (s, 1H, CH), 3.14 (q, $^3$J=7.0 Hz, 4H, CH), 1.16 (t, $^3$J=7.0 Hz, 6H, CH); $^{13}$C NMR (75 MHz, CDCl$_3$): δ=149.2 (CN), 139.7 (C$^q$), 138.2 (C$^q$), 131.7 (CH), 130.4 (CH), 128.8 (CH), 127.9 (CH), 127.7 (CH), 123.3 (CH), 104.6 (CH), 43.1 (CH$_2$), 12.3 (CH$_3$); HRMS (ESI): m/z calcd for C$_{18}$H$_{22}$N, 252.1752 [(M+H)]$^+$; found: 252.1750.

Table of FIG. 8, entry 13

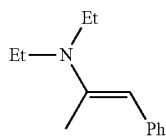

$^1$H NMR (300 MHz, C$_6$D$_6$): δ=7.36-7.34 (m, 2H, CH), 7.30-7.11 (m, 3H, CH), 5.57 (s, 1H, CH), 3.01 (q, $^3$J=7.0 Hz, 4H, CH$_2$), 1.99 (s, 3H, CH$_3$), 1.04-0.98 (m, 6H, CH$_3$); $^{13}$C NMR (75 MHz, C$_6$D$_6$): δ=143.7 (CN), 139.8 (C$^{Ar}$N), 129.7

(CH), 128.6 (CH), 124.3 (CH), 100.9 (CH), 43.6 (CH$_2$), 16.7 (CH$_3$), 13.2 (CH$_3$); HRMS (ESI): m/z calcd for C$_{13}$H$_{20}$N, 190.1590 [(M+H)]$^+$; found: 190.1591.

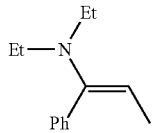

(S8)

$^1$H NMR (300 MHz, C$_6$D$_6$): δ=7.50 (dd, $^3J$=8.4 Hz, $^4J$=1.0 Hz, 2H, CH), 7.30-7.11 (m, 3H, CH), 4.72 (q, $^3J$=7.0 Hz, 1H, CH), 2.91 (q, $^3J$=7.0 Hz, 4H, CH$_2$), 1.78 (d, $^3J$=6.9 Hz, 3H, CH$_3$), 1.04-0.98 (m, 6H, CH$_3$); $^{13}$C NMR (75 MHz, C$_6$D$_6$): δ=148.1 (CN), 141.7 (C$^{Ar}$N), 130.5 (CH), 128.5 (CH), 127.7 (CH), 100.5 (CH), 43.6 (CH$_2$), 14.6 (CH$_3$), 12.0 (CH$_3$); HRMS (ESI): m/z calcd for C$_{13}$H$_{20}$N, 190.1590 [(M+H)]$^+$; found: 190.1591.

Table of FIG. 8, entry 14

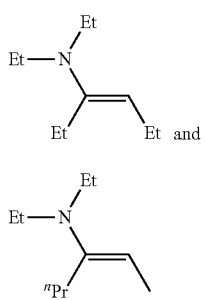

(A)

(B)

A: $^1$H NMR (300 MHz, C$_6$D$_6$): δ=4.44 (t, $^3J$=7.1 Hz, 1H, CH), 2.94 (q, $^3J$=7.0 Hz, 4H, NCH$_2$), 2.20 (m, 4H, CH$_2$), 1.15 (t, $^3J$=7.5 Hz, 3H, CH$_3$), 1.14 (t, $^3J$=7.5 Hz, 3H, CH$_3$), 1.02 (t, $^3J$=7.0 Hz, 6H, CH$_3$);

B: $^1$H NMR (300 MHz, C$_6$D$_6$): δ=4.54 (q, $^3J$=6.7 Hz, 1H, CH), 2.94 (q, $^3J$=7.0 Hz, 4H, NCH$_2$), 2.20 (m, 2H, CH$_2$), 1.80 (d, $^3J$=6.7 Hz, 1H, CH$_3$), 1.61 (qt, $^3J$=7.5 Hz, $^3J$=7.5 Hz, 2H, CH$_2$CH$_2$), 1.10 (m, 3H, CH$_3$), 1.03 (t, $^3J$=7.0 Hz, 6H, CH$_3$); $^{13}$C NMR (75 MHz, C$_6$D$_6$): δ=146.8 (C$^q$(A)), 146.2 (CH(B)), 107.1 (CH(A)), 99.5 (CH(B)), 43.6 (NCH$_2$(B)), 43.5 (NCH$_2$(A)), 30.6 (CH$_2$(B)), 22.3 (CH$_2$(B)), 22.1 (CH$_2$(A)), 21.8 (CH$_2$(A)), 16.6 (CH$_3$), 14.4 (CH$_3$), 14.3 (CH$_3$), 13.6 (CH$_3$), 12.5 (NCH$_2$CH$_3$(B)), 12.4 (NCH$_2$CH$_3$(A)); HRMS (ESI; THF): m/z calcd for C$_{10}$H$_{22}$N, 156.1752 [M+H]$^+$; found: 156.1746.

Example 6

Preparation of Allenes from Alkenes Via Hydroamination

General procedures followed those described above for Example 5. Alkynes and amines are commercially available from Sigma-Aldrich and Acros Organics. CAAC(AuCl) complex A1 and complex A (S1) were prepared according to the literature.

General procedure for the catalytic homocoupling of alkynes: In a dried J-Young-Tube, CAAC(AuCl) complex A1 (15 mg, 0.025 mmol) and KB(C$_6$F$_5$)$_4$ (16 mg, 0.025 mmol) were loaded under an argon atmosphere. C$_6$D$_6$ (0.4 mL) and benzyl methyl ether, as an internal standard, were added and after shaking the tube, terminal alkyne (1.0 mmol) and amine (0.5 mmol) were loaded. The tube was sealed, placed in an oil bath behind a blast shield, and heated at 120° C. for 16 h. NMR technique was used to check the reaction products and the conversion. The products were purified by column chromatography.

General procedure for the catalytic cross-coupling of alkynes: In a dried J-Young-Tube, CAAC(AuCl) complex A1 (15 mg, 0.025 mmol) and KB(C$_6$F$_5$)$_4$ (16 mg, 0.025 mmol) were loaded under an argon atmosphere. C$_6$D$_6$ (0.4 mL) and benzyl methyl ether, as an internal standard, were added and after shaking the tube, internal alkyne (0.55 mmol) and amine (0.5 mmol) were loaded. The tube was sealed, placed in an oil bath behind a blast shield, and heated at 120° C., and the reaction was monitored by NMR spectroscopy. After complete conversion of the reactants, a terminal alkyne (0.5 mmol) was added, and the reaction mixture heated at 130° C. for 16 h. The products were further purified by column chromatography.

Figure 9:
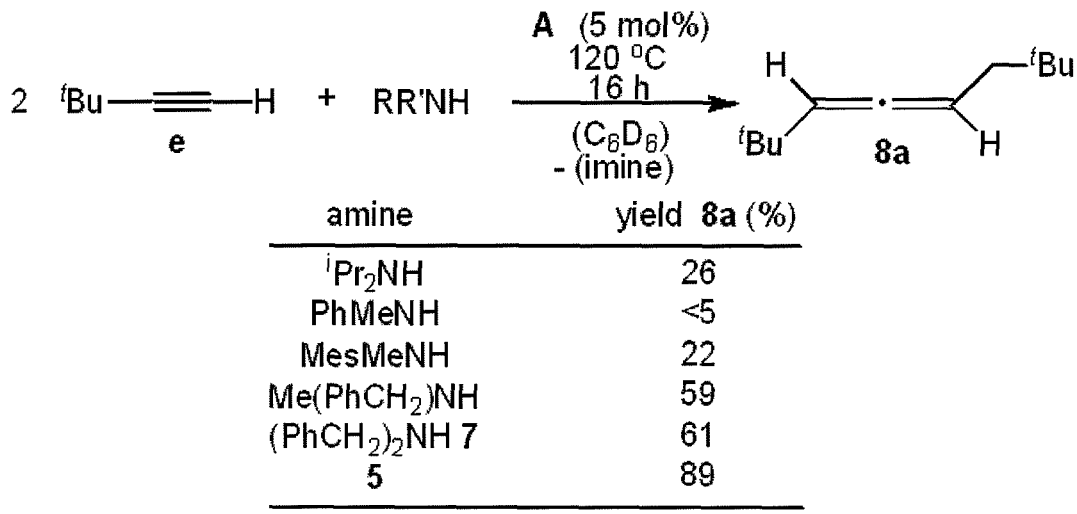
FIG. 9 provides a scheme demonstrating the influence of the amine on the homocoupling of tert-butyl-acetylene.
Figure 10:
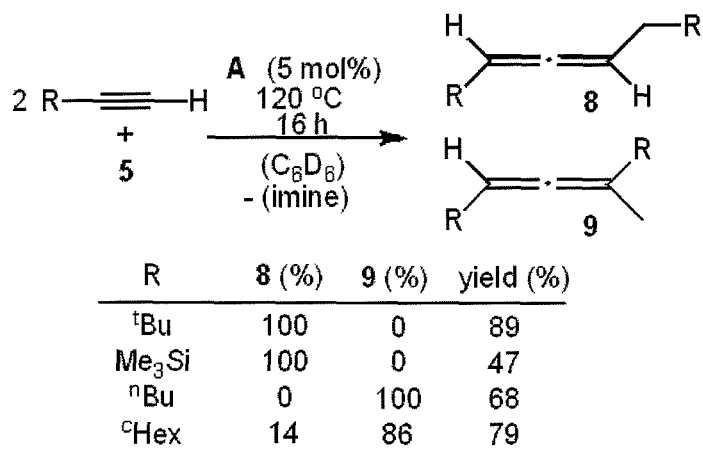
FIG. 10 provides a scheme demonstrating the homocoupling of various alkynes in the presence of 1,2,3,4-tetrahydroisoquinoline 5.

Scheme of FIG. 9 and Scheme of FIG. 10, entry 1 (S9)

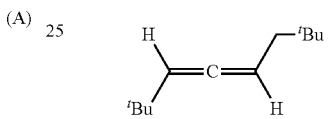

$^1$H NMR (400 MHz, C$_6$D$_6$) δ=5.10 (m, 2H, CH), 1.88 (m, 2H, CH$_2$), 1.02 (s, 9H, CH$_3$), 0.83 (s, 9H, CH$_3$); $^{13}$C NMR (100 MHz, C$_6$D$_6$) δ=203.3 (C$^q$), 102.4 (CH), 90.4 (CH), 45.1 (CH$_2$), 32.3 (C(CH$_3$)$_3$), 31.6 C(CH$_3$)$_3$, 30.9 (CH$_3$), 29.6 (CH$_3$); GCMS: m/z calcd for C$_{12}$H$_{23}$: 166.17 [M+H]$^+$; found: 167.

Scheme of FIG. 10, entry 2 (S10)

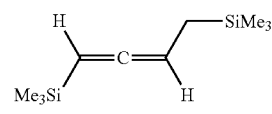

$^1$H NMR (400 MHz, C$_6$D$_6$) δ=4.89 (m, 1H, CH), 4.66 (m, J=6.8 Hz, 1H, CH), 1.48 (d, 1H, $^3J$=7.2 Hz, CH$_2$), 1.47 (d, 1H, $^3J$=6.8 Hz, CH$_2$), 0.09 (s, 9H, CH$_3$), 0.05 (s, 9H, CH$_3$); $^{13}$C NMR (100 MHz, C$_6$D$_6$) δ=211.9 (C$^q$), 82.6 (CH), 78.5 (CH), 13.6 (CH$_2$), 0.3 (CH$_3$), −0.5 (CH$_3$).

Scheme of FIG. 10, entry 3 (S11)

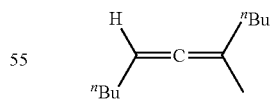

$^1$H NMR (400 MHz, C$_6$D$_6$) δ=5.11 (m, J=3.2 Hz, 1H, CH), 1.99 (dt, $^3J$=7.2 Hz, $^3J$=7.2 Hz, 2H, CH$_2$), 1.92 (dt, $^3J$=7.2 Hz, $^5J$=3.2 Hz, 2H, CH$_2$), 1.67 (d, $^5J$=3.2 Hz, 3H, CH$_3$), 1.45 (tt, $^3J$=7.4 Hz, $^3J$=7.2 Hz, 2H, CH$_2$), 1.41-1.28 (m, 6H, CH$_2$), 0.89 (t, $^3J$=7.2 Hz, 3H, CH$_3$), 0.87 (t, $^3J$=7.0 Hz, 3H, CH$_3$); $^{13}$C NMR (100 MHz, C$_6$D$_6$) δ=202.2 (C$^q$), 99.7 (C$^q$), 90.9 (CH), 34.5 (CH$_2$), 32.3 (CH$_2$), 30.6 (CH$_2$), 29.9 (CH$_2$), 23.1 (CH$_2$), 22.9 (CH$_2$), 19.9 (CH$_3$), 14.6 (CH$_3$), 14.5 (CH$_3$); GCMS: m/z calcd for C$_{12}$H$_{23}$: 166.17 [M+H]$^+$; found: 167.

Scheme of FIG. 10, entry 4

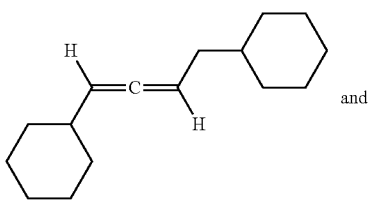

and

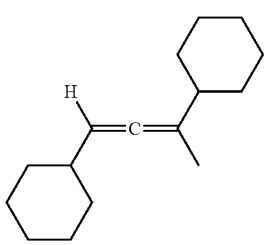

¹H NMR (300 MHz, C₆D₆) δ=5.23 (m, J=2.7 Hz, 2H, CH), 5.20 (q, J=4.8 Hz, 1H, CH), 1.91 (br. td, J=5.7 Hz, J=1.8 Hz, 2H), 1.84-1.52 (m, 24H), 1.70 (d, J=2.7 Hz, 3H, CH₃), 1.38-0.8 (m, 20H); ¹³C NMR (75 MHz, CDCl₃) δ=203.3 (C$^q$ (A)), 199.6 (C$^q$ (B)), 105.5 (C$^q$ (B)), 97.2 (CH (B)), 96.5 (CH (A)), 90.3 (CH (A)), 41.9 (CH), 41.0 (CH), 38.4 (CH), 37.9 (CH), 37.6 (CH₂), 33.5 (CH₂), 33.4 (2CH₂), 33.3 (CH₂), 32.4 (CH₂), 32.3 (CH₂), 26.8 (CH₂), 26.7 (CH₂), 26.5 (2CH₂), 26.4 (CH₂), 26.3 (CH₂), 18.1 (CH₃); GCMS: m/z calcd for C₁₆H₂₅: 217.19 [M]⁺; found: 217.

Figure 11:
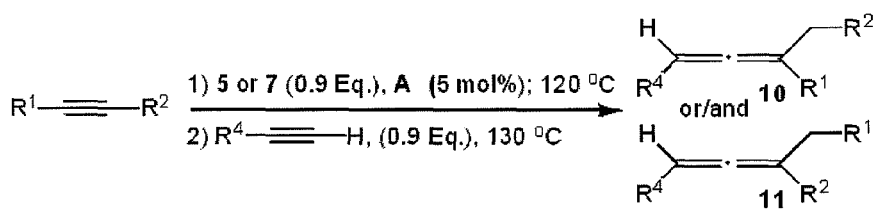
FIG. 11 provides a scheme demonstrating heterocoupling of various alkynes in the presence of 1,2,3,4-tetrahydroisoquinoline 5 or dibenzylamine 7.
Figure 14:
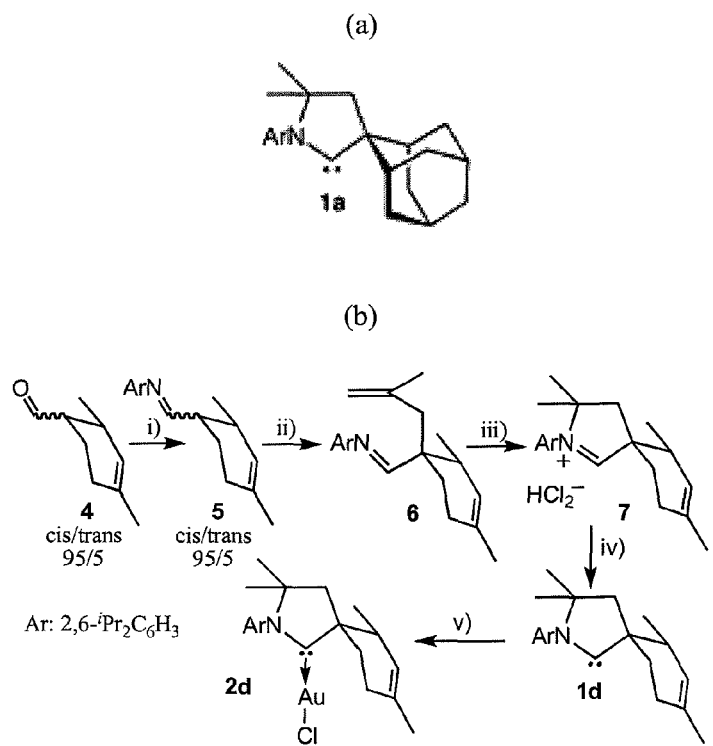

Scheme of FIG. 11, entry 1

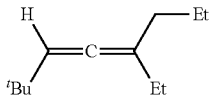

¹H NMR (300 MHz, CDCl₃) δ=5.20 (qn, ⁵J=3.2 Hz, 1H, CH), 2.16 (q, ³J=7.4 Hz, 2H, CH₂), 2.00 (td, ³J=7.3 Hz, ³J=3.2 Hz, 2H, CH₂), 1.52 (tq, ³J=7.4 Hz, ³J=7.4 Hz, 2H, CH₂), 1.13 (t, ³J=7.4 Hz, 3H, CH₃), 1.09 (s, 9H, CH₃), 1.05 (t, ³J=7.4 Hz, 3H, CH₃); ¹³C NMR (75 MHz, CDCl₃) δ=197.3 (C$^q$), 107.7 (C$^q$), 96.3 (CH), 35.3 (CH₂), 32.7 (C(CH₃)₃), 30.5 (CH₃), 25.8 (CH₂), 21.1 (CH₂), 14.1 (CH₃), 12.4 (CH₃); GCMS: m/z calcd for C₁₂H₂₂: 166.17 [M]⁺; found: 166.

Scheme of FIG. 11, entry 2

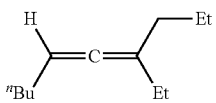

¹H NMR (300 MHz, CDCl₃) δ=5.15-5.08 (tqn, ³J= 6.4 Hz, ⁵J=3.1 Hz, 1H, CH), 2.00-1.90 (m, 6H, CH₂), 1.46 (q, ³J=7.5 Hz, 2H, CH₂), 1.41-1.36 (m, 4H, CH₂), 1.01 (t, ³J=7.4 Hz, 3H, CH₃), 0.93 (t, ³J=7.3 Hz, 3H, CH₃), 0.92 (t, ³J=7.0 Hz, 3H, CH₃); ¹³C NMR (75 MHz, CDCl₃) δ=200.6 (C$^q$), 105.9 (C$^q$), 92.4 (CH), 35.2 (CH₂), 31.9 (CH₂), 29.5 (CH₂), 25.8 (CH₂), 22.5 (CH₂), 21.1 (CH₂), 14.2 (CH₃), 14.1 (CH₃), 12.5 (CH₃); GCMS: m/z calcd for C₁₂H₂₃: 167.18 [M+H]⁺; found: 167.

Scheme of FIG. 11, entry 3

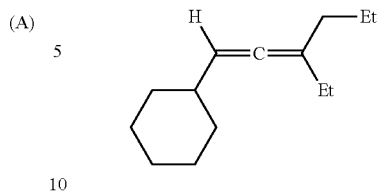

¹H NMR (300 MHz, CDCl₃) δ=5.10 (dqn, ³J=5.9 Hz, ⁵J=3.0 Hz, 1H, CH), 1.94-1.88 (m, 5H, CH₂, CH), 1.72-1.69 (m, 8H, CH₂), 1.43 (qt, J=7.4 Hz, 4H, CH₂), 0.99 (t, J=7.3 Hz, 3H, CH₃), 0.92 (t, J=7.3 Hz, 3H, CH₃); ¹³C NMR (75 MHz, CDCl₃) δ=199.2 (C$^q$), 106.9 (C$^q$), 98.7 (CH), 38.1 (CH), 35.3 (CH₂), 33.6 (CH₂), 26.5 (CH₂), 26.4 (CH₂), 25.9 (CH₂), 21.2 (CH₂), 14.2 (CH₃), 12.5 (CH₃); GCMS: m/z calcd for C₁₄H₂₄: 192.18 [M]⁺; found: 192.

Scheme of FIG. 11, entry 4

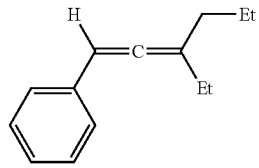 [SMILES: CCCC(=C=Cc1ccccc1)CC]

¹H NMR (300 MHz, CDCl₃) δ=7.34-7.32 (m, 4H, CH), 7.25-7.18 (m, 1H, CH), 6.21 (qn, ⁵J=3.1 Hz, 1H, CH), 2.13 (t, ³J=7.4 Hz, 2H, CH₂), 2.13 (q, ³J=7.3 Hz, 2H, CH₂), 1.56 (tq, ³J=7.4 Hz, ³J=7.3 Hz, 2H, CH₂), 1.11 (t, ³J=7.3 Hz, 3H, CH₃), 0.99 (t, ³J=7.3 Hz, 3H, CH₃); ¹³C NMR (75 MHz, CDCl₃) δ=202.2 (C$^q$), 136.4 (C$^q$), 128.6 (CH), 126.5 (2 CH), 110.5 (C$^q$), 96.0 (CH), 35.1 (CH₂), 26.0 (CH₂), 21.8 (CH₂), 14.0 (CH₃), 12.5 (CH₃); GCMS: m/z calcd for C₁₄H₁₈: 186.14 [M]⁺; found: 186.

Scheme of FIG. 11, entry 5

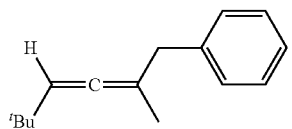

¹H NMR (400 MHz, C₆D₆) δ=7.11-7.00 (m, 5H, CH), 5.03 (m, J=2.4 Hz, 1H, CH), 3.14 (dd, ²J=10.4 Hz, ⁵J=2.4 Hz, 2H, CH₂), 1.58 (d, ⁵J=3.2 Hz, 3H, CH₃), 0.94 (s, 9H, CH₃); ¹³C NMR (100 MHz, C₆D₆) δ=200.2 (C$^{q1}$), 140.4 (C$^q$), 129.8 (CH), 128.8 (CH), 126.8 (CH), 103.1 (CH), 97.2 (C$^q$), 42.2 (CH₂), 32.6 (C(CH₃)₃), 30.7 (CH₃), 19.4 (CH₃); GCMS: m/z calcd for C₁₅H₂₀: 200.16 [M]⁺; found: 200.

Scheme of FIG. 11, entry 6

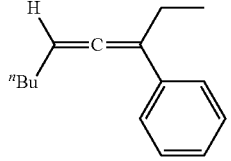

¹H NMR (400 MHz, CDCl₃) δ=7.34-7.19 (m, 5H, CH), 5.05 (qn, ⁵J=4.8 Hz, 1H, CH), 1.97-1.91 (m, 4H, CH₂), 1.37-

1.31 (m, 4H, CH$_2$), 0.99-0.91 (m, 6H, CH$_3$); $^{13}$C NMR (100 MHz, CDCl$_3$) δ=201.3 (C$^q$), 139.4 (C$^q$), 129.6 (CH), 129.0 (CH), 127.3 (CH), 99.3 (C$^q$), 91.1 (CH), 31.7 (CH$_2$), 30.0 (CH$_2$), 29.3 (CH$_2$), 22.4 (CH$_2$), 19.5 (CH$_3$), 14.2 (CH$_3$); GCMS: m/z calcd for C$_{15}$H$_2$O: 200.16 [M]$^+$; found: 200.

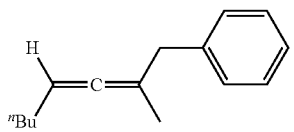

$^1$H NMR (400 MHz, CDCl$_3$) δ=7.32-7.18 (m, 5H, CH), 4.98 (m, 1H, CH), 3.26 (d, $^5$J=2.2 Hz, 2H, CH$_2$), 1.96-1.92 (m, 214, CH$_2$), 1.61 (d, $^5$J=2.4 Hz, 3H, CH$_3$), 1.36-1.30 (m, 4H, CH$_2$), 0.99-0.91 (t, $^3$J=7.1 Hz, 314, CH$_3$); $^{13}$C NMR (100 MHz, CDCl$_3$) δ=202.6 (C$^q$), 140.2 (C$^q$), 129.1 (CH), 128.3 (CH), 126.2 (CH), 98.7 (C$^q$), 90.2 (CH), 41.7 (CH$_2$), 31.6 (CH$_2$), 29.2 (CH$_2$), 22.3 (CH$_2$), 18.8 (CH$_3$), 14.1 (CH$_3$); GCMS: m/z calcd for C$_{15}$H$_2$O: 200.16 [M]$^+$; found: 200.

Scheme of FIG. 11, entry 7

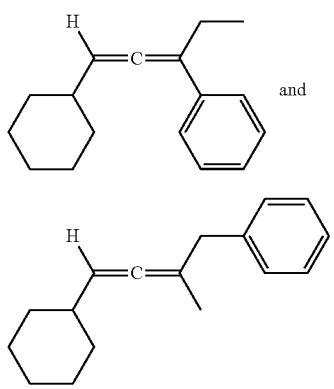

$^1$H NMR (400 MHz, CDCl$_3$) δ=7.31-7.26 (m, 6H), 7.23-7.18 (m, 4H), 5.04 (m, J=3.2 Hz, 1H, CH), 5.00 (m, J=2.6 Hz, 1H, CH), 3.28 (br. s, 2H, CH$_2$(B)), 1.95 (m, 1H, CH), 1.90 (m, 1H, CH), 1.81-1.70 (m, 10H), 1.69 (m, J=2.6 Hz, 4H, CH$_2$), 1.65 (m, J=3.2 Hz, 3H, CH$_3$), 1.39-1.03 (m, 8H), 0.91 (br. t, 3H, CH$_3$(A)); $^{13}$C NMR (75 MHz, CDCl$_3$) δ=204.1 (C$^q$), 201.2 (C$^q$), 140.0 (C$^q$), 138.1 (C$^q$), 129.0 (CH), 128.6 (CH), 128.2 (CH), 128.1 (CH), 126.5 (CH), 126.0 (CH), 101.3 (C$^q$), 99.5 (C$^q$), 96.3 (CH), 95.5 (CH), 41.6 (CH$_2$), 39.2 (CH), 37.8 (CH), 34.7 (CH$_2$), 32.8 (CH$_2$), 32.4 (CH$_2$), 32.0 (CH$_2$), 31.7 (CH$_2$), 26.1 (CH$_2$), 25.9 (CH$_2$), 18.8 (CH$_3$), 14.2 (CH$_3$); GCMS: m/z calcd for C$_{17}$H$_{22}$: 226.17 [M]$^+$; found: 226.

Example 7

Hydroamination of Allenes

All reactions were performed under an atmosphere of argon and C$_6$D$_6$ was dried over Na metal. Reagents were of analytical grade, obtained from commercial suppliers and used without further purification. $^1$H NMR, and $^{13}$C NMR spectra were obtained with Bruker Advance 300 and 500 spectrometers at 298 K. $^1$H and $^{13}$C chemical shifts (δ) are reported in parts per million (ppm) referenced to TMS, and were measured relative to the residual solvent peak. NMR multiplicities are abbreviated as follows: s=singlet, d=doublet, t=triplet, sept.=septet, m=multiplet, br=broad signal. Coupling constants J are given in Hz. Electrospray ionization (ESI) mass spectra were obtained at the UC Riverside Mass Spectrometry Laboratory.

Allenes and amines are commercially available from Sigma-Aldrich and Acros Organics. (CAAC)AuCl and (CAAC)Au(toluene)$^+$B(C$_6$F$_5$)$_4$ (Cat2) were prepared according to the literature (S1). The spectroscopic data observed for the products of Table of FIG. 12, entry 4 (S2) and entry 9 (S3), and of Table of FIG. 13, entry 1 (S4), entry 2 (S5), entry 3 (minor product) (S6), entry 4 (S7), entry 9 (S8), entry 10 (S9), and entry 11 (S10) are identical to those reported in the literature.

Table of FIG. 12, entry 1

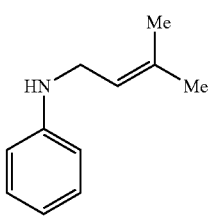

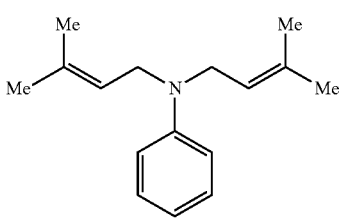

$^1$H NMR (300 MHz, CDCl$_3$): δ=7.29 (t, $^3$J=7.6 Hz, 4H, CH), 6.84-6.79 (m, 4H, CH), 6.72 (dd, J=0.8 Hz, $^3$J=7.7 Hz, 2H, CH), 5.45 (t, J=6.2 Hz, 2H, CH), 5.34 (t, J=5.8 Hz, 1H, CH), 3.98 (d, J=6.1 Hz, 4H, CH$_2$), 3.79 (d, J=6.6 Hz, 2H, CH$_2$), 3.58 (s, 1H, NH), 1.87-1.81 (t, 18H, CH$_3$); $^{13}$C NMR (75 MHz, CDCl$_3$): δ=149.2 (C$^q$), 148.6 (C$^q$), 135.6 (C$^q$), 134.1 (C$^q$), 129.3 (CH), 129.2 (CH), 121.9 (CH), 121.8 (CH), 117.4 (CH), 116.2 (CH), 113.0 (CH), 112.9 (CH), 48.3 (CH$_2$), 42.1 (CH$_2$), 25.9 (CH$_3$), 25.8 (CH$_3$), 18.1 (CH$_3$), 18.0 (CH$_3$); HRMS (ESI) (a): m/z calcd for C$_{11}$H$_{16}$N, 162.1283 [M+H]$^+$; found: 162.1272; HRMS (ESI) (b): m/z calcd for C$_{16}$H$_{24}$N, 230.1909 [M+H]$^+$; found: 230.1899.

Table of FIG. 12, entry 2

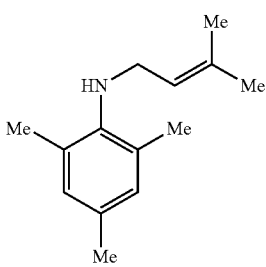 [SMILES: CC(C)=CCNc1c(C)cc(C)cc1C]

$^1$H NMR (300 MHz, CDCl$_3$): δ=6.88 (s, 2H, CH), 5.48-5.42 (m, 1H, CH), 3.54 (d, J=7.0 Hz, 2H, CH$_2$), 2.72 (s, 1H, NH), 2.32 (s, 6H, CH$_3$), 2.29 (s, 3H, CH$_3$), 1.79 (s, 3H, CH$_3$), 1.72 (s, 3H, CH$_3$); $^{13}$C NMR (75 MHz, CDCl$_3$): δ=143.8 (C$^q$), 134.9 (C$^q$), 131.4 (C$^q$), 129.9 (C$^q$), 129.5 (CH), 123.0

(CH), 46.8 (CH$_2$), 25.9 (CH$_3$), 20.7 (CH$_3$), 18.5 (CH$_3$), 17.9 (CH$_3$); HRMS (ESI): m/z calcd for C$_{14}$H$_{22}$N, 204.1752 [M+H]$^+$; found: 204.1742.

Table of FIG. 12, entry 3

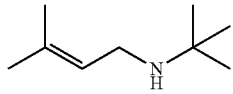

$^1$H NMR (300 MHz, C$_6$D$_6$): δ=5.53-5.47 (m, 1H, CH), 3.27 (d, J=6.6 Hz, 2H, CH$_2$), 2.94 (s, 1H, CHN), 1.76 (s, 3H, CH$_3$), 1.67 (s, 3H, CH$_3$), 1.14 (s, 9H, CH$_3$); $^{13}$C NMR (75 MHz, CDCl$_3$): δ=132.7 (C$^q$), 125.7 (CH), 50.4 (C$^q$), 41.1 (CH$_2$), 29.6 (CH$_3$), 26.1 (CH$_3$), 18.1 (CH$_3$); HRMS (ESI): m/z calcd for C$_9$H$_{20}$N, 142.1596 [M+H]$^+$; found: 142.1589.

Table of FIG. 12, entry 5

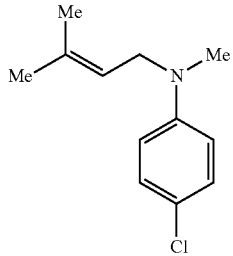 [SMILES: CC(C)=CCN(C)c1ccc(Cl)cc1]

$^1$H NMR (300 MHz, CDCl$_3$): δ=7.20 (d, J=8.9 Hz, 2H, CH), 6.67 (d, J=9.0 Hz, 2H, CH), 5.24-5.19 (m, 1H, CH), 3.90 (d, J=6.3 Hz, 2H, CH$_2$), 2.91 (s, 3H, CH$_3$), 1.77 (d, J=2.7 Hz, 6H, CH$_3$); $^{13}$C NMR (75 MHz, CDCl$_3$): δ=148.5 (C$^q$), 135.1 (C$^q$), 128.9 (CH), 121.3 (C$^q$), 120.5 (CH), 114.1 (CH), 50.7 (CH$_2$), 38.2 (CH$_3$), 25.8 (CH$_3$), 18.1 (CH$_3$); HRMS (ESI): m/z calcd for C$_{12}$H$_{17}$NCl: 210.1050 [M+H]$^+$; found: 210.1050.

Table of FIG. 12, entry 6

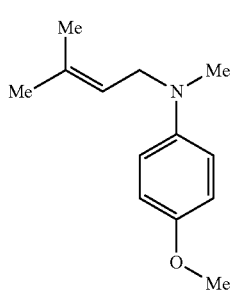 [SMILES: COc1ccc(N(C)CC=C(C)C)cc1]

$^1$H NMR (300 MHz, CDCl$_3$): δ=6.88 (d, J=9.2 Hz, 2H, CH), 6.80 (d, J=9.1 Hz, 2H, CH), 5.29-5.14 (m, 1H, CH), 3.84 (d, J=6.4 Hz, 2H, CH$_2$), 3.80 (s, 3H, CH$_3$), 2.85 (s, 3H, CH$_3$), 1.76 (dd, J=1.0 Hz, J=5.7 Hz, 6H, CH$_3$); $^{13}$C NMR (75 MHz, CDCl$_3$): δ=152.0 (C$^q$), 145.0 (C$^q$), 134.7 (C$^q$), 121.1 (CH), 115.6 (CH), 114.7 (CH), 55.8 (CH$_3$), 51.9 (CH$_2$), 38.9 (CH$_3$), 25.8 (CH$_3$), 18.0 (CH$_3$); HRMS (ESI): m/z calcd for C$_{13}$H$_{20}$NO: 206.1545 [M+H]$^+$; found: 206.1546.

Table of FIG. 12, entry 7

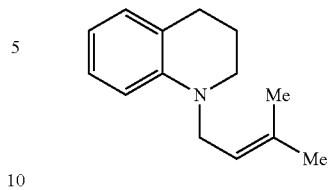

$^1$H NMR (300 MHz, CDCl$_3$): δ=7.17 (t, $^3$J=7.7 Hz, 1H, CH), 7.08 (d, $^3$J=7.1 Hz, 1H, CH), 6.74-6.68 (m, 2H, CH), 5.40-5.35 (m, 1H, CH), 3.99 (d, J=6.3 Hz, 2H, CH$_2$), 3.38 (t, J=5.7 Hz, 2H, CH$_2$), 2.89 (t, J=6.3 Hz, 2H, CH$_2$), 2.09 (t, J=5.8 Hz, 2H, CH$_2$), 1.87 (d, J=1.1 Hz, 6H, CH$_3$); $^{13}$C NMR (75 MHz, CDCl$_3$): δ=145.7 (C$^q$), 134.5 (C$^q$), 129.2 (CH), 127.1 (CH), 122.9 (C$^q$), 121.1 (CH), 115.8 (CH), 111.2 (CH), 49.2 (CH$_2$), 49.0 (CH$_2$), 28.2 (CH$_2$), 25.8 (CH$_3$), 22.5 (CH$_2$), 18.1 (CH$_3$); HRMS (ESI): m/z calcd for C$_{14}$H$_{20}$N, 202.1596 [M+H]$^+$; found: 202.1590.

Table of FIG. 12, entry 8

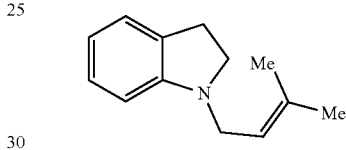

$^1$H NMR (300 MHz, CDCl$_3$): δ=7.14 (t, $^3$J=7.5 Hz, 2H, CH), 6.74 (t, $^3$J=7.2 Hz, 1H, CH), 6.60 (d, $^3$J=7.8 Hz, 1H, CH), 5.42-5.37 (m, 1H, CH), 3.77 (d, J=6.8 Hz, 2H, CH$_2$), 3.38 (t, J=8.2 Hz, 2H, CH$_2$), 3.00 (t, J=8.2 Hz, 2H, CH$_2$), 1.82 (d, J=9.2 Hz, 6H, CH$_3$); $^{13}$C NMR (75 MHz, CDCl$_3$): δ=152.6 (C$^q$), 135.4 (C$^q$), 130.6 (C$^q$), 127.3 (CH), 124.5 (CH), 120.3 (CH), 117.7 (CH), 107.5 (CH), 53.2 (CH$_2$), 46.8 (CH$_2$), 28.7 (CH$_2$), 25.9 (CH$_3$), 18.1 (CH$_3$); HRMS (ESI): m/z calcd for C$_{13}$H$_{18}$N, 188.1439 [M+H]$^+$; found: 188.1438.

Table of FIG. 12, entry 10

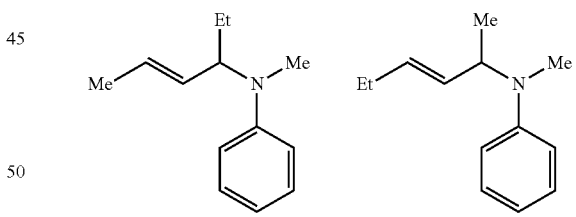

$^1$H NMR (300 MHz, CDCl$_3$): δ=7.23-7.20 (m, 2H, CH), 7.11 (dt, J=1.4 Hz, $^3$J=7.3 Hz, 2H, CH), 7.08-7.01 (m, 1H, CH), 6.78 (t, $^3$J=7.3 Hz, 2H, CH), 6.67 (d, $^3$J=7.9 Hz, 2H, CH), 6.60 (d, $^3$J=7.9 Hz, 1H, CH), 5.56-5.53 (m, 2H, CH), 5.49-5.46 (m, 2H, CH), 3.43-3.37 (m, 1H, CH), 3.09-5.05 (m, 1H, CH), 2.87 (s, 3H, CH$_3$), 2.84 (s, 3H, CH$_3$), 2.08-2.03 (m, 2H, CH$_2$), 1.85-1.67 (m, 5H, CH$_2$, CH$_3$), 1.40 (d, $^3$J=7.0 Hz, 3H, CH$_3$), 1.02-0.86 (m, 6H, CH$_3$); $^{13}$C NMR (75 MHz, CDCl$_3$): δ=147.8 (C$^q$), 147.1 (C$^q$), 134.1 (CH), 133.2 (CH), 131.8 (CH), 127.2 (CH), 126.6 (cm, 117.4 (CH), 117.3 (CH), 112.7 (CH), 110.5 (CH), 110.3 (CH), 44.8 (CH), 37.1 (CH), 31.1 (CH$_3$), 30.9 (CH$_3$), 26.9 (CH$_2$), 25.7 (CH$_2$), 19.8 (CH$_3$), 18.1 (CH$_3$), 14.1 (CH$_3$), 12.6 (CH$_3$); HRMS (ESI): m/z calcd for C$_{13}$H$_{20}$N, 190.1596 [M+H]$^+$; found: 190.1596.

Table of FIG. 13, entry 3

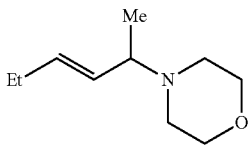 [SMILES: CC/C=C/C(C)N1CCOCC1]

$^1$H NMR (300 MHz, C$_6$D$_6$): δ=5.47-5.33 (m, 2H, CH), 3.64 (t, J=4.6 Hz, 4H, CH$_2$), 2.74-2.65 (m, 1H, CHN), 2.35 (t, J=4.7 Hz, 4H, CH$_2$), 1.95-1.91 (m, 2H, CH$_2$), 1.05 (d, J=6.4 Hz, 3H, CH$_3$), 0.91 (t, J=7.4 Hz, 3H, CH$_3$); $^{13}$C NMR (75 MHz, C$_6$D$_6$): δ=133.8 (CH), 132.0 (CH), 67.8 (CH$_2$), 63.1 (CH), 51.1 (CH$_2$), 26.1 (CH$_2$), 18.3 (CH$_3$), 14.3 (CH$_3$); HRMS (ESI): m/z calcd for C$_{10}$H$_{20}$NO: 170.1545 [M+H]$^+$; found: 170.1542.

Table of FIG. 13, entry 5

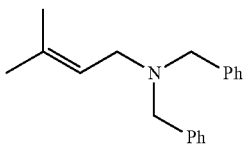 [SMILES: CC(C)=CCN(Cc1ccccc1)Cc1ccccc1]

$^1$H NMR (300 MHz, CDCl$_3$): δ=7.51 (d, $^3$J=7.3 Hz, 4H, CH), 7.43 (t, $^3$J=7.6 Hz, 4H, CH), 7.34 (t, $^3$J=7.1 Hz, 2H, CH), 5.49-5.44 (m, 1H, CH), 3.69 (s, 4H, CH$_2$), 3.14 (d, J=6.6 Hz, 2H, CH$_2$), 1.85 (s, 3H, CH$_3$), 1.70 (s, 3H, CH$_3$); $^{13}$C NMR (75 MHz, CDCl$_3$): δ=140.1 (C$^q$), 134.9 (C$^q$), 128.9 (CH), 128.3 (CH), 126.8 (CH), 122.1 (CH), 58.1 (CH$_2$), 51.2 (CH$_2$), 26.1 (CH$_3$), 18.2 (CH$_3$); HRMS (ESI): m/z calcd for C$_{19}$H$_{24}$N, 266.1909 [M+H]$^+$; found: 266.1914.

Table of FIG. 13, entry 6

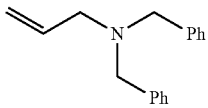 [SMILES: C=CCN(Cc1ccccc1)Cc1ccccc1]

$^1$H NMR (300 MHz, CDCl$_3$): δ=7.54 (d, $^3$J=6.8 Hz, 4H, CH), 7.50-7.44 (m, 4H, CH), 7.40-7.35 (m, 2H, CH), 6.14-6.01 (m, 1H, CH), 5.41-5.29 (m, 2H, CH$_2$), 3.74 (s, 4H, CH$_2$), 3.23 (dt, J=1.1 Hz, J=6.3 Hz, 2H, CH$_2$); $^{13}$C NMR (75 MHz, CDCl$_3$): δ=139.7 (C$^q$), 136.1 (CH), 128.8 (CH), 128.3 (CH), 126.9 (CH), 117.4 (CH$_2$), 57.8 (CH$_2$), 56.4 (CH$_2$); HRMS (ESI): m/z calcd for C$_{17}$H$_{20}$N, 238.1596 [M+H]$^+$; found: 238.1600.

Table of FIG. 13, entry 7

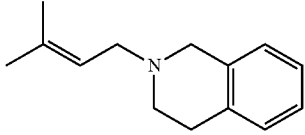

$^1$H NMR (300 MHz, CDCl$_3$): δ=7.16-7.10 (m, 3H, CH), 7.06-7.03 (m, 1H, CH), 5.43-5.38 (m, 1H, CH), 3.66 (s, 2H, CH$_2$), 3.17 (d, J=6.9 Hz, 2H, CH$_2$), 2.94 (t, J=5.8 Hz, 2H, CH$_2$), 2.76 (t, J=5.7 Hz, 2H, CH$_2$), 1.82 (s, 3H, CH$_3$), 1.74 (s, 3H, CH$_3$); $^{13}$C NMR (75 MHz, CDCl$_3$): δ=135.3 (C$^q$), 135.0 (C$^q$), 134.4 (C$^q$), 128.7 (CH), 126.6 (CH), 126.1 (CH), 125.5 (CH), 121.3 (CH), 56.2 (CH$_2$), 56.0 (CH$_2$), 50.7 (CH$_2$), 29.3 (CH$_2$), 26.0 (CH$_3$), 18.2 (CH$_3$); HRMS (ESI): m/z calcd for C$_{14}$H$_{20}$N, 202.1596 [M+H]$^+$; found: 202.1596.

Table of FIG. 13, entry 8

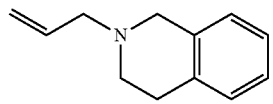

$^1$H NMR (300 MHz, CDCl$_3$): δ=7.18-7.10 (m, 3H, CH), 7.06-7.03 (m, 1H, CH), 6.07-5.93 (m, 1H, CH), 5.34-5.22 (m, 2H, CH$_2$), 3.66 (s, 2H, CH$_2$), 3.21 (dt, J=1.2 Hz, J=6.5 Hz, 2H, CH$_2$), 2.95 (t, J=5.8 Hz, 2H, CH$_2$), 2.78 (t, J=5.9 Hz, 2H, CH$_2$); $^{13}$C NMR (75 MHz, CDCl$_3$): δ=135.5 (CH), 134.9 (C$^q$), 134.4 (C$^q$), 128.8 (CH), 126.7 (CH), 126.2 (CH), 125.7 (CH), 118.0 (CH$_2$), 61.6 (CH$_2$), 56.2 (CH$_2$), 50.7 (CH$_2$), 29.2 (CH$_2$); HRMS (ESI): m/z calcd for C$_{12}$H$_{16}$N, 174.1283 [M+H]$^+$; found: 174.1272.

Example 8

Preparation of Dihydroisoquinolines Via Hydroamination

General Considerations: All reactions were performed under an atmosphere of argon by using standard Schlenk or dry box techniques. Solvents were dried over Na metal or CaH$_2$. Reagents were of analytical grade, obtained from commercial suppliers and used without further purification. $^1$H NMR, and $^{13}$C NMR spectra were obtained with a Bruker Advance 300 spectrometer at 298 K. $^1$H and $^{13}$C chemical shifts (δ) are reported in parts per million (ppm) referenced to TMS, and were measured relative to the residual solvent peak. NMR multiplicities are abbreviated as follows: s=singlet, d=doublet, t=triplet, sept.=septet, m=multiplet, br=broad signal. Coupling constants J are given in Hz. Electrospray ionization (ESI) mass spectra were obtained at the UC Riverside Mass Spectrometry Laboratory. Melting points were measured with a Büchi melting point apparatus system. The Bruker X8-APEX (S$^{xvii}$) X-ray diffraction instrument with Mo-radiation was used for data collection.

Arylamines and alkynes are commercially available from Sigma-Aldrich and Acros Organics. Gold complex 2a and KB(C$_6$F$_5$)$_4$ were prepared according to the literature (Lavallo, V.; Frey, G. D.; Kousar, S.; Donnadieu, B.; Bertrand, G. Proc. Natl. Acad. Sci. USA 2007, 104, 13569-13573). The spectroscopic data observed for the products of hydroamination of internal alkynes with Et$_2$NH (Table 1) are identical to those reported in the literature (Zeng, X.; Frey, G. D.; Kousar, S.; Bertrand, G. Chem. Eur. J 2009, 15, 3056-3060).

Synthesis of compound 5. 2,6-Diisopropylaniline (10.00 mL, 9.40 g, 53.0 mmol) was added at room temperature to a reaction flask containing molecular sieves (15 g) and a toluene solution (25 mL) of trivertal 4 (8.05 mL, 7.54 g, 54.6 mmol). The reaction mixture was stirred for 16 h at 100° C. Molecular sieves were removed by filtration, and toluene was removed under vacuum. Excess of trivertal 4 was removed by a short path distillation at 60° C. under high vacuum to afford 14.57 g of imine 5 as a yellow oil (94% yield). $^1$H NMR (300 MHz, CDCl$_3$): δ=7.83 (d, $^3$J=5.6 Hz, 1H, NCH$^{trans}$), 7.73 (d, $^3$J=5.4 Hz, 1H, NCH$^{cis}$), 7.29-7.18 (m, 3H, CH), 5.52 (s, 1H, CH$^{trans}$), 5.46 (s, 1H, CH$^{cis}$), 3.13 (sept, $^3$J=6.8 Hz, 2H, CH(CH$_3$)$_2$), 2.63-2.55 (m, 1H, CH), 2.46-2.41 (m, 1H, CH), 2.21-2.14 (m, 4H, CH$_2$), 1.87 (s, 3H, CH$_3$$^{cis}$), 1.83 (s, 3H, CH$_3^{trans}$), 1.44 (d, $^3J$=6.7 Hz, 3H, CH$_3^{trans}$), 1.33 (d, $^3J$=6.8 Hz, 12H, CH$_3^{cis}$); $^{13}$C NMR (75 MHz, CDCl$_3$): δ=170.9 (NCH$^{cis}$), 170.2 (NCH$^{trans}$), 149.1 (C$^q$), 137.7 (C$^q$), 133.3 (C$^q$), 127.0 (CH$^{trans}$); 126.5 (CH$^{cis}$), 124.0 (CH$^{cis}$), 123.7 (CH$^{trans}$); 122.9 (CH), 48.0 (CH$^{cis}$), 44.6 (CH$^{trans}$), 32.8 (CH$^{cis}$), 32.2 (CH$^{trans}$), 29.1 (CH$_2^{cis}$), 28.4 (CH$_2^{trans}$), 28.0 (CH$^{trans}$), 27.7 (CH$^{cis}$), 25.8 (CH$_2$), 23.6 (CH$_3^{cis}$), 22.6 (CH$_3^{trans}$), 20.8 (CH$_3^{cis}$), 18.1 (CH$_3^{trans}$); HRMS (ESI): m/z calcd for C$_{21}$H$_{32}$N, 298.2535 [(M+H)]$^+$; found: 298.2537.

Synthesis of compound 6. A solution of 5 (7.07 g, 23.8 mmol) in Et$_2$O (15 mL) was added slowly to a solution of lithium diisopropylamine (LDA) (2.62 g, 24.5 mmol) in Et$_2$O (30 mL) at −78° C. The mixture was stirred and allowed to warm-up to room temperature, then stirred for an additional 3 h. All volatiles were removed under vacuum, and Et$_2$O (30 mL) was added. After the solution was cooled to −78° C., 3-chloro-2-methyl-1-propene (2.22 g, 2.40 mL, 24.5 mmol) was slowly added under stirring. After stirring for 2 h, all volatiles were removed under vacuum. Hexanes (20 mL) was added and the suspension was filtered via a filter-cannula. The solvent was evaporated to give 7.52 g of compound 6 as a pale yellow oil (90% yield). $^1$H NMR (300 MHz, C$_6$D$_6$): δ=7.70 (s, 11-1, NCH), 7.19-7.09 (m, 3H, CH), 5.22 (s, 1H, CH), 4.99 (s, 1H, CH$_2$), 4.84 (s, 1H, CH$_2$), 3.15 (sept, $^3J$=6.8 Hz, 2H, CH(CH$_3$)$_2$), 2.61 (s, 2H, CH$_2$), 2.50-2.48 (m, 11-1, CH), 1.94-1.84 (m, 4H, CH$_2$), 1.77 (s, 3H, CH$_3$), 1.62 (s, 3H, CH$_3$), 1.23 (d, $^3J$=6.8 Hz, 12H, CH$_3$), 1.04 (d, $^3J$=7.0 Hz, 3H, CH$_3$); $^{13}$C NMR (75 MHz, C$_6$D$_6$): δ=171.0 (NCH), 150.1 (C$^q$), 142.9 (C$^q$), 137.9 (C$^q$), 133.7 (C$^q$), 127.2 (CH), 124.6 (CH), 123.6 (CH), 116.2 (CH$_2$), 45.9 (C$^q$), 43.8 (CH$_2$), 35.8 (CH), 31.3 (CH$_2$), 28.8 (CH$_2$), 28.1 (CH), 24.2 (CH$_3$), 23.6 (CH$_3$), 21.3 (CH$_3$), 17.2 (CH$_3$); HRMS (ESI): m/z calcd for C$_{25}$H$_{38}$N, 352.3004 [(M+H)]$^+$; found: 352.2996.

Synthesis of iminium salt 7. To a solution of 6 (7.52 g, 23.8 mmol) in hexanes (10 mL) was added a solution of HCl in Et$_2$O (2M, 25.0 mL, 50.0 mmol) at −78° C. Precipitation of a white powder was immediately observed. The mixture was warmed to room temperature and stirred for 30 min. Filtration of the precipitate, washing with hexanes (20 mL), and drying under vacuum afforded a white powder. Toluene (25 mL) was added and the reaction mixture heated for 16 h at 110° C. Volatiles were removed under vacuum to afford 7 as a white powder (7.45 g, 74%). Mp: 218° C.; $^1$H NMR (300 MHz, CDCl$_3$): δ=10.67 (br, HCl$_2$), 10.07 (s, 1H, NCH), 7.40 (t, $^3J$=7.7 Hz, 1H, CH), 7.21 (d, $^3J$=7.7 Hz, 2H, CH), 5.25 (s, 1H, CH), 2.53 (sept, $^3J$=6.6 Hz, 2H, CH(CH$_3$)$_2$), 2.49-2.46 (m, 1H), 2.36 (s, 2H), 2.01 (t, $^3J$=6.2 Hz, 2H, CH$_2$), 1.89-1.80 (m, 2H), 1.62 (s, 3H, CH$_3$), 1.48 (s, 3H, CH$_3$), 1.46 (s, 3H, CH$_3$), 1.24 (d, $^3J$=6.6 Hz, 6H, CH$_3$), 1.18-1.13 (m, 6H, CH$_3$), 1.09 (d, $^3J$=6.6 Hz, 3H, CH$_3$); $^{13}$C NMR (75 MHz, CDCl$_3$): δ=193.3 (NCH), 144.6 (C$^q$), 144.0 (C$^q$), 134.0 (C$^q$), 131.9 (CH), 129.1 (C$^q$), 125.4 (CH), 125.3 (CH), 123.9 (CH), 83.0 (C$^q$), 55.1 (C$^q$), 46.1 (CH$_2$), 39.7 (CH), 30.4 (CH$_2$), 30.0 (CH$_3$), 29.9 (CH$_3$), 29.2 (CH), 28.3, 26.8 (CH$_3$), 26.7 (CH$_3$), 26.3 (CH$_2$), 23.4 (CH$_3$), 22.2 (CH$_3$), 18.8 (CH$_3$); HRMS (ESI): m/z calcd for C$_{25}$H$_{38}$N, 352.3004 [M]$^+$; found: 352.3000.

Synthesis of CAAC 1d. To an Et$_2$O solution (10 mL) of iminium salt 7 (1.00 g, 2.36 mmol) was added at −78° C. a solution of LDA (0.51 g, 4.72 mmol) in Et$_2$O (10 mL). The mixture was warmed to room temperature and stirred for 2 h. The solvent was removed in vacuo, and the residue was extracted twice with hexane (10 mL). Removal of the solvent under vacuum afforded 0.79 g of carbene 1d as a white solid (95% yield). $^1$H NMR (300 MHz, C$_6$D$_6$): δ=7.27-7.12 (m, 3H), 5.61 (m, 1H, CH), 3.17 (sept, $^3J$=6.8 Hz, 2H, CH(CH$_3$)$_2$), 3.16 (sept, $^3J$=6.7 Hz, 1H, CH(CH$_3$)$_2$), 2.45-2.37 (m, 1H), 2.32-2.24 (m, 2H), 2.08-1.92 (m, 2H), 1.79 (s, 2H), 1.62 (m, 3H), 1.38 (d, $^3J$=7.2 Hz, 3H, CH$_3$), 1.26 (d, $^3J$=6.9 Hz, 6H, CH$_3$), 1.20 (d, $^3J$=6.7 Hz, 3H, CH$_3$), 1.16-1.14 (m, 9H, CH$_3$); $^{13}$C NMR (75 MHz, C$_6$D$_6$): δ=320.3 (NCC), 146.4 (C$^q$), 146.3 (C$^q$), 138.8 (C$^q$), 133.1 (C$^q$), 128.4 (CH), 128.1 (CH), 124.1 (CH), 81.0 (C$^q$), 65.2 (C$^q$), 48.7 (CH$_2$), 41.1, 33.7 (CH$_2$), 30.0, 29.8, 29.7, 29.4 (CH$_2$), 26.7, 26.6, 24.4, 22.3, 19.3.

Synthesis of complex 2d. A THF solution (5 mL) of the free carbene 1d (390 mg, 1.11 mmol) was added to a THF solution (5 mL) of AuCl(SMe$_2$) (324 mg, 1.10 mmol). The reaction mixture was stirred at room temperature in darkness for 12 h. The solvent was removed under vacuum, and the residue was washed twice with hexane (5 mL). The residue was extracted twice with methylene chloride (10 mL), and the solvent was removed under vacuum, affording complex 2d as a white solid (564 mg, 87% yield). Mp: 240° C.; $^1$H NMR (300 MHz, C$_6$D$_6$): δ=7.11 (m, 1H), 7.01 (m, 2H), 5.37 (s, 1H, CH), 2.68 (sept, $^3J$=6.6 Hz, 2H, CH(CH$_3$)$_2$), 2.49 (m, 1H, CH(CH$_3$)$_2$), 2.11 (s, 1H), 2.09 (m, 2H), 1.83 (s, 3H, CH$_3$), 1.77-1.61 (m, 2H), 1.53 (d, $^3J$=6.5 Hz, 3H, CH$_3$), 1.47 (d, $^3J$=6.6 Hz, 3H, CH$_3$), 1.43-1.38 (m, 1H), 1.23 (d, $^3J$=7.0 Hz, 3H, CH$_3$), 1.12 (d, $^3J$=6.4 Hz, 3H, CH$_3$), 1.10 (d, $^3J$=6.5 Hz, 3H, CH$_3$), 0.91 (s, 3H, CH$_3$), 0.88 (s, 3H, CH$_3$); $^{13}$C NMR (75 MHz, C$_6$D$_6$): δ=240.1 (NCC), 145.5 (C$^q$), 145.4 (C$^q$), 135.8 (C$^q$), 134.1 (C$^q$), 130.4 (CH), 127.0 (CH), 125.5 (CH), 125.3 (CH), 78.1 (C$_q$), 60.3 (C$^q$), 48.1 (CH$_2$), 40.0 (CH), 35.2 (CH$_2$), 29.8 (CH), 29.7 (CH$_2$), 29.6 (CH$_3$), 29.5 (CH), 29.3 (CH$_3$), 27.4 (CH$_3$), 27.3 (CH$_3$), 23.7 (CH$_3$), 23.4 (CH$_3$), 23.0 (CH$_3$), 19.1 (CH$_3$); HRMS (ESI; CH$_3$CN): m/z calcd for C$_{27}$H$_{40}$AuN$_2$: 589.2857 [M-Cl+CH$_3$CN]$^+$; found: 589.2865.

General catalytic procedure for the hydroamination of internal alkynes with Et$_2$NH: In a dried 3-Young-Tube, CAAC(AuCl) complex 2a or 2d (0.025 mmol) and KB(C$_6$F$_5$)$_4$ (0.025 mmol) were loaded under an argon atmosphere. C$_6$D$_6$ (0.4 mL) and the internal standard, benzyl methyl ether, were added and after shaking the tube, the internal alkyne 8 (0.5 mmol) and Et$_2$NH (0.5 mmol) were loaded. The tube was sealed, placed in an oil bath behind a blast shield, and heated at the specified temperature (Table 1). The reaction was monitored by NMR spectroscopy. The products were purified by removal of the solvent and extraction with n-hexane.

General catalytic procedure for the three-component coupling reaction of arylamines 9, internal alkynes 8, and terminal alkynes 10: In a dried 3-Young-Tube, complex 2d (0.025 mmol) and KB(C$_6$F$_5$)$_4$ (0.025 mmol) were loaded under an argon atmosphere. C$_6$D$_6$ (0.4 mL) and the internal standard benzyl methyl ether were added and after shaking the tube, internal alkyne 8 (0.55 mmol) and arylamine 9 (0.5 mmol) were loaded. The tube was sealed, placed in an oil bath behind a blast shield, heated at the corresponding temperature, and the reaction was monitored by NMR spectroscopy. After complete conversion of the reactants, a terminal alkyne 10 (0.5 mmol) was added, and the reaction mixture heated at 100° C. for 24 h. The products were purified by column chromatography.

Characterization of heterocycles 11 (see FIG. 16) resulting from the three-component coupling reactions 11a: $^1$H NMR (300 MHz, CDCl$_3$): δ=7.42-7.36 (m, 5H, CH), 7.09 (td, $^3J$=6.8 Hz, $^4J$=1.5 Hz, 1H, CH), 6.80 (d, $^3J$=7.4 Hz, 1H, CH), 6.49 (t, $^3J$=7.0 Hz, 2H, CH), 5.08 (s, 1H, CH), 2.80 (s, 3H, CH$_3$), 1.36-1.27 (m, 6H, CH$_2$), 1.00 (t, $^3J$=7.4 Hz, 3H, CH$_3$), 0.94 (t, $^3J$=7.2 Hz, 3H, CH$_3$); $^{13}$C NMR (75 MHz, CDCl$_3$): δ=146.8 (C$^q$), 140.3 (C$^q$), 138.5 (C$^q$), 129.3 (CH), 129.2 (CH), 128.3 (CH), 128.1 (CH), 127.3 (CH), 125.8 (CH), 121.0 (C$^o$), 114.9 (CH), 108.8 (CH), 64.1 (C$^q$), 44.2 (CH$_2$), 34.3 (CH$_2$), 30.2 (CH$_3$), 18.2 (CH$_2$), 14.7 (CH$_3$), 9.1

(CH$_3$); HRMS (ESI): m/z calcd for C$_{21}$H$_{26}$N, 292.2065 [M+H]$^+$; found: 292.2064. Mp: 93-94° C.; Crystals suitable for X-ray diffraction study were obtained by slow evaporation of a hexane solution.

11b: $^1$H NMR (300 MHz, C$_6$D$_6$): δ=7.14 (t, J=1.7 Hz, 1H, CH), 7.12 (t, J=1.5 Hz, 1H, CH), 6.68 (dd, $^3$J=7.5 Hz, J=0.8 Hz, 1H, CH), 6.39 (d, $^3$J=7.1 Hz, 1H, CH), 4.78 (s, 1H, CH), 2.38 (s, 3H, CH$_3$), 2.34 (t, $^3$J=7.7 Hz, 2H, CH$_2$), 1.62-1.48 (m, 6H, CH$_2$), 1.39-1.22 (m, 4H, CH$_2$), 1.03-0.81 (m, 9H, CH$_3$); $^{13}$C NMR (75 MHz, CDCl$_3$): δ=147.6 (C$^q$), 135.8 (C$^q$), 129.6 (CH), 125.5 (CH), 123.8 (CH), 121.3 (C$^q$), 115.9 (CH), 109.4 (CH), 63.9 (C$^q$), 44.7 (CH$_2$), 34.8 (CH$_2$), 32.7 (CH$_2$), 31.6 (CH$_2$), 30.2 (CH$_3$), 23.4 (CH$_2$), 18.6 (CH$_2$), 15.1 (CH$_3$), 14.5 (CH$_3$), 9.4 (CH$_3$); HRMS (ESI): m/z calcd for C$_{19}$H$_{30}$N, 272.2378 [M+H]$^+$; found: 272.2381.

11c: $^1$H NMR (300 MHz, C$_6$D$_6$): δ=7.37 (dd, $^3$J=7.9 Hz, J=1.6 Hz, 4H, CH), 7.19-7.03 (m, 7H, CH), 6.60 (t, $^3$J=7.5 Hz, 2H, CH), 6.52 (d, $^3$J=8.2 Hz, 1H, CH), 5.18 (s, 1H, CH), 2.89 (d, $^2$J=12.9 Hz, 1H, CH$_2$), 2.54 (s, 3H, CH$_3$), 2.49 (d, $^2$J=12.9 Hz, 1H, CH$_2$), 1.26 (s, 3H, CH$_3$); $^{13}$C NMR (75 MHz, C$_6$D$_6$): δ=146.5 (C$^q$), 140.8 (C$^q$), 138.2 (C$^q$), 137.5 (C$^q$), 131.4 (CH), 129.8 (CH), 129.7 (CH), 129.7 (CH), 128.8 (CH), 128.6 (CH), 128.2 (CH), 127.8 (CH), 126.7 (CH), 120.7 (C$^q$), 117.1 (CH), 112.0 (CH), 59.9 (C$^q$), 44.3 (CH$_2$), 31.4 (CH$_3$), 27.5 (CH$_3$); HRMS (ESI): m/z calcd for C$_{24}$H$_{24}$N, 326.1909 [M+H]$^+$; found: 326.1913.

11d: $^1$H NMR (300 MHz, C$_6$D$_6$): δ=7.28 (dd, $^3$J=7.9 Hz, $^4$J=1.9 Hz, 2H, CH), 7.14-7.06 (m, 4H, CH), 6.73 (td, $^3$J=7.4 Hz, $^4$J=1.8 Hz, 2H, CH), 6.48 (d, $^3$J=8.3 Hz, 1H, CH), 5.04 (s, 1H, CH), 2.90 (d, $^2$J=12.8 Hz, 1H, CH$_2$), 2.51 (s, 3H, CH$_3$), 2.45 (d, $^2$J=12.3 Hz, 1H, CH$_2$), 2.28 (t, $^3$J=7.8 Hz, 2H, CH$_2$), 1.49-1.43 (m, 4H, CH$_2$), 1.24 (s, 3H, CH$_3$), 0.84 (t, $^3$J=7.2 Hz, 3H, CH$_3$); $^{13}$C NMR (75 MHz, C$_6$D$_6$): δ=146.4 (C$^q$), 138.5 (C$^q$), 134.0 (C$^q$), 131.3 (CH), 129.3 (CH), 128.2 (CH), 127.7 (CH), 126.6 (CH), 123.8 (CH), 121.9 (C$^q$), 116.9 (CH), 111.7 (CH), 59.9 (C$^q$), 45.1 (CH$_2$), 32.4 (CH$_2$), 31.4 (CH$_3$), 31.3 (CH$_2$), 27.5 (CH$_3$), 23.4 (CH$_2$), 14.5 (CH$_3$); HRMS (ESI): m/z calcd for C$_{22}$H$_{28}$N, 306.2222 [M+H]$^+$; found: 306.2217.

11e: $^1$H NMR (300 MHz, C$_6$D$_6$): δ=7.19 (d, J=1.7 Hz, 1H, CH), 7.07 (dd, J=8.4 Hz, J=1.6 Hz, 1H, CH), 6.07 (d, J=8.6 Hz, 1H, CH), 4.72 (s, 1H, CH), 2.23 (s, 3H, CH$_3$), 2.14 (t, $^3$J=7.5 Hz, 2H, CH$_2$), 1.49-1.35 (m, 6H, CH$_2$), 1.28-1.16 (m, 4H, CH$_2$), 0.96-0.82 (m, 9H, CH$_3$); $^{13}$C NMR (75 MHz, CDCl$_3$): δ=146.0 (C$^q$), 134.9 (C$^q$), 129.7 (C$^q$), 128.7 (CH), 126.8 (CH), 123.7 (CH), 123.0 (C$^q$), 110.3 (CH), 64.1 (C$^q$), 44.6 (CH$_2$), 34.7 (CH$_2$), 32.2 (CH$_2$), 31.1 (CH$_2$), 30.2 (CH$_3$), 23.2 (CH$_2$), 18.5 (CH$_2$), 15.0 (CH$_3$), 14.4 (CH$_3$), 9.3 (CH$_3$); HRMS (ESI): m/z calcd for C$_{19}$H$_{29}$NCl: 306.1989 [M+H]$^+$; found: 306.1987.

11f: $^1$H NMR (300 MHz, C$_6$D$_6$): δ=7.19 (t, J=2.4 Hz, 2H, CH), 7.13-7.12 (m, 4H, CH), 6.97 (d, $^3$J=7.8 Hz, 2H, CH), 4.98 (s, 1H, CH), 2.76 (d, $^2$J=13.1 Hz, 1H, CH$_2$), 2.41 (d, $^2$J=13.1 Hz, 1H, CH$_2$), 2.37 (s, 3H, CH$_3$), 2.09 (t, $^3$J=6.7 Hz, 2H, CH$_2$), 1.39-1.30 (m, 4H, CH$_2$), 1.17 (s, 3H, CH$_3$), 0.79 (t, J=7.2 Hz, 3H, CH$_3$); $^{13}$C NMR (75 MHz, C$_6$D$_6$): δ=144.9 (C$^q$), 138.1 (C$^q$), 133.4 (C$^q$), 131.2 (CH), 128.8 (CH), 128.6 (CH), 128.3 (CH), 127.6 (CH), 126.8 (CH), 123.6 (CH), 124.6 (C$^q$), 112.5 (CH), 60.1 (C$^q$), 45.3 (CH$_2$), 31.9 (CH$_2$), 31.4 (CH$_3$), 30.8 (CH$_2$), 27.5 (CH$_3$), 23.2 (CH$_2$), 14.4 (CH$_3$); HRMS (ESI): m/z calcd for C$_{22}$H$_{27}$NCl: 340.1832 [M+H]$^+$; found: 340.1836.

11g: $^1$H NMR (300 MHz, C$_6$D$_6$): δ=6.97 (d, J=2.9 Hz, 1H, CH), 6.72 (dd, J=8.7 Hz, J=2.9 Hz, 1H, CH), 6.31 (d, J=8.7 Hz, 1H, CH), 4.86 (s, 1H, CH), 3.48 (s, 3H, CH$_3$), 2.42 (s, 3H, CH$_3$), 2.31 (t, $^3$J=7.5 Hz, 2H, CH$_2$), 1.66-1.56 (m, 2H, CH$_2$), 1.54-1.46 (m, 4H, CH$_2$), 1.35-1.26 (m, 4H, CH$_2$), 0.91 (t, $^3$J=7.2 Hz, 3H, CH$_3$), 0.84 (t, $^3$J=7.3 Hz, 6H, CH$_3$); $^{13}$C NMR (75 MHz, CDCl$_3$): δ=151.7 (C$^q$), 142.3 (C$^q$), 135.5 (C$^q$), 127.2 (CH), 122.8 (C$^q$), 113.6 (CH), 111.7 (CH), 109.6 (CH), 63.5 (C$^q$), 55.8 (CH$_3$), 44.3 (CH$_2$), 34.4 (CH$_2$), 32.7 (CH$_2$), 31.5 (CH$_2$), 30.4 (CH$_3$), 23.3 (CH$_2$), 18.6 (CH$_2$), 15.1 (CH$_3$), 14.5 (CH$_3$), 9.5 (CH$_3$); HRMS (ESI): m/z calcd for C$_{20}$H$_{32}$NO: 302.2484 [M+H]$^+$; found: 302.2479.

11h: $^1$H NMR (300 MHz, C$_6$D$_6$): δ=7.32 (d, $^3$J=7.0 Hz, 1H, CH), 7.12-7.05 (m, 5H, CH), 7.01 (d, J=2.8 Hz, 1H, CH), 6.84 (d, J=8.7 Hz, 1H, CH), 5.11 (s, 1H, CH), 3.48 (s, 3H, CH$_3$), 2.91 (d, $^2$J=13.2 Hz, 1H, CH$_2$), 2.54 (s, 3H, CH$_3$), 2.48 (d, $^2$J=13.2 Hz, 1H, CH$_2$), 2.30 (t, $^3$J=7.1 Hz, 2H, CH$_2$), 1.53-1.41 (m, 4H, CH$_2$), 1.26 (s, 3H, CH$_3$), 0.78 (t, $^3$J=7.2 Hz, 3H, CH$_3$); $^{13}$C NMR (75 MHz, C$_6$D$_6$): δ=152.4 (C$^q$), 145.5 (C$^q$), 138.7 (C$^q$), 133.9 (C$^q$), 131.3 (CH), 129.0 (CH), 128.2 (CH), 127.4 (C$^q$), 126.9 (CH), 121.0 (CH), 115.5 (CH), 114.1 (CH), 59.5 (C$^q$), 55.6 (CH$_3$), 44.0 (CH$_2$), 32.4 (CH$_2$), 31.6 (CH$_3$), 31.2 (CH$_2$), 26.8 (CH$_3$), 23.3 (CH$_2$), 14.5 (CH$_3$); HRMS (ESI): m/z calcd for C$_{23}$H$_{30}$NO: 336.2327 [M+H]$^+$; found: 336.2324.

11i: $^1$H NMR (300 MHz, C$_6$D$_6$): δ=7.37 (d, J=1.8 Hz, 1H, CH), 7.35 (d, J=1.4 Hz, 1H, CH), 7.20-7.17 (m, 3H, CH), 6.90 (d, $^3$J=7.5 Hz, 1H, CH), 6.81 (dd, $^3$J=7.3 Hz, $^4$J=0.7 Hz, 1H, CH), 6.44 (t, $^3$J=7.4 Hz, 1H, CH), 4.88 (s, 1H, CH), 2.84 (t, J=5.4 Hz, 2H, CH$_2$), 2.56 (t, J=5.3 Hz, 2H, CH$_2$), 1.71-1.60 (m, 6H, CH$_2$), 1.49-1.42 (m, 2H, CH$_2$), 1.04-0.98 (m, 3H, CH$_3$), 0.88 (t, $^3$J=7.1 Hz, 3H, CH$_3$); $^{13}$C NMR (75 MHz, C$_6$D$_6$): δ=143.7 (C$^q$), 141.4 (C$^q$), 139.7 (C$^q$), 130.3 (CH), 129.8 (CH), 128.8 (CH), 127.7 (CH), 127.5 (CH), 125.4 (CH), 121.1 (C$^q$), 120.3 (C$^q$), 115.5 (CH), 63.7 (C$^q$), 43.7 (CH$_2$), 41.8 (CH$_2$), 33.7 (CH$_2$), 29.1 (CH$_2$), 22.4 (CH$_2$), 18.8 (CH$_2$), 15.2 (CH$_3$), 9.6 (CH$_3$); HRMS (ESI): m/z calcd for C$_{23}$H$_{28}$N, 318.2222 [M+H]$^+$; found: 318.2215.

11j: $^1$H NMR (300 MHz, C$_6$D$_6$): δ=6.98 (d, $^3$J=7.5 Hz, 1H, CH), 6.81 (d, $^3$J=7.2 Hz, 1H, CH), 6.56 (t, $^3$J=7.4 Hz, 1H, CH), 4.74 (s, 1H, CH), 2.83 (t, J=5.4 Hz, 2H, CH$_2$), 2.55 (t, J=6.2 Hz, 2H, CH$_2$), 2.33 (t, $^3$J=7.4 Hz, 2H, CH$_2$), 1.69-1.49 (m, 8H, CH$_2$), 1.41-1.27 (m, 4H, CH$_2$), 1.02-0.94 (m, 6H, CH$_3$), 0.87 (t, $^3$J=7.2 Hz, 3H, CH$_3$); $^{13}$C NMR (75 MHz, C$_6$D$_6$): δ=143.8 (C$^q$), 135.9 (C$^q$), 130.0 (CH), 125.0 (CH), 122.5 (CH), 120.6 (C$^q$), 119.9 (C$^q$), 115.4 (CH), 63.5 (C$^q$), 44.1 (CH$_2$), 41.8 (CH$_2$), 34.0 (CH$_2$), 33.1 (CH$_2$), 31.7 (CH$_2$), 29.3 (CH$_2$), 23.5 (CH$_2$), 22.4 (CH$_2$), 18.6 (CH$_2$), 15.2 (CH$_3$), 14.5 (CH$_3$), 9.6 (CH$_3$); HRMS (ESI): m/z calcd for C$_{21}$H$_{32}$N, 298.2535 [M+H]$^+$; found: 298.2527.

11k: $^1$H NMR (300 MHz, C$_6$D$_6$): δ=7.41 (d, $^3$J=6.9 Hz, 2H, CH), 7.19-7.14 (m, 5H, CH), 7.08-7.03 (m, 4H, CH), 6.87 (d, $^3$J=7.3 Hz, 1H, CH), 6.56 (t, $^3$J=7.4 Hz, 1H, CH), 5.16 (s, 1H, CH), 2.99 (d, $^2$J=12.7 Hz, 1H, CH$_2$), 2.91-2.86 (m, 2H, CH$_2$), 2.61 (d, $^2$J=12.7 Hz, 1H, CH$_2$), 2.53 (t, $^3$J=7.0 Hz, 2H, CH$_2$), 1.66 (t, $^3$J=7.8 Hz, 2H, CH$_2$), 1.27 (s, 3H, CH$_3$); $^{13}$C NMR (75 MHz, C$_6$D$_6$): δ=142.5 (C$^q$), 141.2 (C$^q$), 138.4 (C$^q$), 137.6 (C$^q$), 131.5 (CH), 129.7 (CH), 129.6 (CH), 129.2 (CH), 128.8 (CH), 128.3 (CH), 127.8 (CH), 127.5 (C$^q$), 126.7 (CH), 125.5 (CH), 123.2 (C$^q$), 116.6 (CH), 59.2 (C$^q$), 43.1 (2CH$_2$), 28.9 (CH$_2$), 26.6 (CH$_3$), 22.8 (CH$_2$); HRMS (ESI): m/z calcd for C$_{26}$H$_{26}$N, 352.2065 [M+H]$^+$; found: 352.2060.

11l: $^1$H NMR (300 MHz, C$_6$D$_6$): δ=7.15-7.05 (m, 6H, CH), 6.87 (d, $^3$J=6.8 Hz, 1H, CH), 6.68 (t, $^3$J=7.5 Hz, 1H, CH), 5.03 (s, 1H, CH), 3.00-2.89 (m, 3H, CH$_2$), 2.62-2.51 (m, 3H, CH$_2$), 2.32 (t, J=8.0 Hz, 2H, CH$_2$), 1.63-1.57 (m, 4H, CH$_2$), 1.51-1.44 (m, 2H, CH$_2$), 1.26 (s, 3H, CH$_3$), 0.84 (t, $^3$J=7.3 Hz, 3H, CH$_3$); $^{13}$C NMR (75 MHz, C$_6$D$_6$): δ=142.4 (C$^q$), 138.7 (C$^q$), 134.2 (C$^q$), 131.4 (CH), 128.6 (CH), 128.2 (CH), 127.6 (C$^q$), 127.3 (C$^q$), 127.1 (CH), 126.5 (CH), 122.6 (CH), 116.5 (CH), 59.2 (C$^q$), 44.0 (CH$_2$), 42.9 (CH$_2$), 32.7 (CH$_2$), 31.3 (CH$_2$), 29.0 (CH$_2$), 26.6 (CH$_3$), 23.4 (CH$_2$), 22.6 (CH$_2$), 14.5 (CH$_3$); HRMS (ESI): m/z calcd for C$_{24}$H$_{30}$N, 332.2378 [M+H]$^+$; found: 332.2373.

11m: $^1$H NMR (300 MHz, C$_6$D$_6$): δ=7.41 (d, $^3$J=7.8 Hz, 2H, CH), 7.21-7.17 (m, 3H, CH), 6.92 (d, $^3$J=7.6 Hz, 1H, CH), 6.85 (d, $^3$J=7.2 Hz, 1H, CH), 6.46 (t, $^3$J=7.1 Hz, 1H, CH), 4.89 (s, 1H, CH), 3.12 (t, $^3$J=7.1 Hz, 2H, CH$_2$), 2.73 (t, $^3$J=6.9 Hz, 2H, CH$_2$), 1.63-1.49 (m, 4H, CH$_2$), 1.10-1.05 (m, 2H, CH$_2$), 1.01 (t, $^3$J=6.9 Hz, 3H, CH$_3$), 0.87 (t, $^3$J=6.9 Hz, 3H, CH$_3$); $^{13}$C NMR (75 MHz, C$_6$D$_6$): δ=150.9 (C$^q$), 140.1 (C$^q$), 139.2 (C$^q$), 129.3 (CH), 128.9 (CH), 127.9 (CH), 127.3 (C$^q$), 127.0 (CH), 125.3 (C$^q$), 124.9 (CH), 123.3 (CH), 116.3 (CH), 62.7 (C$^q$), 45.3 (CH$_2$), 43.3 (CH$_2$), 33.4 (CH$_2$), 28.6 (CH$_2$), 18.8 (CH$_2$), 15.2 (CH$_3$), 9.7 (CH$_3$); HRMS (ESI): m/z calcd for C$_{22}$H$_{26}$N, 304.2065 [M+H]$^+$; found: 304.2062.

11n: $^1$H NMR (300 MHz, C$_6$D$_6$): δ=6.92 (d, $^3$J=7.6 Hz, 1H, CH), 6.86 (dd, $^3$J=7.3 Hz, $^4$J=1.0 Hz, 1H, CH), 6.57 (t, $^3$J=7.4 Hz, 1H, CH), 4.70 (s, 1H, CH), 3.10 (t, J=8.7 Hz, 2H, CH$_2$), 2.71 (t, J=8.5 Hz, 2H, CH$_2$), 2.34 (t, $^3$J=7.1 Hz, 2H, CH$_2$), 1.61-1.50 (m, 6H, CH$_2$), 1.38-1.30 (m, 4H, CH$_2$), 0.99 (t, $^3$J=7.1 Hz, 3H, CH$_3$), 0.88 (t, $^3$J=7.3 Hz, 3H, CH$_3$), 0.86 (t, $^3$J=7.2 Hz, 3H, CH$_3$); $^{13}$C NMR (75 MHz, C$_6$D$_6$): δ=151.0 (C$^q$), 136.3 (C$^q$), 127.2 (C$^q$), 125.0 (C$^q$), 124.5 (CH), 124.1 (CH), 121.3 (CH), 116.1 (CH), 62.3 (C$^q$), 45.2 (CH$_2$), 43.5 (CH$_2$), 33.5 (CH$_2$), 31.9 (CH$_2$), 31.7 (CH$_2$), 28.6 (CH$_2$), 23.3 (CH$_2$), 18.7 (CH$_2$), 15.2 (CH$_3$), 14.5 (CH$_3$), 9.7 (CH$_3$); HRMS (ESI): m/z calcd for C$_{20}$H$_{30}$N, 284.2378 [M+H]$^+$; found: 284.2371.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method for catalytic hydroamination, said method comprising contacting a compound having an alkyne or allene functional group with ammonia in the presence of a catalytic amount of a gold complex under conditions sufficient for hydroamination to occur.

2. The method of claim 1, wherein said compound comprises an alkyne functional group.

3. The method of claim 1, wherein said compound is a C$_{3-12}$ alkyne.

4. The method of claim 1, wherein said gold complex is a cationic complex.

5. The method of claim 1, wherein said gold complex is a Au(I) complex.

6. The method of claim 1, wherein said gold complex is a Au(III) complex.

7. The method of claim 1, wherein said gold complex comprises a L ligand selected from the group consisting of carbenes, bent-allenes, phosphines, sulfonated phosphines, phosphites, phosphinites, phosphonites, arsines, stibines, ethers, ammonia, amines, amides, sulfoxides, carbonyls, nitrosyls, pyridines and thioethers.

8. The method of claim 1, wherein said hydroamination is conducted at a temperature of from 20-280° C. and optionally with a solvent.

9. The method of claim 1, wherein said compound comprises an allene functional group.

10. The method of claim 1, wherein said compound is a C$_{3-12}$ allene.

11. The method of claim 1, wherein said compound comprises an alkyne functional group, and said method further comprises an intramolecular cyclization to produce a five- to ten-membered heterocycle.

12. The method of claim 1, wherein said gold complex is present in an amount of from 0.01 to 10 mole %.

13. The method of claim 1, wherein said gold complex is present in an amount of from 0.0000001 to 0.01 mole %.

14. The method of claim 1, wherein said gold complex is formed in situ.

15. A gold complex represented by the formula I:

wherein L$^1$ is ammonia and L$^2$ is selected from the group consisting of carbenes, bent-allenes, phosphines, sulfonated phosphines, phosphites, phosphinites, phosphonites, arsines, stibines, ethers, amides, sulfoxides, carbonyls, nitrosyls, pyridines and thioethers, chosen such that the Au complex of formula I is cationic; and X$^-$ is an anionic species.

16. A gold complex represented by formula II:

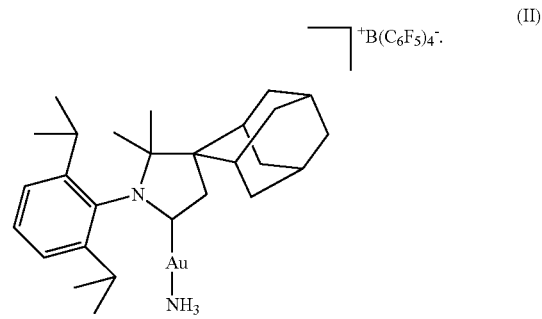

17. A method for catalytic hydroamination to form a dihydroisoquinoline, said method comprising contacting a compound having an internal alkyne functional group with an amine having an aniline functional group in the presence of a catalytic amount of a gold complex under conditions sufficient for hydroamination to occur, thereby preparing a hydroamination product, and further comprising contacting the hydroamination product with a second compound having an alkyne functional group, under conditions sufficient to form a dihydroisoquinoline.

* * * * *